United States Patent
Zimring

(10) Patent No.: US 10,785,967 B2
(45) Date of Patent: Sep. 29, 2020

(54) MICE WITH A MODIFIED GLUCOSE-6-PHOSPHATE DEHYDROGENASE GENE

(71) Applicant: Bloodworks, Seattle, WA (US)

(72) Inventor: James Charles Zimring, Seattle, WA (US)

(73) Assignee: Bloodworks, Seattle, WA (US)

( * ) Notice: Subject to any disclaimer, the term of this patent is extended or adjusted under 35 U.S.C. 154(b) by 79 days.

(21) Appl. No.: 15/578,659

(22) PCT Filed: Jun. 1, 2016

(86) PCT No.: PCT/US2016/035322
§ 371 (c)(1),
(2) Date: Nov. 30, 2017

(87) PCT Pub. No.: WO2016/196666
PCT Pub. Date: Dec. 8, 2016

(65) Prior Publication Data
US 2018/0317466 A1 Nov. 8, 2018

Related U.S. Application Data

(60) Provisional application No. 62/169,211, filed on Jun. 1, 2015.

(51) Int. Cl.
*A01K 67/027* (2006.01)
(52) U.S. Cl.
CPC ...... *A01K 67/0278* (2013.01); *A01K 2207/15* (2013.01); *A01K 2217/072* (2013.01); *A01K 2227/105* (2013.01); *A01K 2267/0381* (2013.01); *C12N 2800/30* (2013.01)
(58) Field of Classification Search
USPC .......................................................... 800/18
See application file for complete search history.

(56) References Cited

U.S. PATENT DOCUMENTS

| | | | |
|---|---|---|---|
| 2004/0053361 A1* | 3/2004 | Vallier | C12N 9/00 435/69.1 |
| 2006/0179501 A1* | 8/2006 | Chan | A01K 67/0275 800/18 |
| 2014/0142160 A1 | 5/2014 | Lee et al. | |

OTHER PUBLICATIONS

Garanto (PLoS, Nov. 2013, vol. 8, No. 11, e79369, p. 1-10).*
Tang (J. Biol. Chem., 1993, vol. 268, No. 13, p. 9522-9525).*
Pandolfi (EMBO, 1995, vol. 14, No. 21, p. 5209-5215).*
Longo (EMBO, 2002, vol. 21, No. 16, p. 4229-4239).*
Hellani (Genetic Testing and Mol. Biomarkers, 2009, vol. 13, No. 4, p. 449-452).*
Roebroek (Transgenic Mouse Methods and Protocols, Methods in Mol. Biol., 2011, vol. 693, Hofker, ed., p. 257-275.*
Skarnes (Nature, 2011, vol. 474, p. 337-342.*
Arese (Transfusion Med & Hemother, 2012, vol. 39, p. 328-334).*
Testa (Genesis, 2004, vol. 38, p. 151-158).*
Doyle (Transgenic Res., 2012, vol. 21, p. 327-349).*
PCT International Search Report and Written Opinion, International Application No. PCT/US2016/035322, dated Nov. 28, 2016, 5 pp.
Arese et al., "Life and Death of Glucose-6-Phosphate Dehydrogenase (G6PD) Deficient Erythrocytes—Role of Redox Stress and Band 3 Modifications." Sep. 17, 2012. Transfus Med Hemother, vol. 39, No. 5, pp. 328-334, especially p. 330 Tables 1 and 2.
Tang et al. "High Level and Erythroid-specific Expression of Human Glucose-6-Phosphate Dehydrogenase in Transgenic Mice." J Biol Chem, May 5, 1993, vol. 268, No. 13, pp. 9522-9525, especially abstract, p. 9522 col. 2 paras 2-3; p. 9523 col. 1 para 1; p. 9525 col. 2 para 2.

* cited by examiner

Primary Examiner — Michael C Wilson
(74) Attorney, Agent, or Firm — Lee & Hayes, PC; C. Rachal Winger; Thu Nguyen

(57) ABSTRACT

Provided is a transgenic mouse with modified glucose-6-phosphate dehydrogenase which can be used as a model and screening tool for various aspects of glucose-6-phosphate dehydrogenase deficiency.

10 Claims, 28 Drawing Sheets

Specification includes a Sequence Listing.

Figure 4

SEQ ID NO:1

CATCCACATGTGTGAGTGCAAGCACAGACACACACTACCCAAAATAAAATAT
AACAAAACTTTCTGAAGAGAAAAGGCCATGTGACAAGAGAGTTAGGGAGCACCA
AGGCTTGCCAACACTAACAATATACTTGGAGAAGTACCTGAAAGAGCTCTCTGA
AGAACCTGCCTGCCCATACCTTTATCTTAGACCTCTGATCTCAACTAGAGACAAT
CCTCTGTTATCTAAGCCCCTGCTGTGTGGTACCTTGCTGCTGTCTCCCAGATAAG
AATGAAATGCTTTGACAAGGCACTCTCTGCATCATTATGAACTTAGTCCCACAAT
ATAAAACTTGATTATGGCAGGTCTTCTCTACCCTTTCCCCCAGACTGGTCCTCTCA
GATGGTACAATCCCTGCTCAACTATTGTCACCAGGGTCCTGAAACCAGCCAGCCC
AAAAAGGCCCTGTAATACCCTTTCATTCCACACTAGGCATACCATCCTTTGGTGC
TTGTGTAATACAGGGCCAATTCACAGGCCTAGGGTCTCATAATTCCTCCAAAGGC
TCCTAAGGATCATCTCTGAGCCCCTGGGAAATCCTACCTGATGTGACTGCCTTG
TTTTTTCAGGGGCCTAGGACTCAACCAGGCTGTCTGGGCTGATGCCAGGGTATGT
GAGGGCCTTGGACTACATGGTATAGCACCTGCTAGACCTCAGGGTGGCTAGAAC
CTGAGCAAGCTAGCTCAGGTACCCAAGCACTCCATGCCTTCAAAAGTGAGCCCA
GGACAAAGCCTGAGCCCAGGACAAAGCCTGGCTCCCAGAGCTCAGGACTGCTTC
CTGGTTGACAATGCTCTATATACAGTGCACCACCGTTCACAGCAAAAGCACTGCT
CCCTGAGACGCTCACATCTGGCCTCTCCTGGCTCCTACCATATATGCCTTGTACCT
TGGAAGATTCTGATGTAGAGCCTTTTACTGTAATAAACTAACAGTTAGTGTGATG
GCTTCTCTTGGTTCTAAGAGTGCTCCCAGCAATCAAGCCTGAAAAGGTCCTGAGG
AAACTCCAACAACATACTTCCTACAGGAATATGAGTGCTGCTATGGTCTTCAAAC
ACAGGTGGGGCAGAAGGGCCTGCCCGTCCACTAGCTAGCTACCTGTTGGCATTTC
TTCAGTTGCTCCAACTCCTTTAAGGCCTGTTCCCTCTGACTCCGAAGATCAAGCTT
CTCCAAGCTCAGTCTCTCCACCAGCTTCCGGGCTTCCTGGAATTTGCACATAAGG
AACTCCTTCTCCTCCCGCTGGCTGACCTGGAAATGCAGCAGCTCCTCACAGCGTT
CCCTCAGCATCTGATTGCTCTGCCGGATAGCGTCTAGGGACAGGGAAGACAGCA
AAGGAGATAGGAGTCCTAACAGCCAGGCACTCCTATAATACTAAGTGGCCTTTCT
CTAAGAAGTCAAACCAATTCCTAGCCAGTTCCACTGATGATATGCCCCCAAGTGT
CTAGAATGCGTTACTAAACAGAGATTCTTCACTTAAAGGAATACACCAAAATCA
ACTTTCTTTTTGCCCAGAAGGTGCAGACAGAACAAGCTAGTAGTTCTGAGTTTCA
TTCTCTTCGGCTGCATATTGAAGAACAGTAAACATCCACCTTACAAATGAGGGTG
GCATGAGAAAGAAGGCAGTGCCAGTGCAGAAGACATACTCAAAGATCTCCTCTC
ACCAGAGCTGGCCATACCCTTCCAAGAATAGGACACATTTCATCTTAGAAAAAA
CCCCTCTCTCTCTCTGAAGGAAAACCATATCCCCTCCCACCTAAAAGCTTGCTAT
GTCCCAAGAAAGAATAAACCTATTCTCATTGCTTCCTATAGCCCACTCTTCCCCTA
CCTACCATGGCTTTTTAGCTTATCCTCCTTCCCCATCCCTTCTCCCTTCCCTGGTGC
TGGCTTTGAACCACATTATCTTCTGCATGTGACTCTTCACAGAGAACCCTACTTAA
AACAAAGCAAGGTAGCTAAGTTTGAAACTCTGGATGGTTCTTGGGCACATCATG
ACCTCATATCCTGCCAATTACAAGATGCAGGTGACAATAAGCTTTGTCCTTATAT
AAGTATCCCAGGCTCCTCCTGACTTTTAACTTCATACCTCCCTCACACATCAATCT
TTACCTCGGAGCTCTTGATTCTCTTCCAGGCAGCGCTGGAGGGTCTCAGGAGTAC
CCTGCTCTGAAGGCAGATGTAGCATTGCAGGCTTCCCCAGAGAAGATTCTTCACC
CAGCATGTCCTGGTCCTCTGCTGGGCCACCACTGGGCTGCACCATCTCACTCAGC
TGGTTCTTCCAGGGGTGCTTGTTCATCCAACAGGACAGTGTCTAGAAGAAAAGGG
TAGTAGGAGTGCATGACAAAGAACAGAGTTCGTTCAACTAGACTTCCATTCACA

Figure 4 cont'd.
GCAAAAGGATGGACATTTTGTCTGGTGGAACAAGATACAAAAGTGAAGTTTGGG
CTAAGACATAGCAAATATTACCATTGCAAAGAGAGAGAATTGTGGAGGAGAGGG
GAAGTAAACTGGGAATCCTACCTCCTCCACACACCTTTAAGTTGAAGCAAAGGGT
CCTGGTCCCTCACCCAGTATAGTGGAATGATTGATATATCCATGTCCTAATCCCTC
AACCTATAAATGTGATTTTTTTTACTTGGAAAAAATGGTCTTTACAGATGTAGTT
AAACTAAGGATTTCAAGCCAGGCATAGTGGTGCATGTCTTTAATCCCAGCACTTA
GAAGGCACAATCTCTGCGAATTCAAGGCCAGCTTGCTCTACATAGTAAGAACCTG
TCTCACAAAAATCAAGGCTCTCAAATTGAGATCACTGCAAGTTATATAGGTGGGC
CATGAGCCCAGTAACAAGTACCTTATTACTCAACTAGATTGATATAACCACAGGC
CAAGAAACAACTGAGCTACCCACAACTATAAGACACATGAAGGATACTCTTGTA
CAGCTTGCAGATGAAGCATAACCTTGTTCACCTTCTGGTTTTATTCTCCTGGCCTC
CAGACCTGTGAGATATCAATTTTCTGTTCTTTAAGCCACTTGGCCTGTGGTCACT
TCTTACAGGAGTCAAGAAAACACAAACACATGATAAAGAGACTTCAGGAGACC
ACATTGTACCTGAAAAGTGTTCACTGGGGATAGAGACCTCTTGTGACTTCTTTGC
TCTAAGAAGTGTGAAAGTGTGAACTGGGGTGTCCGAGACACATGACCCCTGATC
TGCTTATGCTGGCTTTTAAACCAGAGAATATGCAGGACAATACTAACCTGGAGAC
CTTGTAAATCCTGCCTCATACTGACAACCAGGAAGAGAATGATCTCAATGCAAGT
TTCCAGAAGTGGGCTTTCAATAAGGGAGACCTCCTGTAACACTGGGGAATATTGG
CTATTTATACTAAAGGTGTTGCTACCCATAGGTCCATCTGCCTGAGCCCACACAA
CTGACCCTCCCCACTTTTTCACCTACTTTCTTCCTTCAGGTTCCAGAAAGCCTTC
TCTGCTGGTGACTCACTCCCTCAAAGGCTGATGCTGCTCAGGCCCTTTTCCTGAGT
CCCCACTTCTTCACGTTGAGGAACTTTGGGACTTCTTTCTTAACTGCATTCACCCC
TGCAGTAATTCCATCCGGTCTCATGGCTTTTAACCCAAATCTTAATGTTGATAATA
TCCCAAACAGTTCTCATTCCTAAATTCCAGATATTTATAAAACTACTTGGATGTCT
AGAAGTCTTAAAAGAAGTTGGAGAGATGTCTCAGCTATTAGGAGCACTCAGTGC
TCTTCCAGAGAGCCCAAGTTCAGTTCCCAGCACCCATGTTGGGCAACTCACAACC
TTTTGTAACTCCAGCTCCAGGGGATTAGAAACTCAAAGGGAAGGGATCTAGAAG
AGACTGTTTAAAAAAATATTGAAGTATGGGCAAGGGAGACAGCTCAGTGGATAA
AGGCCCTTGCTATGCAAGCCTGGAGACATGAGAACATATAAAGGTGGAAAGAAG
ATAGCTGACTCAATGTTGTCCTCTGAGCTCTACACATTCTAGCCATGGCACCTGT
GCTCCCTGTACAAATCATACATCATGCATGCATGTGGGGGGCACACACACAAAT
AGTAATTTTTGTAGCATGCCAATTATGTCTCAAGAAAGCTGTTATTGAAAATCGC
AATGGGTGGAGCAAGAGAGATAATGGTTCAGGGATTAAGAGCACTTGTTGTTGC
AGATGTGGCTCACAAACATCTGTAACTCCAATCCAAGGGGATCTGAAACCTTCTT
CTGACTCCCTTGGGCACTAGGAAAGCATAGCAAAGCACCTATACACATAAAATA
ACATCTTCTGTAGAAAAGAAAATAATCATGGTAAAGGATTGTAATGGGGTGTGG
ATTAAAGTTAACTATGAGCTGATAGTCACAGCTAAGAAATGTGTACATGGAATTT
ACTATATTATTATTTCTACTTTTGTACATTTTAAATTTTTTCAGTAATTCAAGGCTG
ACAGCGCTATCATCTTTCACCTGCATTACTGCAATAATCTCTTTACGGGTCACCAT
GCTTTGCCTTTTCAATGGCCCTTTGCAGTTAATTGGCCCCACTGGGGCCAATTACC
TCAAAAATAACTCAAACTACTTCTCTTCTCTACCATGAACTCTTTCAGAGTTTCCA
TTTCTCCTAGTGTTAAAAAGCAAAGTCCATACAACAGCCTACAAGATCCTATACC
ACCTATACTCCCTTCCTTCCTCTCCACCAACTATTCTCCCTTGCCCTCTCTGGTCCT
TCCTTTTTCCTAGGAAATGCCAAGACAACACATTCCTTCTCAGGTCAGATAAATG
TTATGAGGACAGGCAAACAGATTACTATGAATCATTTGCAAAGTAAACTGAGGT
GCAGAAGGTAAGACCTTTAGTTGTGAAGGTACACGTGAAAACTTTTTAAAGACTT
CAAATGCACTCAAGTTTGATAAACAGCCTAGCCTGATGGCGAACACCTGTTGCTC
TAGCACTCGAAAGGCTGAGGCAGAACTTTGAGTTCGAGGTCTACCTGGCCTACA

Figure 4 cont'd.
GTGCAAAACGTGTTTCAGAAACAGTTTGATCAACAGAAAATGTCTGCTACCTAAA
GAGTTCTAGCACTAGGGGCCAAGCCCTTAGGCGACAGCTGCAGTGAAGGGAAGG
GCAGATTCAATCCGACTAGCCTAAATAATCTGGGTAGCGAATAATTAGAAGCTTG
CGGCAGAACAAACTGGGCCTAAGGTGGGGGGAAGGGTGTGGACCTCTGGAGTCT
CGGAAGCTACGAAACAGCCACCGATGGAGCCCTGTCTTTGGAGAAGAGGACCAC
ACCTGTCAGCAGAGTCGGCCAGAAGTGAAGAGGGCAGGAGCAGAGGGATCCGA
CCGCTCCGACAGAACCGGAGCTCCTAGAAAGTCCTAGTCAGGCGGTCACCCTTCC
CTTCTCTGCAGTGGAAAACTCCACTTCCGGCTTCCGGTGTCGTAAGTGCGGGATC
CGGAAGTAAAACACAGACTCAAAGGCTTGGAGATTAACCAGTGAATCAAAACCC
CAAAGTGCCATACTCTGTTCCAAAGAAAAGTCTTAGATCGCCAGCCTGCGTCGGC
CAGCAGAACACCAGAGCTCTCCTCACTGATAAACATCACACACTTATACACACA
CTTTTTTTTGAGACAGGGTCCCATAAGACCAGGGTCTCGAACTCAGAGATCTAC
CTGCCTCTTTTTTCCCGTCTGCTAGGATTAAAGTAGTGCGTCACCACGCCCACACT
CGCCCCTACCCCATTTTCAAGGCACCGCATCCGCACTAAAACACCCAAGTTTCAG
TCTGGTCCTGCTACTGGGCTCTCTGCCGCTGGGCCCCCACCAAGGAAAAAGCCTA
GAGGAAGCTGCGAAAGTCCAGCTCCGAAGCCAAACTAGCAGCTAGGGAAGGCGT
GGCTATGCTGCTAACGGAAGTGGGGTCATCCGGGAAGGTGCAGGGCCTCGAAGG
TCCAGCGGAAAGCTAGGCCATACATAATGGCTGGGTGACACAGGAGACGGGGAC
CCAGGAGAACTGTGTGGAGCTGCACTTATGACAAGACTTTGCGATCTCGAAATTG
TAGGGGCAGCGGCATCGGGGAAGGCCAAAGGGCGGGGCTGGCCAGGGATGCGC
GCGCATCTCCTCCTGCAATGATAGACTAGCCCGAAGCTCCTCCCCTCCTGCCTCT
CCTGAGGCGGGTCAGCTCAGTCAAAGCACACGCCCTCTTGCGTTAAATGGGCCA
GCGAAGCTTAGCCCCCGGAAACTGGCTGTGCGCTACAGATCTGTGAACGTGTTTG
GCAGCGGCAACTAAACTCAGGTAAAGGGGTGGTCTGATGGCATGTCGGTGGAGG
GACATGCTTCACGCTTGTACGCCGCGAGTCCCTTTGATGCGCGCTAATCTACAAG
TTTTTAACCCATCCCTTTGTATCCCGCACTTTCCCCGCATTGGGCCCATGAGGACT
AGACCTTTAGAAGAGAAGGGACTTTCGGGGATCACCCAACTGGGCCAGAAGAGA
GCCGGAGCTGAACTCCATCATCTGCACAATCAAACGTGCTCAGTTCATTGTGGAG
TTTCTGGCAGACACCCGAGTACGATACGATGGTCCCATATACAGAGTGTGATGCC
GTAACCAGATTTTATCTAGCTGCCCACAGTGGATGTCCTAGGTGAATTATATTAA
AGCTTTAGTACTTTCGTAATGTACAGCCCCTAGCGAAGGCAACTTTGGAGGTTAT
GGCTGGAGCTCAGAGGCAGCAGTTTCTGAATCTCCGAATGCATGTATGCTCGCGC
GCGCGCGCGCGCGCGCGTACACACACACACACACAGAGCATTCCCGGCCA
GTGGTTTTAGTAATCGTCACCAGCCTGGTGAGAACCCAAAAGACCCTTGGATAAG
GTTAAGTTGTCAATGCTCTTTCGTTCTCCTACCATATCAATGAGTCTTTTCTTCCA
CCAGAAAACATCATGGCAGAGCAGGTGGCCCTGAGCCGGACCCAGGTGTGTGGG
ATCCTGAGGGAAGAGTTGTACCAGGGTGATGCCTTCCACCAAGCTGATACACAC
ATATTTATCATCATGGGTGCATCGGTGAGTCTCCCTTCAGGCCCCGAGTCTAAAA
GATGAAATATAGCCTTGTGCAAGGCACTTCTCTCTCTATCTCAACTTTCCCAAT
TGACGGAACTGCTGAGGTACCCACAAGTTCTACTAGGTTGAACTCTATGGCATAT
ACTCCACCTGTGTGTCCTGATCATCACAGCAGTACCTGATATACATGTACTTGTGT
CACATCTCAGAACTCTGTGCTGAGCCATTGAGTGGAGACCAGACTTGGACCATCA
CAGGTGCTAAAGCACCACCCAGTAGCACTTCTTCCTCCTGGATGAAAAAAAAAA
ACTGATGTGCAATCAGGGAAAATTCTGATTTTAATGAATCTGTAATTTGAAAAAT
ATTACTGTTAATTTCAGTGGAAGAATCTGAGGTCCTGCCTCTCCTCTTTTCTTTC
TACGGCATGAAGTTCCCTAGGGATAAACACCTCCTCTTTGCCATATCTTCCAAAG
CCTACTGCAAATTTCTGTTCATCCCACCTAGTCCCAGCTCTGTTAGGAAAAACTG
AAGAACAGAAGCAGTCAGAGGGGTGTTGTATTGACAGTACACAGTGAGACTGGA

Figure 4 cont'd.
GCAGGTGGGGGCTTAGTAAAGTCATGGCTTAGACCAAATCACCCCCTTATGTGCT
ATGTGGCAGCAGGGCACGTTCAGTGGCCAGTGTTCGATGGCAAAGGTAAACTCA
ATTGCTTGCTTTTAATCCTGGAATCAGCTCACCCTCGTGTGACCATCTTCACTATT
AACTTATTGTGTAATCTTGGACAAGAACTTCATCAGAACTAGTGTGTTCTTGAAA
GGGTAGCCACTGGCTCAGCACCTTCCACCCTGGACCCCTCAATGCTGGAGGAGCT
CTGTGGTTTTTTGTTCACACAGAGCATTGCCATGCACCAAGGGCTACAGCTGTAG
GTCAGTGGTAAAGCCCTAACCTCATATGCATGAGGCCCTAGGTTCAATCGCAGTA
CTATCCAAAAAATGGACATCAGAACATGCCACCCCCTTTGCCAGACTTGTTTGTT
GTCTGCCTTATATTTCTGAGCAAAAATGGGAGTGGCAGAACTTCGAAAAGGAAT
GCAGAAACAAGCTGAGGAGAAGGGCCCTGCCACTGAAAGGGGAAGGGACAGAC
AAACCAAAGCACTGTCCCCTGGCTCCTTGTAGCTCTAAGACCTAAGGGAGGTACT
TAGTCGGAACACACAATACAGCAGCCCTACCCTCAGCCCTGTCTCTAGCCTAGTC
CCCTTAAAGGAGCTATGCATGTATCTGCCACAAACCTTAGCATGTGGGACTCTGC
TTTCAGTCTAAAGGGCCAAATGGAAGAGAAAGTAACTGAAGATTATTTCCCCTGC
CCCACCCATGCTTTCATAAGCATGCAGCAACAATAACCCAGTCATCGAAGATCAT
TTTTAACTGTAGGACATGAACTCTTAGATACCTTGTTGATAGCTTATTATGTGACC
TGGAACAAATGTCTACATTTCTCTGAACCCTGGTGTTTTTCATCTAACAAACAAA
AACCAGGCAGCTTTTCTGGCTTTATCCTAGGCTAATTATGTGAATTCTAGCCTCAA
GTTGAGCAACTTCCTTTCACTGCAATCAGTTTGGTTCCCCTTTGCTCTCCTCTGCT
CTGGGAGTAAGAACCCGGGCTTCCAGAGTAGAAATAGGAACTATTAGTTCCAGC
AAAAGGGAGTGGGGAAGAAAGAGATTTTCTAAAAAGCATCATTGTTTCTTTCTGT
TCCTCTCAGAGGTCCTGAGAGAGAGAGACAGACAGACCCTATGCTTAGCCCCTA
GAGTAGCTCCTGCCTGATACTTCACTAAATGCAGGTGCTATCTGATCTAGGACAC
CTGCAAGTTCTCCATTCATTAAACGTAGCAATCAAGTGTCTCCCATTACATAATA
GTCTCAGTTCCTATCCTCCTTGTGGGACAGTGTACTTTGGGGAGCTGCATGTAA
CAGAAGTCACAAATGGATTCTTGTGTACTAAGGCCCCTGCAACACACAGGTCCCA
AGAGGACCTAAAGAGCAAGGCAAGTTGAGGATAAGGGCAACTGCCCTCTAAGTT
TGGAACAAGCTCAATGTGACCTAGAAACTAAAAGGAAGCTAGTGGCTGGCAGGC
CTCAAGCCTAGGAAACTGGAACAAACTAGGGCAAGTTGATCCTAAGTAGCCATC
CTCTGCCCCTTCTTCCTCCCCAGGTCCTTACCCAGTCCTTACACATGTACCCAGCT
TCCTTGGTGGGGACATTCTCAATGTGCCTCACTGTAGCCATTCCTCTTCTCAGAAC
TCCCACCCCAACAAGAAAGTGAACAGAAATCCTTACTGTCCCACTCCTTATGGAC
CAGTGCAGGGAAGGAACTGAGCCTAGAAGGGCATCTCCCCAGCCAATAGGACC
TTGGTGAAACTAGAGAGTGAGTGAGTCTTTCTCCTATGCAGAAGAAATGGAGTA
GGTCTGGGAGTCCACATGGGCAGATAAGCTCACTATGGGCCCATCTCTCTAGACA
TCTGATTCCTTACCTAGCCTATGTGACACCCATAGATTCAGTGAGCACTCAAGGT
CCATCCTGCTGACAGGACTGTGTGAGGAGTGACCTGGCAGTCCCAGCCCATCCCT
CTACTTGGGTCATTTCTGAGCTGACTTCTCCCTTGAGCTGGTAAGATTCTTGCTGT
GTCATGATGACCTTGGCATTCTCCCAAAAGCCTGGTGACTCACAGAGTGCCAGGG
TGTAAGAAGGAGGCCTTTTGTTAGATTTTTAGCCGAGACCTACCTCGTATCTCCCT
ATATCTCATTCAGTGCCTGGAAAATAGCCGACCCTCAGTCGCAGTCTTCACAGTC
TAGAACTGTGTCTTGGAAAGCTAGGTGGGTCCCTCATCCCCAACAACTCTTGGGA
ACTGAGTGCCTCACTCCTGCAAGGCCTTCACTCGAATTTCTCCCAAACAAAAGGC
TGGGTATGATTTGACTTCAAAAAACAAGAACCCAAACCTCAGCTAACTATAGAC
CAAGTGGTACTCAGGGTCTCTTTGCCTTTATCTGGCCAGATATCTGTGGCTAGAG
ATCTTAATCATGTCTTAATTCTCCTAATTCACCACATATCCTTAGGTAGATCCTTC
CCCCGCCATGGTACTTGGGCAATATGAGGGGGTAGCAAAGATGAGAGACTTCCA
GCCGTCTCTCTAATTGCCCCTACTCCCACACATGTTAAGTTTAGATTTTAGTTCTT

Figure 4 cont'd.
CTCATGTTCCTTACTTCAGAGGAGTTTAGTGAGAGTCATGAAGCCAACAGGAAAG
ACAGGGTGATCCCATCCCTGAGAAGAATGGCTACCTCCCACCCCCACTGTCCTTA
GTCCTACCTCACCTCCCTTGGGTGACTTGAAGCCAGGCAGACTGTCAGTTGCAGG
CTGAGCCAAAACAAGGAGAGCAGGTTCTATGTCTTGTTAATCCCAAAGAGAACA
AGAACAAACAGCTCTGGGTGTGGGGCAACTGTGACTCAGCAGACCAGTCCCCTG
CCACCAACACATTGGCTGGAGTCTGTACTGATTCCTCCCAGTTAGTTGGAATTTG
ATCATAAGCAAACACTGTCTGCTTAGAAAAGTCTACAAGCCAGGGTTCTCATTGT
TTCTTTTAGTTTCTAGTTCCCAGCAAGCCAGTCCTTTCCAGAGTGTGTGAGGACAG
GATAAAACCCTCTGAACATGAGCAGTAACCCACATCCCACTGATGGAAGATCAT
AGAGGCAGGCATTGAGAGCATTCTGAGGAACTAAGAACCATCCTGGGGGGAAAT
CCTGGCCCAGAATTGGACTTGTCTATGCTGGGCTTTGTGGGACCTATAAGGGCAA
CCATCTTGCACAACAGAGTAAAAGCTTTGCCCAGCAGAGTGACTTGGGGGACAG
TAATTAGGCCACTCAGGTGGCCATGCTTGGTATCACATGAGGAAGTGACAGATG
AGGAGGCTCCAGAGCAATAGAAGCCCAGCTGGCAGCAAGTCTTAGACATTTTCC
TAAAGATAGTCATAGCATTGAAGTTACTTACTGGCCATTGGGCTCAGGCTCCCAG
AAGTTCATATGGAAGGTGGTAGTTATCATAGGAACCCACTCGCCAATGCTCAGG
ACTTTAATTCTGAGCAGTTGACAGACATGGGCACTGAATTGCTCGCTCATGCCAA
CACAGGGTGTTAGGGTTTGGCAACAGTCCTCTATGAAAGTTTTGGGAACCCAGAA
CCTAGAAATGACATGCACACAATTGATTCCATGGACCGGTCACTCAGCAAACCC
CTGAGAACAAACATTCAAGCCATGGGAATCCCTGAGTGCCCATAACTATCCTTAT
CCAGAACTGCCATTTCCCATAGAAATGGGCTCATCAGTGCAGCTACATGGTTAAC
TCTCTTTTGTTTGTTAATATGCTAACCAAGTCTACTCAGCCTCAGCCTTCCCTGAG
CCTCTGCTCCCCTTTTTTTTTTTTTTTTTTTTTGAGACAGGGTCTCACTACGTTTC
CTGGGCTGACCTTGAACTTGTTATTCTCCTGTCTCAGCCTCCCAAGTACTGAGATT
ACAGGTATATACTAGTACATCTGGCTAAGTCATTTTGAAGTTTGGATCAAAATG
GTATTACCACTACAATGTTTTGATTTGATTTGATTCATTTTATGTACATAGGTATT
TTGCCTGCGTGTATGTCTGTACCACTTGCATGTCTGGTGCTCTCAGAGGTCAGATC
CCTAAAACTGGAATTACAGAAGGTTGTGAACCACCATATGGATGCTGGAAATCA
AACTAATGTCCTCTGAAAGAATAGCTTAGTGCTGTTAACCACCAAGCAACCTTCC
CAGCCCCACCTCTTCATTTTAAAGAGTTAGTCAGCTTAGGCTATGTAATCAGCTT
GGGCTATGCTGTATATTAGTTCTACCTGTGATAACAGAAAGTTGCCTATTAAATA
TTGTACTAAAGAGAACAGCAGGGCTGGAGAGATGGCTCAGTGGTTAAGAGCACT
GACTGCTCTTCCAGAGGTCCTGAGTTCAATTCCCAGCAACCACATGGTGGCTCAC
AACCATCTGTAATGGGGTCTGGTGCCCTCTTCTGGTGTACTCATATGCATAAAAT
AAATAAATAAACCTTTAAAAAGAGAGAGAGAACAGCAGTTCACTCTCTGGGGGT
CCCTGATTCATGGAGCCCAGCATCTTTCCAGGTGATGGTGATCCCAGCCAGGTAA
AGGAGGATTGTTCGAGCTGTATTCTGCATAGCTTATTTAAATTTTGCAAGGTTCAT
GCCACCCAGACCCACTGCATCTAAAACCTCATCCCAAACACCTGAGAAATTAGT
GCCAAAATGCCTTGTTAGAAAGTGGTGTTTTGAGTTTTAATTAGATATACCTGTA
GTAAAAGTTTCAGCAAATTACTTTTGTATAAATATTCAGGTTCTTAAAACCAGAG
TTGCTTTTTGTGTAGAGAGTGAATTAGAATATAGATGGGACCAGTGCCTGACTCC
AGTTGCACTTGCTCACCTCTCCCCATGAAGTAGTACTATCCTGTGTGTGTAGCATG
GGTTCACACTTCTCCCACGTTCCTAATTATAGGGTTTGAGATGAAAGGGCAAATG
CCCTACTCTATTCCAAGAGATTGGTAGTCATGTCTGCCCCTTCTTCTTGTACCTGG
TTTGGCAGGGTACAAAATGAAAGCATGTTGGGCTGTTACTGATTACTGGGATACT
GAACTGAGTGTGCACATTAGCTTGGAAATGAGGATGGTGAACTTATGGCTAGGTT
CTTTATAATATTTACTTTTGTAAATGGTATTGTTTTAAATTGCTAATTTTTCCAACT
CACTGGTAAATGAGTTTTATTTACTGTTAGTAAATAAAAGTTGCTAGCTTGTATCT

Figure 4 cont'd.
ACTAATATTTACAGTGGGTTCTTGGGGGTGCTGTTTGGTTTATTCATTAGCTTTGC
AGTGTTACAGATCAAACCCGTTGCCTAACACTTGACCACTGAGCTATATCCTTAG
CCCCAAATATTTATAATTCTTATTGGAATATTTCATCAAAAATAACACAGACCTT
AAGGGCGCAGCTGGGCAACTTTTCACAAACTTGGCACACCCTTGTAAATTTCTCT
CCCCATTAAGAAAGGGGGCTTGAAAGATGACTCATTGGTTAAGAGTATTTGCTAC
TTTTGCTCAAATCCAAGTTTAGTTCCTAGTACCCACAACAGGCAGCTAATAACTC
CTTATAACTCCCAATCCAGGGGATCCAGTGCCCTTTCTGCCTTCTATAGGTACCT
GTACTAATGTACATATACACCCCCAACATACCCATACACATAATTAAAAACAAA
ATAATTACTTAAATAAAAGAAGAAACAGAGTATTATCACCTAAAATCTTAGCA
CTGCAGAGGCTGAAGCAGGAGATTCACTTCAAGAAAGACATTCAAAACTAGCCT
GCCTAAGCAACATAACAAGACCCTGAATTAAAACAATGTAAAATAGGGCTGGTG
AGATGGCTCAGTGGGTAAGAGCACCCGACTGCTCTTCCGAAGGTCCAGAGTTCA
AATCCCAGCAACCACATGGTGGCTCACAACCATCTGTAACAAGATCTGACTCCCT
CTTCTGGTGTGTCTGAAGACAGCTACAGTGTACTTACATATAATAAATAAATAAA
TAAATAAATATAAAAAAAAACAATGTAAAATATATGGTGGTATACTTCTCCTGTA
ATTCTAGAAAGGTGGAAGAAGGAGGATTAGGAGTTCAGAGCTAGCCTTAGCTAC
ATAGTGAGCTTGATGCTAGTCTAGGATACAGGAAACCCAGTCTCAAAAAAAAAA
ATGTTTTTAAGTAACTAAAGCCAGGTGTACTGGTATACAGTTGTAATCACAGCAC
TTAGGAGGCTGAGGCAAAAGGATTACCTTGAGTGTAAGGACAGTCTGAGCAACA
TAGCAAGTTCAAAACTAGTTAGGATTACATAGCAAGACCCTGTCTCAAAGCTACA
GCAAAAAAAAGGTATGTACCCAAAGAACCCCACTTTGTAGCTATTGTTTCCCT
AGGAGTAATGTCAAACTTCCTCTCCACCCCTGCTCAATTATTTTCACCCTCTTTT
CTTGGTACATATTGTAATGCATAAATGGTAGCTATATTGTTGATGACCTAATCTA
GGACATTTCTGTCTTCCCACACAATTCTTGGATACCCCTGGCCAGCCAGTCTACC
GCCTCTCTAGGCAACTACTCATCTGAGTCCTGTCATAATAGTCTAAAGTTGCCCA
TTCTGGGGCTTTTAAGTGAATTCATTAGTATATAGTCTCTTATGTCTAGCTTCTAT
AGTTCATCATAATATATTTTTAAGATTTGCCAACACTGAAATAGTAGCTCATTCCT
GAGTAGCTGAATACAGATATACAATTTGTCCATCTGCATGCTGGTTTATTTGACC
ATTTCTGGGCTATTTTAAATTAAAGCTGCCATGAACATTCATGCACAGATCTTTG
GGCAGCTGGTTGCCTGCTTTTATTTCTCTGGAGTAACACCTAGATATTATAGCTAC
TTCACCTGATAAGAGGCTGCCATGCTGTTTTAGATTTAATCATTGCAGGTTTCTAC
ACACAGTCTATGAGTTCCATACCAATACTAGGTCTTCCTTTTGCTTTGGCTTTTG
CGGGAAGGGAGTTCTATAAGTATGTACCAACTATCATCATTTGTATTACAGTCAT
TCTAATGAGTCTGAAGTAGTGTCTTGTTAAAGTTGCATTTTCTGATACCTGATGAT
CTTGAACATTTCCCATGTATTTATGGCCATTCGTTTCCATTCTGGTGAAACATCT
GGCCAAACCTTTTACCCATTTCAGTTAGATTGTTTTTCAGTGTGTCATAGGAGCTA
CTTAGATATTCTGAATACAGGTAAGTTTAGTGAATACTATCTCTAAGGTTGAAAC
TTGTCTTTTGGTGCTAGGGATTATACTCTGGGCCCTGCCCATGCAAAGCACATA
CCCTACCACTAAGGTCATAATGCCAGGCTTGCCTATTTTCCTTCGTTTCTTTTGTTT
CATAATACTGGATATTGAACCAGTCATATGCATGCCCTTCATTTTTTCATATCTC
TCTTTCCTCTCCTATATTCCCTACCCCCAGTGCAGACCTTGAGCCCTTTATGTATC
CAAGGATAATCCTGAAGTTCTTATCCTCCTGCCTCTACTTCTGGAATGCTATGATT
ACAGGCTGCAGTACAATGCTGGCTTATGATTATTACTTTATATCCTAAGAAATCT
CTACCTACTCCTATCACTTTTTAATCTAGCAACTTGGAAAACCCTCATTAATTCT
AATAATTAGTCTGTAGGTTGATTTGAGGTACTTTTTAAATAAACAAGCTATCAT
CTAATAATGACAGGTTTTTGTCCTCTATTCCAAACCTTATACCACTTTCTTTCTTTT
TTCTTTTTTTTTTTTGGTTTTGTTTTTTGAGACAGGGTTTCTCTGTGTAGCCCTG
GCTGTCCTGGAACTCACTCTGTAGACCAGGCTGGTCTTGAACTCAGAAATCCACC

Figure 4 cont'd.
TGCCTCTACCTCCCAAGTGCTGGGATTAAAGGCGTGTACCACCACCGCCCGGCCA
CTTTTCATTTTCTTGTCTGATGACACTATCAAGGGCTTTTAGTTTAAGACTGACTA
AAGAAACAATAGCAAGCATTTAGAATTTTCTCATAGACACCTAGATGCGTGTCTG
TGATTGTGTTTAAAGAGAAATTTAACTGAAGAAGAGAGACCTACCATGAATTTCA
TAGAACACACTATTGATTGGTGTCCCTGAGTGAACAAAAGGAAATTGGAGAGAG
TAAACTAAGTGTCCATATTCATCTCTCGGCTTCCTTGTTGACAACACAAACTTCAC
CCCCCATCACCACGCCTTCCCTGACATGGCAAACTGTACCCTCAAACTGTAAACC
TGAATAAACCCTCATCCCCGAAATTTCTTTCTGCCAGGTATTTTTTTTCATAGCA
ACAAGAAAGGTAAACAATACCCCATTTTGTTTGTTTTGTTTTTGTTTTTCGAGACA
GGGTTTCTCTGTGTAGTCCTGGCTGTCCTGGAACTCACTTTGTAGACCAGGCTGG
CCTCGAACTCAGAAATCCTCCTGCCTCTGCCTCCCTAGTGCTGGGATTAAAGGCG
TGCGCCACCACGCCCGGCTCAGAACCCCATTTTGAATGGTGTTTTAGGGTGTTT
GGTAGATGTCCTAAATCAAATTAAAGAGATTTTATTCCCTCTTTGATTAAAAAAA
AATAAATAGAATTTTTTTCTGAAACCCTTTATCTGTATTTGTTGAACTTAACAAAG
TTGCTATATTTTAAAAATCAGTACACAGACATGAAGATTTCTCAGAGGCCTATTG
TAATCACAGCTTCTCAGGAGTCTGGGGCAGGCATTCAAAGCTAATGTTGACTACA
AAGTAACTTCCAGGCCAACCTGAGTAACTTTTTGAGACTCTGTCTCAAAAGATAG
GCAAACATGGTGGTACATGCCTTTTTAATCCCAGGAAGTAGAGACAGGTAGATTT
CTGTGAATTTGAGGCCATCCTGTTCTTCTCAGCAAGTTCCAGGTCAGCCAGGGAT
AAGATCTGTGACTGTCCTAGTTAGGGTTTCTATTGCTATGACCAAAAGCAAGTTG
AGGAAGAAACAGTTTATTTGGCTTACACTTCCACATCATAGACCATCACTGAAGA
AAGGAAATGAACCTGGATGCAGGAGCTGATACATAGAGGCATAGAGGGATATTT
CTTTTTTCTTTTTTTGTTTTTTTTTTTTGGTTTTTTTTTTTTGGTTTTTTTTTTTTT
TTTTTTTTTTTTTTTGGTTTTCGAGACAGGGTTTCTCTTTATAGCTCTGGCTGT
CCTGGAGCTCACTTTGTAGACCAGGCTGGCCTCGAACTCAGAAATCCACCTGCCT
CTGCCTCCCGAGTGCTGGGATTAAAGGCGTGCGCCACCACGCCCGTCGAGGGAT
ATTTCTTACTGGCTTGTTCAGCCTGTTTTCTTATAGAACCCAGGACCATCAGTCAA
GGTTGGTACCACCCACAATGGGCTGGGCCCTCCCACATCAATCACTTAAAAATGT
CCCACAGGCTTGCCTACAGGCTGATCTTATGAGAGTATTTTCTCAATTGAGGCCG
CCTCCTTTCTGGTGACTCTAGCTTGTATCAAGTTAACATAAAACTAGCCAGGACG
GGACTATAGTCCAGTAGTTGAGCACTTGCCTAACATGCTTGATTTCCTGAGTTCA
GTCACCAGCGCCATACACACACAATGGTTTTTCAGAATTTTTCATTTAATTTCTT
TTGAGGGGTATTGGTTTTTGTTTTTGTTTGTAGACTTGGTTTCTTTGTATAGCCTTA
GCTGACCTGGAACTCATTCTGTGGACTAGGCTGGCTATAAACTTAGAGATCCGCC
TGCATCTGCCTTCCAAGTACTGAGATTAAAGGCATGTACCACCACTACCTGGCTA
ATTTTTTTTTAAGATTTATGGTTTTTTATTTATGTGTCTGTCTGCCAGCCAGTCAGC
CACATGTGTATGGATACCCACAAAGGCCAGAAGATGTCATTAAATTCCCTGGAA
CTGAAGTTACAAGCAGTTGTGAGCTGCCTGATATGGATGCTGAAAACCAAACTTG
GGACGCTGTACAAAACCAGCAAGTCTCTTAATACTGAGCATCTCTTCAGCCCATT
TTTAAATCTTTTAATGTGATTTTCAGTGATTGATTTTGTCATTGCTCTCGCTACCTT
TATTCTTTGAGACAGGAACCCTCATTGAACCTGCAGTTCATCTGTACAGCCAGGC
CAGCTGACAAATGAGTTACAGGACTATATAGAAAACTCTGACTCAATAAACAA
TCAATCAATCAATCGAGTTTTACATCAGCCTTTGTCATCAAGTTGTAGAACTAAA
GTTCTCAAAGTGCCCTTAGAAGTATTCCTCTTTATTCTGTCTTCAGGGGAAATTTA
CTTCAGAGTGGAATTCACTCTTCCTTGACTCTGGTAGAAGCCATTAGCAATGCTTT
TCAGGCCAGGAGTTGTCTTTGTACATTGCCACCCCTTAGGTCCATTCCTCCATTAT
ATCCTAGGTTGGATCTTTTTTTTTTTTAAAGACATTTTCCATCTTGCTGAATATG
GTGGCACACATTTGTAATCCCACTACAAAGAAACAAGAGGGTTGTCTGTAGTTTG

Figure 4 cont'd.
AGGCCAGCCAGGACTACATACTGAATTTAAGACCAACCTGGGCCTTTATTCCCAG
CACTGGAAGACAGAGGCAGGTAGAGCTCTCTTGAGTTTGAGGCTAGCCTGGTCT
ACAGAACTTCCAGGATAACCAGAGCTACACAAAGAAAACCAGACTTGGGGATGG
AGGGTGGACGGTACCAACATTGGTTACATGGCAAGGCCCTGTCTTAAAAAAATA
AAATTAAAAAAATTTTTAATTCTGTGTCTCAGCTAGGCTGTAGTGGCACACACAT
TTAATCCCAGCACTCCGGAAGCAGAGGCAGGTGGATATCTGTGAGTTTAAGCTCA
ACCTTGTCTACAGGATGAATTTGAAGACAGCCAGGACTATACAGAGAAACTCTA
TCTTGAAAAAAATAAACAAAATTCTCTGTCTCATTCTAACTTGTTAGGGTTTTGTT
AGGCTGGGTTGGGTTTTGTTTTGGATTTTGGTGGTGGTGGTAGTGTTTGAGATAG
GGAAAGGGTCTTATGGTGTATACCTAAGGCTGACTTTGAAGTCCAGATCCTCCTG
CTCCAACTACCCAAGTACTGGGATTATAGACCTGTGCCACGAAGCCCAGCTTTC
TTTCTTGTTTTGGTTGTTTAGTTTGGTTTGATGTTTGGGGAAGTTGGTTTTATTTG
GCTTGTTTTTTTAATAGCTCTTAATTTATTCTTTGAGAATTTCATACATGTATACA
ATGCATTTAAAGCATATCTACCCTCCATTCTCTCTCTCAACCCCTCTGGACAAC
CTCCCCGATCCCCCACCCAATTTTTATTTTGTTATAACCCATTAAGTACAATAAT
TGCTTCCTACATTCTCATGAGCATGGAACCATCATCCACTCCTTGAGCAATTACC
AAGGGGCCATGAAGAAAAATTATATTCCCTAGCAGCCACTGATGGGAAGTGGAT
CTTCCAACAGATCCTTAGCTAGGGGTAGCAGCTTGTGAACTACACACACTCAGCA
TGCTGGCCAACTTGATCTCATGCAGGCAACTACAGCTACTGTGGCTTCATGTGTA
CCACAGCCCTGTCATATCAAGAAAATAGCAATTCACAGCTCTCCTCTAGCGCTCT
TTTGTTAGTTTTCTACTCTGTTTGTTTTTGTAGGGTGGGGGTGGAAATCAGAACCC
TTGCCTACTCCAAAATCACTGAGCATCTTCTCCAGCCCAATTTTTCCATTGAATTT
TTTCACTGCTACCTTATTTTTTTTTAATTCTGATTTAGAAGAGGTGATTTTGAAA
CAGTATCTCCCTCAATATTGGGAGAATATATTACCACCAAATCTGGCCTTTGTTA
CAGAGACAAGACTTCATTCTGCATCATCAAACTTTTCCTGCCATTATTTTTCTAAC
TTTCCAAATTGAATGACCATCTCATTGCCTTCTAGCTCCGGTGACATCTGAGGCCT
TACCTCACAGGTTTTGTCTTTCTTTTATGTGCTGCCTTTATCATCCTTAAGCTCTAA
TGAATTCGATGTCTAGGGTTTCATCTTGAACCCAGCAGTGTCATCTACTCATCTGT
TTAATTAAGCCAAGCAGGCATAACTTCGTATAGCATACATTATACGAAGTTATGA
TCTAAAGGCTTGAATCTCGGGGCTCTTCTGTCTGTATATCAGGCAAGACAGACAT
GCTTGTGGCCCAGTAGTGATCCTGAGTAGTGCCCAGATCACCAAGGGTGGAGGA
TGATGTATGTAGGTCGTGTCCCCAGCCACTTCTAACCACACACCTGTTCCCTCTGC
CACAGGGTGACCTGGCCAAGAAGAAGATCTACCCCACCATCTGGTAAGTGTGTC
CCACCACTGCCCCTGTGACCTCCCGCCAGGGACAGGCCTGGTCCTGCCCTGCCCG
CACTGGTTACAGCTGTGCCCTGCCCTCAGGTGGCTGTTCCGGGATGGCCTTCTGC
CCGAAAACACCTTCATCGTGGGCTATGCCCGTTCCCGCCTCACAGTGGCTGACAT
CCGCAAACAGAGTGAGCCCTTCTTCAAGGTGGGTGGTGTCAGGGCCTCCCCCAG
CCTGGTTCTGCCCTCTCTACCAGCCCCAGCATGGCCAGCTTCGGGGACCTCCCC
CCATCCCATCCCGGGATGCTCTCCTCCTCTCCTGCCCCGCCCCGCCTGCTCTCGTA
CTTCCTTGAGACCCCCATTACCAGCCCCGTGACCAGGACCCACAGGTCCCCTCC
TGCTGTGCTCTGCTGCGTTTTCTCCGCCAATCATAGTTGGGTGTCATGATTTTGGA
GAGAGAGCTTTCTCCAGTGTATTTCTCCCAGGTCAAAATATCCTGAAATCTGGCC
TCTGTCCTAAGGCACAGGGGTCCCAGCCTGGGGCAGTGTCTGTGCTGCCTGCTTT
GGCCTCCCTCCCTCTGGATGTGCAGAGCTGCTAAGATGGGGCTGAACCCAGTGTG
GGACGGGGACACTGACTTCTGAGGGCACCCTCCCTGGACCTCCAGGGAAGACCC
TCCACTCCCCTGGGGCAGAACACACACGGACTCAAAGAGAGGGGCTGACATCTG
TCTGTGTGTCTGTCTGTCCGTGTCTCCCAGGCCACCCCAGAGGAGAAGCTCAAGC
TGGAGGACTTCTTTGCCCGCAACTCCTATGTGGCTGGCCAGTACGATGATGCAGC

Figure 4 cont'd.
CTCCTACCAGCGCCTCAACAGCCACATGAATGCCCTCCACCTGGGGTCACAGGCC
AACCGCCTCTTCTACCTGGCCTTGCCCCGACCGTCTACGAGGCCGTCACCAAGA
ACATTCACGAGTCCTGCATGAGCCAGATGTAAGGCTTGCCGTTGCCCTCCCTTCC
CGCCTGCCAGGCTGGCCCAGGCAGTGCTCCCACCACTCTATGAGCGTGTCCGGGG
CCGGGGATCTGGGCAGCATCCATGGTGCCGGGGCCATCCCCAGCGGGACCACAA
GGTGGCAGCGTTGCTCCACGAAACACCGCCTTTCCGCTCTGCTTCCCCAAAGGCC
CGGCCAGGCCGCAGGGTGGCAGCCTTGCTCTGCAATGCAGCATGGCCCGCGCT
GGGTGGTTTCCCAACCCAGCCAGAGGCTCTTGTCCTCTGGCTGGTTTTGAATGCG
GGGGTAGTAAAGCAAAGGTCCTCTACGCGTTCTCATTTTCAAAACCAATGAGGA
AGCCATGGCTTGGATGCCTCCTCCCCTGCTCCCTACAGGCCTTCAGGCCACTC
AGACCCACCGGGGACCCAGCATGAGGCAGGAGGGGAACGGGCCCCGGCAGCA
TGCCAGCAATGCCACCCTGGCACCCAGGGTGGGAAGGCTTCCCGGAAGGTGTTG
AGCCAGAGGGTCATCTGGGAACACAAGGCACGGGAGGTGGCCACGGGGGCGAG
GAGGTTCTGGCCTCTACTCCCCTGGGAGGGCGTCTGAATGATGCAGCTCTGATCC
TCACTCCCCGAAGAGGGGTTCAAGGGGGTAACGCAGCTCCGGGCTCCCAGCAGA
GGCTGGAACCGCATCATCGTGGAGAAGCCCTTCGGGAGGGACCTGCAGAGCTCT
GACCGGCTGTCCAACCACATCTTCTCCTGTTCCGTGAGGACCAGATCTACCGCA
TCGACCACTACCTGGGCAAGGAGATGGTGCAGAACCTCATGGTGCTGAGGTGGG
GCCAAGCCTGGGCCGGGGACCAGGGTGGGGGTGGTACTCAGGAGCCTCACCTG
GCCCACTGCCTCCCCGAGGACGAATTCCTCCAGAACTCAGACAAGGGTGACCCC
TCACATGTGGCCCCTGCACCACAGAGGCCCAAGGTCAGTTCCTCCACCTTGCCCC
TCCCTGCAGATTTGCCAACAGGATCTTCGGCCCCATCTGGAACCGGGACAACATC
GCCTGCGTTATCCTCACCTTCAAGGAGCCCTTTGGCACTGAGGGTCGCGGGGGCT
ATTTCGATGAATTTGGGATCATCCGGTGAGAGCTCTTCCTCTCCTGGGAGGCT
GGCACAGGGTGGCAGAGCCAGTCACCCTGCAGGGCTACTCTTCCCTATCTTGGGG
GAGCTCCTCCTCACCCTGCAGTTCAAAACCTAAGTGTCTGAGCTATCAGACCGGG
CTGGAAAGGGCTGGACCCCTACACAGCCAAGCACCCCACGGTTTTATGATTCAGT
GATAGCATCACCATGTCCTTCCTTGATTTAAGGGGACCTGGAAGACAAGGGGGA
TCAGGAAGTGAGTCTTGCAGCTTGTCACTAGGAAGCCTTGTTTGGGGTCCCCATG
CCCTTGAACCAGGTGAACAGGGCGGGGAGCTAAGGCGAGCTCTGGCCTCTTCCG
TCCCCAGGGACGTGATGCAGAACCACCTACTGCAGATGCTGTGTCTGGTGGCCAT
GGAGAAGCCCGCCTCCACCAACTCAGATGACGTCCGTGATGAGAAGGTAGGGGG
TGCACCCCAGTCCCCAGGAGCATGCCCTGTCGCAGGCCCATCTGTGACGAGGCA
CTGAGCTGGGGTGTGCATGCAGAGCAGGTGTCCTCAACCCCGGAGAAGTCACCA
CCTCTGAGCACAGCGTGGCCTCCCGGAGGTGACCTGGACTGGCAGTCATGAAGC
CCAAGTTGTCATGTCCCAGGCCTGACAGTCACTATGTGACCAGGGAAGGCCATTG
CCTCTCTGGGCCTCAGCTTGTTCATCAGAATAGACTCGAGATGGACCAGGGTGGT
CCTGGAGGGTCCTCAGGGAGGGGCCCTGAGCTGGGCCTCTGGCAGGGTGAGCAG
AGCCAAGCAGGGGCCTCCTCCTGCCCTGAGGGCTGCACATCTGTGGCCACAGTC
ATCCCTGCACCCCAACTCAACACCCAAGGAGCCCATTCTCTCCCTTGGCTTTCTCT
CAGGTCAAGGTGTTGAAATGCATCTCAGAGGTGCAGGCCAACAATGTGGTCCTG
GGCCAGTACGTGGGGAACCCCGATGGAGAGGGCGAGGCCACCAAAGGGTACCT
GGACGACCCCACGGTGCCCCGCGGGTCCACCACCGCCACTTTTGCAGCCGTCGTC
CTCTATGTGGAGAATGAGAGGTGGGATGGTAGGTGATGCCTTCGAGGCCCAGCA
AGGCAGAACTGGGCATGCCCTGTGTGCGGGCACTGGAGCTCCCACTGAGACACT
CACGCACTGGTCCACACCCTGAGAGAGCTGGTGCTGAGGCTGCCCTTTCCGCCAC
GTAGGGGTGCCCTTCATCCTGCGCTGCGGCAAGGCCCTGAACGAGCGCAAGGCC
GAGGTGAGGCTGCAGTTCCATGATGTGGCCGGCGACATCTTCCACCAGCAGTGC

Figure 4 cont'd.
AAGCGCAACGAGCTGGTGATCCGCGTGCAGCCCAACGAGGCCGTGTACACCAAG
ATGATGACCAAGAAGCCGGGCATGTTCTTCAACCCCGAGGAGTCGGAGCTGGAC
CTGACCTACGGCAACAGATACAAGGTGCCCTACAGAGAAGGAGCAGTGTGGAGG
GTGGGCGGCCTGGGCCCGGGGGACTCCACATGGTGGCAGGCAGTGGCATCAGCA
AGACACTCTCTCCCTCACAGAACGTGAAGCTCCCTGACGCCTACGAGCGCCTCAT
CCTGGACGTCTTCTGCGGGAGCCAGATGCACTTCGTGCGCAGGTGAGGCCCAGCT
GCCGGCCCTGCATACCTGTGGGCTATGGGGTGGCCTTTGCCCTCCCTCCCTGTG
TGCCACCGGCCTCCCAAGCCATACTATGTCCCCTCAGCGACGAGCTCCGTGAGGC
CTGGCGTATTTTCACCCCACTGCTGCACCAGATTGAGCTGGAGAAGCCCAAGCCC
ATCCCCTATATTTATGGCAGGTGAGGAAAGGGTGGGGGCTGGGGACAGAGCCCA
GCGGGCAGGGGCGGGGTGAGGGTGGAGCTACCTCATGCCTCTCCTCCACCCGTC
ACTCTCCAGCCGAGGCCCCACGGAGGCAGACGAGCTGATGAAGAGAGTGGGTTT
CCAGTATGAGGGCACCTACAAGTGGGTGAACCCCACAAGCTCTGAGCCCTGGA
AGGATCCCATATGGGCCGGCCGTTACACCATCTATACTCTGCCTCTTCTGGCCAC
CCTTTCTGCATCTTCCCTTTTCACCATCTAACCCTATATTAGGACTATTGACCCCA
TATTGGAAGGACTTTGGGACCATAGGCCTTAGATACACATTCTAGTTCCTGGGCT
TGGACCGCCATTTTGTCCTATGCTGCTGCCACTGCCACCACCAGTAAACCCAGCT
ACATTCCTCAAATACCAGGCATTTAAAACTCATTGTAGGGTTTCAGGGCCACCAC
TGGCCCTATCTGAGCCACCCATCTTTCCACAAGACCTGAATCACCTCCCTTCCAG
CCGCTGCAGAAAGAATGCCTATCAGTCTGCCCCTGGACTCCTTAAGGAGTTAGGA
ACAATGGGGAGGAGCCTTAGGCCTCAAAGGGACAATGACCAAACCAGACTTCCC
AGAGGCTATGGGCAAGCTCCTCAAAACTTGAAGGAAGTGGTCAAGGACACCTAT
GTGAGAGGACCTGCCCATGGCCACACTAGCCTCAGTGCTACTAGACATTCCTCCT
CACCAGATGGAAGAGACCTCATGCTGCCTAGCAATATTTGGGGGCTCTAGATGT
CCCCTGACCAATTCCATACTCCATGGTCAACCTCATCCCACCTATGGGCAGCCTC
CTTACCAAAGGAAGGCAAGCACAGCAGCTAGAATTTTCCTATCCCAACCCTGCC
ATTAAATCCTCAAAACAGTTTTACCTGTCTCCTTGTTCTTTTCTCCTTGCATCCAG
GATCATGAAGGAGAGACCTATTATTTCCCCACTTCCCACATTTGTTATTCAGGGTT
CTATAAAAGAACAGAACTGATAAAACATATACTAGAGTTGCTTAGAAGCTACAG
TCCAAATAGTCCAACAATGGCTACATATTTTGAGGAAACACCTGAAGCTGATGCT
AGAGCAGTCTCTTAATTTGAAATCTTCTGAGGGCTCAGTAGGACTGAGAAGTTTT
ATAACTGTTGCTTTATACCATGCAGTCATCTCATGCTGGCTTTGAAATCACAAAG
CTCCACCTGCTTCTGACTCCCAAGTGCCAGGCTTAAGGGTGTGTATCACACACTA
TAGAATATTTTTATTCTTTTCAGGCATGACAGTTACACTTCTTTTTGGGGTTTTTTT
TTTTGTGTTTTTGTTTTGTTTTGTTTTTTGTTTTTTTTGTTTTTTGAGACAGGGTTTC
TCTGTATAGCCCTGGCTGTCCTGGAACTCACTCTGTAGACCAGGCTAGCCTTGAA
TTCAGAAATCCGCCTGCCTCTGCCTCCCGGGTGGTGGGATTAAAGGTGTGCGCCA
CCATGCCCAGCTGACAGTTACACTTCTGGTCAGTGTCCTCCAGAGCATCCATCAA
GGTTCCATAGACAAGATTGGAGGCCAGGCTTTAACACAGGGACAGGCCCTTCAT
TCTCCATCCTCCTGGTGTCTATGCCTCAGATGGGTGAGCTGATGGTGCCACTTAG
ATTGGGCCTGAGAGCTGGCAGGGCAAATGTGTGCAACAACTCTGGGGCTAAAAG
CTGTGTGCTGAGCTATGGAGGCTTTCTAGCCTAGCCTCACCACTTTTACCACAGC
CCATGAAAAGCATGTAGAAACAAGTAGAATAGCTTCTCAGGGACTTGGCACAA
AGCCCATGTGAGGCCTCAATGCCACTTCCACTGTCATCTCCTACTGACTCTCATG
AATTTTAATCTTCCCATCATGTTTAGATAAAGGCCACACGGTTTCTCTTGACTCC
TGGTACAGCAGTCATGTGGTTACAGTGAATAGACAAGGTTTTACAAAAGGATAG
TGAAGATGTAAAGCCTGTCAACGCCCAAATGGCAGAATCTTGTCCATCTTTTCCT
AAAGCTGCCCCCACACCTTCCTCCACACATTACCAAGGGGTACCAGACTCATGCC

Figure 4 cont'd.
TGTTTTGGGAAAGAGCCTTTTAAAATCCTCAACCTCTTTGAATGGTTAGAGTGG
ATTTTCAAAGCCTCAGATGTTCACCTGAGGGTGGTATTTAAAGCTTTAGGGCAAG
GGAAAGCAGACAAAGGCACCAGAAAATGGTACTGACCATGTGGAGGCTCTTTGT
GCTTAGAGTACTGTTGAAACCCTCAGGTTGCACCCCAACTTTTACAGACTTTGGG
AGTAGAGAACTTGCTGGCATAGTGTCCCTAAAGCAGAAGCTACTATAAAGGGGC
AGCACAGGGAGCCTAAAGTACAGAAGGGACATGGGAGTAATTTGAGTAAGAAA
GAAGAAGGACTGAAGAGAGCAACCTGACCCTACACCAAAGCTCTATTGAGTACA
TTCTACTTTCACCTTACCTCTGGGTGTGTGTATGTATATGTATAGGGTGCCCTTAC
TAAACTCAGGTCCTTTGCAAGACCAGCAGGCACACCTAAGCACTAAGCCATTTCT
CCAGTACATTACGTTAGTTCTGATGCAAACATTAGTGCTGAGATTCATGGCCTAA
TCTGCAGAGATCAACTGACATAGAATCTCTATATGCCTACACTGGATGAAACCAG
AAACTTGTAGGTGGAACAGTCAACTGTAACCGCAGGTATTTGTAGCTACACTAGA
GTAGAGACATTTTAAGTCTGGGTTACATTAGCTGCCTCTGGATGAGAAACTATA
GTAGTACATGAAGGCCCAGGTGAAGTTGCCTTTCACCTTGGCTCCAGGTCCAAGC
GATAGCATTCAAGTGAAATCCAAGATTTTGGTCCCCACATTGGACAGAATGAAG
GAGTAAGTAAAGTCATTCAGCTACCACTTCAACTCTAGGACACAAAAACACAGG
TGGGGACACAACTGTTGCCTAAATCTTATTTAATACTAGGGTAAGGTAGGATAAC
ATAAAGCACAAAGAGAGGTGAGGACATTCAGCTGATCACTCAGATTTAAGTCCC
TACCAAGGACCAAAGGCACAATAAGCCAGCAGCATTTCAGGAATGATGACACAA
TCATTCAACAATGAGGCTGTTGAGGGAATCTTTCTGGAATAAGCCCTCTGACACC
AATGAGAGTAAAAGAGAAATGTCCCCAATAGGATGAAGCCAGGACAGCTCCTGA
AAGGCTTTAATGCTGGGTCTAATTTGTGAGCAGGTCTTTACAAAAGTATGCTTGG
CAGTCAGCATGTTGTTAAGAGCAATGACCCATTGTTTGAGCTATTTCTCCAGGTC
ATTCTGTTCCAGGGAGCAACTGAAGTCATGGTTGGCAAATAGGTAATACAGCAG
TGATATAAGTAAATCAGTAAATAAACCAATAAACCAGGACCTAATACTTGGTCTT
TTCTACCTTATTACTTTGGAGGCGTGACAAAAAGTTCAGCAGACAGTAAAAGCCA
CCTCAGCTCCATGTAATCACACAAATCAGAAATGAAGGTCCAAGTGATAGCATTC
AACTGAAATCCAAGATTTTGGTCCCTACACTGAGCAGAATGAGGGAGGAAGTGA
AGTCATTCAGCTGCCACTTCAACTCTGGGACACAAAAACACAGGTGGGGACACC
TAGGATCTTATTTAATACTAGAATAAAAACAAAAGATGAAGACAGTCCACTGTC
ATCTCAGCTTTGAGGGTCACACCTATCACCCCAGCCCTAGAGAGGTAGAGGCAG
AAAGATAAAAGTTCAAGGATATCCTTAGCTATATAGCAAGGTGAAAGCCAGCC
TGAGAAACATAAGCATCCCATCTCAGAATTTGAAATGAAGACTGGCAATCTGAA
TAGGAATGGCCACCATACATTCATGTATTTGAATGCTTGGCCATATAGTGGCTCT
ATTAGTAGGTGTGGCCTTGTTGGAAGAAGTATGTCACTGTGGGGAGGGCTTCCA
GGTTTCATATATGTTCAGGCTACACTTAGTGTAGTGCACAGTCTCTTCTCTCTCCC
CCAGCACTGTGTCTGCCATGATAATGGACTGAATCTCTGAACCCATAAGCCAGCC
CCAATTAAATGTTGTTCTTTATAAGAGTTGCCTTGATTATGGTGTCTGTTCACTGC
AGTAAACCTCAAACTAAGACATTGATATAAAGGTAATTCACTGCATTAGCTCTGA
GAATAGATCTGGAGACTTTGATAAACACTAAAGTGTTAGGAGCCATCTAGGATA
GGCTAAGGCTAGCAGGTGGCCTTCCTGGAGGTGGCCCACCGTTTTTGCATGGTC
TGCTATTGGTGATCTTGATGGCAAGGTTCCAAAGAGACTTCATCTCAGGATTGCT
TCTTGCAGCTGATATGTCTTTCCTGTCATTATTAAATTAATATAATAATCCTCAGC
ATTAGCCCACCCTGTTGATCAGATTTCCTACATATTGAAGTAAAGATGAACTTTC
ATGAATTAATGCTATTTAAATTAATTAATGATTCTACAGAATATCTGATTTGATTC
AAATAATCTTAGAAAGAGTTTTAAAAGATGGTTTCAGTCATTTTGCTAAAAAGAT
GCAATAAAGTAAGAATCAAGAATAGAATGTGCCCACTCCTCATAATAGTAAAGG
GTGCATAATAAGAAATACAATGAGCTTTCATAATTACACTAAAAAGAGAAATAG

Figure 4 cont'd.
GCTTGGGATAAATTTGTGTTCAAGGAAATGCATTTAAGCCCAAGGATGGAGCCA
CAGGTGTGCACTATGATAAGACAAGGCCATGTGAAAACTGTGGCTTTGAACTTAT
AATGAGCATATAGAATGAAACACTGCTTTGATCTTAATTTCAACATCCTTCTGTA
ACTCCCATTTTATCTAACATTTTATCTCTGAAGTAATTTTCTAAAGAACATTTTGT
CTAAGAAAGTATAAAAGGCCAGAGAAAGGAAAGAAAATTGTTGGTTTGATGGT
TTGGTTTGGGGAGCTCTGCCCCATCTATCCATCCACCCATCCATCCAAATGTGTAT
ATCTGTTTGTCTATATGTAAGTGTGTAGGTAACTATGTATGTGTAGGCATGCAT
AAATACTTGTGGAGATGATTGTGACTGATGGTCAGGCCTGGCCAGAGTGTGGAT
GATGAATATATGTGTCTGTGCATATTTGCCTGTATAAAGCATTTTGATTCTTTC
CTTTCCTTCCTCTCTGGTTCACAAAGAGTTAAGCAGCCTAGCCATGGAGGCTTCT
GGCTGCCTGGACAGAGAAGGAGCACTAGCAATAAATCCTTTTAGTTAATTCCCT
GACACTAAACAGCATGTGTTAATCACCAGATATTAGTGCTTATTTAAGCACAAGT
AAGTAAGAGTTAAGTTTTTAGCACAAAACTAATAGTTGTTACCCCAGAGCTTAAA
GAAGCACAGAACAGTAAAGAAAAGTTAAGTTTTTAGCACTTAATGAAGCACAGA
ACAAAAACAGAGTTATAAAATAAAGATACAGCATTTAATAAAGCATAGAGATTT
ATAAAGAAAAAGGAAGCTACAGAGAGTTAAAGAGAAAAGAAGCCAGCAGTTTT
CAACCACAGAATAAACAAGAGACTGTTAAGTCTACAAAGCCATCAACAAATATT
CAGTAAGTATAGTTAGAGAGCTAGGCTAGAGACCATCTGTCTTTAAATCTATGTC
CAATGCTCTGTCCCATTTCAAGCCATTCCAGGCCAGTCTGGCTCCCGACATCTAA
ATAAGATTGGAAATTAGAAATAACGAGTAGTAGAAGGTGTTACTTAATGATTCT
GTTTGTTTCATTTAACTGCATTTTTTCAGTGTACTTTGTTTTGTTGCTGTTGTTTTT
GAGATAGGGTTTCATAAAGCCAGGCTGGCCTCAAACTTGCTATGTGATAGCGGA
CGACTCTGAACTCCTGACCCTCCTACCTCGCTCTTAATCATTGGTTCTCAACCTGT
GGGTCATTCCCCCTTTGGGGGTCACATATTAGATATCTTGCATATCTGATATTTAT
ATTATGATTCATAACAGTGGCAAAATTAGTTATGAATTACCAATACAATTATTTT
ATGGTCAGCACAATATGAGGAAACATATTAAAGGGTGGCAGCATTAGGAATGTT
GAGAACAGGTTTTTTGTTATTGTTTGTTTTTGGAGGTGGGTTTGGGTTTGGGTTT
TTGTTTGTTTTTTGGGAGGACTTGGGATTCATGAGATTCTATCTTAGATATAATG
AAATAAATAAGAATACACGGGCTTGTAGGTAGCTTGGTTCCTTCATTCTGTGTAA
ATGTGGATGTGTGGTCCTGATCCCATAAGAGGGGGCCAAGGAGCCTGTATTGGT
GGGGTCTGTGATTCTTGGCCCTCAATCCTATCAAATAGCCCCAAGAACCTCTAAA
ATAGGCTAAGCAACAATTCATTCATCCCAGGGTATAAGTTTTCAGAATCTCAAAG
TAAAATTGCCTGGCTAAGGGATGCTGAAATGCTCAGCAGGTAAAATCAGTTGCA
TCAAATGCAAGTCTGACAGAACAACACAAGCACAATGACCCAAAAGTTGTATTC
TTCCTTCACATGTATATCATACCATGTACACATACCCACATATACACATATTATAT
ATGCATACATAATAAAAATGTTAAGTGCCCAGCTGAAGAGTCAGCCCTGATGAC
TCATGCCTGTAATCTCATCACTAAGAAGACTGGTTCCTGAAGACTGCCAAAGTTC
TAGTCCAGCCTGGACACATGGTGAGTTTTAACCTAACCTGGCATACAATAAAGAA
ACAAGCTATCTGAAAACAAAATGTCTGGCTGAGTGAAGTATTTTATACCAGTATC
CCTGGTACTCTGGAGGCAGATACAAGAGGATCAGATCAATAGGACCTTGTCACA
AAAAACTGAGAACTAGACCAGAGAGATGGTTCAGTGGCTATAGGCACCTGTTGC
CCAGCTCAATGACCTCACTTTGATCTCTGAAACCCACATGATGGAAGGAGAAAA
AAAAAAACACCTTCAACTTGTCCTTTGATCTCTGCATATACACTGCACACTGTGG
CATGTACATGCCTGCACATGCCCTCCACACACACATATATATATATATAAAT
GCATACATAAAATTCAAAAGAATAAAAACTAAGGATATATATATAAATACA
TACATAAAATTCAAAAGAATAAAAACTAAGGATAGCTCAAAACTTACCTAGAA
TTTACCTAGCATGCCCTTGACCTAGATCAGATCTCTGACACTGAAAAAATGGAGA
GGCAGGTAACCCTCTGGTTAAAAAAATCAGAGAGAAGCCGGGCAGTGGTGGCGC

Figure 4 cont'd.
ACGCCTTTAATCCCAGCACTTGGGAAGCAGAGGCAAGCGGATTTCTGAGTTCAA
GGCCAGCCTGATCTACAAAGTGAGTTCCAGGACAGCAGGGGCTGTACAGAGAAA
CCCTGTCTCGAAAAACCAACACACACACACATCAGAGAGAAAGAGAGCTGGG
CTTTGTAGCACATGCCTTTAATTCCCCACTCTGGAAGCAAAGGTACACAGATCT
CTGAGTTCAAGGCCAGTCTGGTCTATATAGCAAGCTCCAGGCCAATAAAGACAT
AGTGAGACCTTGTCACCCTCAAAAAAATTTAAATAAGAGGGAAAATATCATTAA
AAATAGAAAGATAATTGTTTTGGTTTTTGTTGTTTGTTGTACTGTCTATTGATTAT
ATAACATCCTAAGCCCTTTTTACATTTTTGTTTTGTTTTGTGTTTTAAGACAGGC
ACTATATAGCTCTGGGTATCCTGGAACTCAGAGATCCACCCAGCCTTTGCCTCTC
AAGTGCTGAAAATAAAGGCAGGTACCACCCAGGCTCCTTCTAAACTTTATTTTGA
TACATGGTCTCACTAAATTGTCCAGGCTGGCACTGAACTTGTGATTCTCCCACCTC
AGCCACCTATGTAGCTGGAGTTATAGGCCTGCATCAGGCTTATCTAGAAAACATA
GTTTCTAAAACAAAAAGAATACCAGGCATGATGATGTTAATCTCTAGTCTTATCG
CTCTGGAGGCCAAAAGCAATAGAATTAATGCAAGTTTGGAATTAATGCCTACTCT
ACATAGAGAGTTCTAGGCCAGCCAGGGCTATAATGAAAACCCGTTACAAAAGCA
AAAAAACAGAGCCAATGAGAGGAGCCAGCTGATAAAGATGCCTACTGCCAAGTC
TGATGGCCTGAATTCAATTCATAGGCCCCACGTTTGAAAGAAAAAACTGACTCCT
ACAAAATGCCCGCAGACCTCCACAAGAGTATTATTATGCCACTCCAGTGCATATA
AGCATACAAAATCACAAGATAGACATACTTCCAGATAATAGATAACATATAATA
AAATAATTTTCTTTAAAAAGCAAGGGCATGTCTTTTGGGATCATTTTCCTCCTAC
TGGGTGGCCTCATCACACCTTTCTACAAGGCAAAGTGTCTAGTCTTACTGGAACA
TGATATGCCATGGCTGTTTGATATCCATGGGAGCCCTACCCTTTTCTGGAGGAGT
GGATAGGAAGGGGGTCAGATGAGAAGTGGTGGGCATTGGGAGGAGAGGAGGAA
GGGAAACTTCGGAGGTGGAAGCAAGAAGATTGGGAGTTCATAACCATCCTTCTT
AACTACATAGCCATCCCTCTTCACTTGGAATGGAAGTTTTGTTTATTTAATGTCAT
AGATACAGAAAGCAAATCAAGGGGTTGCCAGAACTGGATTTTAATAGAGTCGGA
GAAAATAAATGTTCTAAATACCATAAATTCTATACTTTAAAATGGTAAATGTCAT
GACATATTAATGAAACATCTAATAAAGCTGTTATTTACAAAGGAAAAGGCTAGA
TTTCTGCCCCTCAAAAATGAAAGTTTGGGGCTGGAGAAATGGCTTAGTCAATTAA
GAACATTTGTGGATCTTCCAAAGAGTTGGAGTTCAATCCCCAGCATCCTCAAGGT
GGCTCACAACTGTCTATAATGCCAGTCCCAGAGGACCTGATACCCTTTTCTGGCC
ACTGTAGGCATGGTACCCGTGTGGCACACAGACATACACTCAGGCAAAACACCC
ATACACATACAATTTTTAAAAGGATGCCAGGCATGATGACATACACCTTTAATCC
TAGTATTTGGAAGATAGAGGTATGCCTCTTTTTTGTGAATGAGGATAGCCTGGTC
TACATAGTGAGTTCCAGGCCAACCAGGGATACCTAGTAAAACCCTGGAGAGAGG
GAAAGGGAGGGATGGAAGAGAAAGGAAAGAAGGAAGACTGGAAAATAAATAA
AGGGGAAATCTCAAATGAAAGTATGTCCTCTGGGGTTCTATCAGTGCCCACATAT
TCTTCTATAGAGGTAACTTGCACATCCTAGAGGTATAGCATTCTGAATTCATGGG
TCACTGACACCTATCAGCTTGCATTCAGAAGGAGCCCCTAGAACAGAGGATATG
CAGAGTCAGCACCCCCTTGCTTACTACATTGCTAATAATTTGTCCCATCCAACTTT
ATATACCTAAGATCACAAATGCATACTCATCAGTATTTTTTTTTTTTTGGTTTT
TTGAGACAGGGTTTCTCTGTGTAGCCTTGGCTGTCCTGGAACTCACTTTGTAGACC
AGGCTAACCTCGAACACAGAAATCCGCCTGCCTCTGCCTCCCAAGGACTGGGATT
AAAGGCGTGAGCCAGCACACAGCACACCCAGCTAGTAATTTTAAGATGACAAGA
TGTCACATCAAGTATGTAGTCCTAAGCACAGGGTCCTGGATGACCCTGCAGGACA
CTAAAGTATAGGTATAACTTTTCCTTAACCTACTTTAGTAAGGGTTCAACCTCCCC
TCTAGCCCACCATCCACTAGAGGTGAAAAGAAAGTTTAGGAGGATATGGGGTA
AGTAGAACTGTTTAGAAATAGTTCTTTGGGGAGATTCCAATCTTCATTGTCAGTA

Figure 4 cont'd.
GCCTTGTCCTCTACCATAACACCAACATGAATCAGCAGCTGCAGTCCAGTTCACT
TGGCAATCACCACTCATGAGTCAGCAAGAGCAGTTCAATTCAGAAGAAACTGCA
AGGCTCACCAATCAGCTCGAGTCTGCAGAAGAAACCGCAGGAACCTCATGAGAA
GTTCTCTATGAAGTCACCACAAATAAAGCTCAGCAATGCAATGTATGGCAAACC
AATACATGTGTATCGTCAGCAAAGACTACCAAGGCAGAGCAAGGCAAACCAATG
TTCTAGCTCCCATTGTCTGTGTGGTCATATGTATATTCTTTCTAAACATCACGTGT
CCTTTCACATGCCTACTATAGCAAAACATCCTCTCACCTGTGTCTGCTTCCGAAAA
CATTTTCACATGTCTCCCTTGGCAAAACATCCTTTGACCTGTGTGCCCCAGCAAA
GCATCATTTGACATAACTGACTTTCCAACGAAACCAGAAGTTTCCACTTCAAAAA
AAACATCAAACCTGACCTCACTCTTCAGACTAAACCTCAGGCACACACAGCTCTA
CAACTTGCATCCACATATTCACATATGTCTAACAATGTGTCACATCTCCAGTAAA
CCATCACAGTACAAAAGAGTACAGCGGATGCTTTCCTGCTCCCACCCTTCCTCAA
CCCAGATGTGTCTCACTGCTGGAACTGAGCCACCAAGCAATTACAGGTAGAAAA
GGTCAAAACCCCAGCTTGATCTGGCCTGCCTGCTGAGGAGCCAGAGGGCATAGG
AGGACCAGAAAGACAGAGATACAGCTGGGGAGAGCCTTTGAGACTTTTTGGACT
TTGAGAAGCAACCAGAACGGATCATCCTTCCTTTTCTGACAGAACCTCCAGAATC
CTCCCTCTAAAAGCCATGTATGGCACATGCCTCTGAGCTCAGCACTTCACAAGTC
CTGGCCGTAGGAATCATGAGTTGAAGGGCAGCGTCAGCTATATAGCACATTTAA
GAACAGCTGGGAAACATGAAAGACCATCTCTCAAAACAAACAATACCAAAAATA
ATTCACCATGATGTTACTGTAAGAATGTAATGTTAGAACTCAGACCAAACTACTG
CTCATGCCCACAAAGCCTGAAGCAGCCCTTCCATTCCCACAGATACTGACAGGCC
CCCTACTGAAGGCATTTTCTATTAGTGCCTTACAGACTTCCAGGTGCACCACACA
TCCTGGTCCCCACCTCCTTCTATCTTGAGTTCTATCTTAAAACCAAAGAACCTTGC
TGCAAGCTGGTACTATAAACCATCCCTCTTCCTCAGAGAGCTATAAGACAGGACT
TTGACACTGCCTGGAGAGCTCTTACTCCTCTTTGGAAGCCCTGTTTCTGGTGCTGA
GGCCTGGACTCTCCTCAGATCCCTGCCATGCTGCTGTCTCTTTGTCCAGAATATT
AATAATTCTTCTAATAAGTTTCTTACCCCCACCAAAAAATATCTATCCCAGTGTCT
CTCTTCAACATGCATCCAAGACCTCTCAGTTACCAGTTTCTGAGTGAAACTGGGT
CATTTTCTTTCCAGAATCATAGCCCCAGTGACAAAACTGTGAACTGATTATGCAG
TGATGGAAAGGTTCCCCTTTGGCCAGAGAATAAGAAATCAGGAGAAAGTGTTCA
CAGACCAGCTTCCTGTCTGAGCAGAAGGCCAAACTGGAAATGCTATTAAGTAAC
AAGTAAGATGACTATCCAAGACTTCTTCAGGAAAAGAATAAACAGGTCTAAATA
GAGTCCTCTATGGCTGAAACCAGTTTTATCCTATTCCACCCTTCTCTGTTTTCACA
ACTAAAGTCAAAATATGGAGTGTCTGTATGAATGGCTAGCACTTTGTCTACTAGC
AGAAAAGACTGCCTTCCTGAGATGAAAGGCTATTTCCCTGATGGCACTTGTTCTC
TGGGTTAAACAGAGTTTACCTATGTCACATAACAGGTTACCTATGTCACATAAAA
CTGTGATCAAATAAATTAAGGATTTTCTCTTCTCAATCTTCTTTTTTACTTTACTCA
GCATCAGTTACTATATTAAGAATCTGAGCCGGGCGTGGTGGCACACGCCTTTAAT
CCCAGCACTTGGGAGGCAGAGGCAGGCGGATCTCTGAGTTCGAAGCCAGCCTGG
TCTACAAAGTGAGTTCCAGGACAGCCAGGGCTATACAGAGAAACCCTGTCTCGA
AAAACCAAAAAAAAAAATCTGTTTTATTATTGTTCTGAGACCGGGGTCAGTAA
ATGTAGCTCAAGCTGCCCTGGAGGGTAGCTCTCCTGCCTAGGCTTCCCAAGTGCT
GGGATCATAAGCATGCACACATGGCTTTAACATAAAGGTATTGTCGTTACTGTTG
TTTTGTTGGGTTTCTTTTTTATTTTGTGTGTATATGTGAGCACCTACATAGATGTA
TGCGTACCATGTGTATGTCTAGTGCCTGAGGACATCAGAAGAGGAAGGATATCA
GTTTCCTGGAATTAGAATTATAAGTGGATATGAGCTACCATGTGAATACTAGGAA
CCAAACCAAACAGGTCTGTGACCTTTTTTTAATCTTATTTTAATGATGGTTCTT
AAACTCTTTAACCTCCCTTTTAGCCCAATACTCACCAGAGGGAAAGAAAGGATAT

Figure 4 cont'd.
GGGGAAAGTAGACCTGTTTAGAAAGATTCTTTGGAGCAACTCCCGTCTGTGTTGT
CTAGAAATCAGCAGTTCAGTTCACGTGTTAGCAGACAGCTCAATCCACTCGCAAA
CACTTCATGGATACACCAACAGTCCAGAGTAGGGATAGCAAACATGAATCAGCA
GCGGTGACACAACCTAGCAGAGACAGCCAGGCCTCAGCCTCTGCACAAGTCAGC
AAGAGGGACGGACCCCAGAAGAACACCAAAAGAAGTTCTCGGATGTGCCTCTCT
CAGCAAAGCAAAGATCAGTGAGACCAACAAGCATTACATAGCCAGCTCTATAAG
CACACCTAGCTCAGCCTCTGTCACTGTCTATTGGGTCCTATTTATACCCTCCAAAC
ATCATGTGTCCTCCAGGGCTTGCCTCAGCACATGCATCTGTCTCAGCTGACATCA
CTCTGCCAATCAGCCTGAATCTGAAGAAGCGGCAAGAAACTGTAGCACACCACC
AGAAATTTCTCTCTATGGAGTCCTGACAAATACAGCTCAACTACACAACATAAGG
CAGACCAATACATGTATCATTTGCAAAGAATCCCTCATCATGTGTCCTTTCATGT
GCCTGCTTTAGTGAACATCCTCTCCTGTGTCTGCTTCAGCTAAACATTCCTTCA
CGAGTCTCCCTTAGCCTTTCACGTATGTCCACTTCAGCTAAATGTTCCTTCACATA
TTTGCCCCAGAAAAACACCATCCAACCTTAAGTTTTCACTTCACCAGTCCTCTGA
AAGAGCAGTAAGTGATTTATCCTCTGGGCCATCTCTCCAGCCCTCTGGTTTGGTT
TGGTTTGGTTTGGTTTGGTTTGGTTTGGTTTGGTTTGAGACAGGACTTTACTATGG
ATCTCAGAATGCTGGCATTGGACTTATGTTATTGTATACCCAAGGAGGGCCTCAA
ATTTGTAGTCATCCTCCTGCCTTAGCCTCCCAAGTACTGGGATTACAGGCATATA
AACAACACCTAGTTTTTTCTATCAGCTTAAAAACCTCCCAAACTAGGATGCATTA
CAGTCTTTTAGGACACTACATAGAACATATTGACTAGGTTCCAAATACAATACTT
TTAGGGGTAGGGATGTAGTTCAGTTGATAGAGTGTAGTTCATGAAGCCCTATAGG
TCCCATTTCTAGCGATACATAAAACTAAATGTAGTGGCACACTACTGCGATCTCA
ACATGTATGAGGTGGAGGCAGGAGAATCAGAAGTTCAAAGGGGAGGGGAGGGA
GAGAGGTAGGAATGAAGAAGAAAGAAAGTTAGCTACAGGTTTTCAATATTCCTT
GAAGAATGCACGTGCGCGCACACACACAATGTTATTCAAGTTGTCTTTTAATGAT
ACAAACATGAAATCTTTAAAAACAAAGATGGGGTTTTAAAAACACCAATACTTA
ATACGACAGCATTTAGCTAACTTCCCTGCCCTGTTCAATCTGGACAGAGCACAGT
GGCTTTCTAAAGCTACATGTAGAATCTCACATATATTTTGTTTGCCCAACCAAA
ATATCAACAAAAGTGAAATATTTAGAGGTTTGGTCTGAAGAGATTTCTCATTGAT
AAGAGTATGTATTGCCTTTTCAGAGGACCCAGGCTCAGTTCCCAGCACCCACATA
ACAGCTCAGAAACATCTGTAACTCCAGCTCGAGGGAATGCAACACCTTCTTCTGG
CCTCCAAAAGCACCAAGTATAGACGTGGTGCACAGACATACACGCAGGCAAAAC
AGCCATGCACATAAAATAAAACAAATAAAATAAATTTAAAATTTAAAAATTAAT
AAAATTTATCTGTCAAATGTTGAAAATGTGGACTAGAGCCAGATATGCTGTCATA
TCCTATAATCCCAGCATTTAAGAAACAGAGACAGGGGGGCTGGAGAGATGGCTC
AGCGGTTAAGAGCGCCGACTGCTCTTCCAAAGGTTCTGAGTTCAAATCCCAGCAA
CCACATGGTGGCTCACAACCATCCGTAATGAGATCTGGTGCCCTGTTCTGGAGTG
TCTGAAGACAGCTACAGTGTATACAATAAATAAATAAATAAATAAATAAATAAA
TAAAAAGAAACAGAGACAGGAGAACATGGAGTTCAAGGTTATCTTTGCATGCAC
AGTAAGTGTGAGCCTTTTGTGTTCACTTCACTCTGATTTCATTACATGTATTTAA
AGTTAGTGTGCATGTGTGCAGATACAGGTGTCATAGTGAAGAGACACAAGGTAA
CCCACCCTTGTCTCTGTGCGCTGAGTCTCTCACTCCCTAGTCCCCATGCCAAGTTA
AACAGCCAGCACTCCCACCTTGGTGCAGATGTCCCCTACCTTTGAAGGAGGCAG
AAAATTAATGCCCTTGAAGTGATAAGGCTCCCATTCTTGAGCTATCAGAAAGAGG
CAACCGAGTGTTCCCAGACAGCTATGGCCAGCTTGTAAAAATACACTAGCCTCTG
ATTACAGAATGAGTTATTTCTCCCCAGGTCAAAAAGATCCTTTTCCAGATGTATC
AAACAAACATCAGTTTTGAAGGATAGCATTCCTTTACTGCCTATCATGTAATGCC
AAGACTTGAATGCCCCAGCTTATGCATCTCATTCATATATATATATGTGAATATA

Figure 4 cont'd.
ATTTAACCATTTAATTGTATTTTTTCCAAGACAGGGTTTTTCTATGTAGCCCTGGT
TGTCCTAGAACTCACTCTGTAGACCAGGCTAGCCTCAAACTCACAGAGATTCACC
TGCCCCTGTCTCCAGAATACTGGGATTAAAGGCATGTGCCACCATCCCTAGCTTT
AATTGTCCATTTTAAATGATAAAGGGCTGAGGTTTTGTGTCAGCCATAAGGCATA
TGTATGTCAAAAGCCATAAATTTAATTTTCAGAACACACACACAAAGTCCTGG
AGAAAATAGACTGAAAGTTTGTCCCATGAGTCATAAAAGACCTGGATCTCCACCT
ATAATCCCAGAACTAAGTAGGTATAAGCAAGAGGTCCAAGGACATCCTTGGAAA
CATAGTGAGTTAAAGAATATACGAAATTCCCATCTCAAAAAATATGTAGCAGGA
CTGGGTGTGTTAGCATACGCCTTTAATTCCATCATTCAGAAGGCATTTAATTCCAT
CATTCTGTACATTTGAGGCCAGCCTGGTCTACAGATGCCCTTGACCACAAGCATT
GGAGAGTGCCTATGAGGAAGTACTCAGTCAATATGGAAACTACTGTATTCTTTTT
TTTTTAATATTCATTTTGTTGTTGTTGCTGTTACTATTTTATCTTTACTTAATGTTTT
ATTTTAAAAATTAATTATTATTTGTGTGTGTGTGGAGGAGGAGGAGGAGGAAG
AGGAGGAAGAGATCAGAGAGGTGCCAGATCCCCTGAAGCGGTTGTGAGCTGCCT
TATGTGAGTGTAAGGAATCCAGCCCGGGTATCCTGCAAGAACAGTATGTGCCCTT
AACCACTGAGTCATCTCTCCAGCTTCCTACAATTTTTGAAATTTTATTTTTTTTATA
TAAGTGGTTTCCCTACATGTACCACATGTGGTACGTGTACCACATGCATGCCTGG
CGCCTGAGATGGTCAGAATAAGACATCAGATTCCCTGAGACAGGTTTCATGCAG
CTAAGGCTGACCTCAAAGTTGCTAAGTGGCCGAGGATGCTTTAAACCCTTTATCC
TCCTCTCCCGTCTCCACTTTCCAAGTGCTGAGATTACAAGTGTAACCAAATTGAA
AACGCTATCATCTAACCAAAACAGTGCTTCTGTAAACTTTTCTGTATTTTGGAGC
ATTATGGAAGTGGGGTGGAGTTCCTGTAAGTAAGACCATTGGGTCAAAGGACAG
GAATGCAGCTGCCTGAGACACAGATAGATCCAGCTTAAAAGGACTGGCCCAGCT
GCCCTGGCACTGTAGGCGGTCAGGGGAAAAGGCTCAAACATGAGGGTCAGGAGC
AATGTTCCAAACATCCCTTCACTGATTGATACATAAAACAGAACGCTCTCACGAA
AGAACACTAAGCAGAAAGAAAGCAACCAAAGGCTCAGGTTTACCTCCGCATGTG
CTTCTGAACCGTCCATGCTCTTAAAGAACACATATCAACCTTAAGTCATTATCTGT
GTCCCCGCATCCATCCTCTTATGAGCCATGAAAGCTCTGATATCAAGTCACAATC
GGAGCTTCAGCTCATCAAATATAGAAATAGATCGCTCACCTAAGAGGACGTGTG
GAGGAAGTGGGAATGGGGGCTCTGGTGTTTTATGCCCGTAATTCCAACATTTGAG
AGCCTGAAGCAGGTGAATCGCTCCAAGTTTGAGAACAGCCTGGGTTACATAGAG
TTAAGCAAACATGAACTGTAAAGTGTATAGTACCTCAAAGTCTAGAAGGAGATT
TCATCTTGAAGCAGTGACACTGTAGGAAGCTAGGCGGCTCAGCTTTAGCACAAG
AGGAGTGCACAGCCACACTCGGCACCTCCCACCCAGCCTCTGGAGGAGAGGGAG
GAGGCCGGTCTGGAGGTGGAGCCTCCGTGAGGACCTGCGGACCTACAGCACAGC
CTATGGGCCTATGGCGGAGCGACGCCTGTGGGCTGTGGCCTTCTGCGGGCGGCCA
TTGTCGTGCCTGATAAGCTTTTCTACGTGACTCACTTGCTTCACCTAGCCGGCAGA
GCGAGACAACTGGGTAACTCCCTGATCCGGTCTGCTTCTCCCTACACCCAGACAA
CATCCTTGGCCCGCCCAATCTCTGCCACCAGCCTCGAGCGGATCGACCTGAGCCC
CGGGCCTAGCACCGGAGGGATCCGGGTGGAGAAGAATCATTGCTACGCTCCAGT
CCTGGAGTCTGTTAGCCAGACTGTGAGGCGCAACGGATTCCTAAGGCTCTCCTGG
CCAGGCAGGACTTCTCCCAGCACTCACGAGGAACTGAGCCTGGACTGGTGTTTGG
AGGAACAAGTCATAACACCGATCGCTCCCAGCACAGACTTGCCACTGCCCCCAC
CCCCAAACCTACTCTCTCCTGTTTCATTCCCCCCAGAACCCACAGTTCCCAAACA
GTGCACCTGCGGGAGATCTCAACCCAGCTGGAGAAGTGGACATGAGGTTGGCAG
GTGGGTGGCTTCCACAGCGAACTGAAGAGAGGCCAGGTGTCCTAGTGCCTGTGTT
AGGAGAGGCCTGGGTGGTCACTGGTTTGTTTATTTATTAATGGATGACTGTGCAC
AAGCACTCATTTTATGAGCAAATTCACCTCTGAGGACTTCAGCTTCCCAAACTAT

Figure 4 cont'd.
AAGGATTGATTTTATATAGAGAGATAGATATAGATAGATGTTGATAATATATATA
ATCAATATATATAAGTTAAGGATATATATATATATATATATATATAAAATCTCCA
GAGATTGAATGGATGGAGAGGAGTGGATAGTAGAGATAGAGAGATGTAGCCAG
AAGAGAACTGACTTAGGTGCCTTTGAGGTTGGGTATGATCTAAGTGGTAGCTCTG
CTGTCAGCTGGACTACAAACATGAATGTGCCTTGGAGGGACTGTTTGGGGTGAG
AGTAGAATTTGAAAACTGGTAAAGTAGCAGCTTTGTGGATAAGTCCAAATTGGA
CATTAAGGAACTGGCTGGGAGGATATGAGTTCAAGACAGATCTGGGCTGGAGGT
GTAAGGTGTCATTGCTGCATGGTGAAATCTCCCATACAGTATGAAGATGGGAGA
AGGCAGCCTGGAAAAGAACACCTTTTGAGGAGAGAGTAATGGAACACAATCTAA
CCAACAAAGGGAGTCCCAGAGAATGGGGTCAGGAGACAGTACTGTCCTGGAATC
TAGTAGTGAAGTGTCAAGAAGAGCAGTCAGACAATCAGAAATGTGACATCATA
AAAGTCATAGGTGGTCTTGTTGGAAGGTTATTTAGTTGGTGTTATGGGAGCACG
ACTAGATTGGAAGAATTTTGGGAGAGAGTTGGGGAGTGAGGTAATAGAAATCAC
AATGTAGATGACTTTTATGTGTATGCTGGGGATGGAAACCAGGGTCTTATGCAT
GCTGAGCAAATGCTCTACCACAGAGCTATATCCCAAGCCAGAATATAAATTTTA
AAGAGTTTGGTGGAGAAGAGGAAGATGAAGAATCAAAGAATGAGATTTTTCTTT
CAGGAGCTCTGTTTCATCTTTATCTTACTAAGTTAGGACCTGTTGATAATATGAGA
GAAAGTGAGATAGAAAGAAGTCTTAGCACAATGTATCTGAGACAGGAGATATCT
TGATGGATCCTGAAGCAGGTAGAAGGACTGGTCTTTACAAGGAGTATAGAGCTT
CCAACAGAACAAGAGGAAAGGCAAAGCAGATGGGTGAACTGTAAATATTCTGAT
AATTTCAGAGGCAAGATGCTGAGGTTGGTGCTATGAAACCTTCCAGAGCATGA
GTTCTAAAAGGCACCTCCAAACCTGCTGGGGAGACCCAAACAGAGCAGCCTCAA
GGTTTGAACTCACGTTCTTCCGTCTACTAGGAGGAAGTTCAAGCCTCTCTTTTGGG
TCTGGTAGATATCGATTGGTCCCCCACCTCCCAATCGTACCATCACTTGTTCCCAA
GTAGAAGGGGAGATCTGGTCATGTGAGGTAGTGGGTTATTGCAGATTTGTTCAC
TGATGTCTAAGATAGTCCTGCTCTGTGTCTATCCTGCCTGCAGGCCCCTGCGCAT
CGTGGCCCTAATCATCATTATGGGTCTCACCTGGATCCTAGTCACCATCCTCCTAG
GTGGTCCTGGTGTTGGCCTTCCTCGAATTCAGCAGTTCTTCACCAGTGAGTGTGG
GAATCCTCTTGATTCACTATAGAGGCGCCCAATATGGGTTATGGTGGTTGGGTTT
CCCATTACCTTCATGGCAGGCTTCCTTTTGCCCTAGGTCTATCTTCTAACACAAAT
GCATCCTTGTTTCCACGAACCATCCTAGAGAACAACACTCCTAATTGTAACCAAT
AGAGTGGAAGTTGATAGAGTAAGAGTAAGGAGTGGAAAGGCCTCCATTGATTAT
TAATCATCTTCGACTTTCCGTTGAGCTCTGAGACACACAAGGGATCTTGCACTTT
GTCACTGGTGCCAAGTCACCTAAGCACTATTTACAATTCCAATTCATCCTTTTCCT
GAAGCAGGCAGTTTTATATCAGGGCATCATTGAAACTTGAGCGGGGAACATGCC
AAGTATAGCCTGACTTGGCCCTGAGTCCCTGAGCCTGGTTGTTCTGCTGGAGGCT
CCTGGAGGCCTCCCTGCTAACAGAAAAAACTCTCTACTTACAGGCCCAGAGAAC
TCAGTGACTGCAGGTAAGCCTCCTGTCCCTTCCCTATTCCCCCGTACCTGTACTT
CAGACTGCCTTTTGTGACACCCCTGCATGCTGTCAGCCAGCCCCACTAGGATCTC
CATTCTCTGTCTGGCCTCTCCCAACTAACTATCATAGGCTTCTGGGCTGTAAACCT
AATAAATGAGTTAGCCACCATCAGAAGATGAAAGGGGCAGGCATAGGAAAAAA
ACATTCCCATTCCAAACAAGAGACATTGGGATGAAGCAGGGGCTCATGGTCCTA
AGCAAGTCCCAATCATAGCAGGGCAAGTTCTAGATGTCAAGGCCTAAGAAGAAA
TCTCTATATCATTCTCTAGGCCCACTGAAGTGACTGCATCCTCTGTTCCCTCTTTG
GCCTCTTCATTCCTAGCTCTGTATTCAAAATCAACCTACCTACCTCCCACCCTTCC
TTCCTTTCTCCCTCCTTTCTCTCTTCCCTCACTTCCTTCTTTCTTTCCTTCCTTTTGT
CTTTCATTCCTTTGTTTCTTCCATCCTTGTATTCTCATCTCAGTTCTTCTCATAGGC
TGACAATATTTCTGTTGGTATAAATCTCTAGCAAATTTTGCTGGCCTCTCATGCAG

Figure 4 cont'd.
TTCCTGAAGGCCTAGGTTATAAGACAAGACAATCCTCCACAGATCCATTCTGTAT
AATCCTATCTCAAGTCCAGGCTTCTGAGAGGTAGGAGCACACACAATCATGTG
CTTCATTTCCTTAGCAAGTTCTTAGCGAGCCATCATCTCTGTGTTCTCTCTAAAGG
ATGCTTTTTAAACGTTTTATAGTGCTGGGAATTAAACCCAGGACCTTACACATA
CCGAGCAAATACTCTATACAGAGCTATTTTTCTAGCCCATAAAATGTTTCCGGTTT
TTTGACAGAGTTTTACTCTATAATACAAACTGACCTTGAACTTACTATGTAGCTCT
CAAGCTCTATATTCCTCCTGTGTTACCCTATCAAATTCTGGAATTACGGGTTTGAC
ATGCATTCTCAATTTTTCAATATAATTAGACTAACATTTTCTTTCTTTCCCTTCCCT
TTGTGACAGGGCTTAATAAATGCAAGGCTATCATTAAAATCACTTTAAAACCAAG
GGTAACCTTAAATTCCTGATCTTCCTGCCTCCATCTCCCAAGTGCTAGGATTACAA
GCATATGTCTGGCTAGGCTGAGATTTTCTATATATTTATGTCCTATTTCCTTCAT
GATTAATATTTTTCCCCAACTGTTCTCATTCTCATTTTACCATAAGCAGCAGCAAG
GAAAAACCAGACCGTACCTTTAACACTGTGCTTGACAATTTCCTTTGCTAAATAT
TTTACAAGCTTTCTCTCCTACAAAACACCAGAACAATTGACACTTTATAACAAGG
CTGAGCTTTCCTCCCACACCCAATAATGGCCTCTTCGACTTCCTTCTAAGGTCTCA
CCGAAAGATCTATAATATTCATCTTCCTAACAACACCTTGTTTAGGGATGTAAGT
GAAAGATTCAACAGAAGAATTTTCATTGCTGTTTCTTTCTGAGCTTGCACCAGAA
ATATGTTTACTATCCATATTGCTAGATTTGTTTTAATATAGAGGCTTACTATACAG
GCCAGAATAGACTTGAAATCATGATCCTTCTGCATCATCCTTCAAAGTTCTGGAA
TTACAGATATGCAGTACTGTACCTGGCTTCACTCTGTATTCCTACCAACAGGGTTT
CGGGTTTTCTTTGTTTTTGTTTTTGTTTTTGTTTTTGTTTTAAGCAGTGCAGACTCT
TTCTACTGTACACCTCAAAACTCTGTAGCTTTTGTCCACTCTACCCAGTTCTAAAT
CCATTTTCACATCCTTAGGTATTTGTGGTATTTGTTTATATAAACCCCCAATTCCT
GGCACCAAAACCTATATTAGCTTCCTGAAGCTACACTAAGAAAAGCAGAATAAA
GCAGGTGCCTTAAACAACCAAAATTTACTTTCTCACACTGTTTGGAACTGAGAGT
GTGAATGGAAGTGTCAGCAGGGCTGTGTTCACTCTGAAAGCTCCAGGTCAGGGT
CTTTCTGTGCCTCTGCAGATTCTAGAAGCCTTCTATGTGCCTTATCTTATAACTGC
ACCTTTTGCCTGTACTGTCTTTTGCCTGTACTGTCTCACAACATCTCCTGTATGCTT
TTGTCTCATAAGGACACCAGTCACACTAAGTTAAGGGCTCAACATGCTCCATTAT
GACTTCATCATAACTTATCTATCTGTAAAGACCCTGTTTCCCAGCCACATTCTGAG
GAACTGAGAGTTCCAACTCCAGTATAGTTTATAGGGTCATAATTCAAGCCATTAC
AGAGGTCATCTCCACCCTTACTCTGAAGAAATACAGAGGCTAGTAGAGCCCTGTG
CTCTGCCCATCCACTTTGGTCTGTGTTCCTCATTCATGTAGCTCCCATCCTGACTTT
CTGGACCCTCTGCTTTGTTCTAGTTGTACAAGGGTTCTAATCCAGCTGTCAACCTC
CTTTCCCTTTTCCTACCAATAGCAGAAAATCTAATTCTTGGAGTCCCTAGGTCCT
TGCCAACACACCACTTGGAAGCATCCTCATCTTTGGTGTGAGCCCCACCCACCTC
CTCCCCCATTTCAATGCTCTGTAGCTATTCCTTCAGCCCTGTGGCTGGTCCTGACC
TTTACCCTCAGATCTCAGGTGACACCAGGGCCAGGCATATGGGTCACATCTGCTA
TCATTACTCAGAACCAAGGGCCAGGAAGTACAAATGCGGCCTGCCCCAGCCTTG
TCCTGAAGAGCACCTGAGCTTTCGAATAGTCAGCGGGGCTGCCAATGTCATCGGG
CCCAAGATCTGCCTCGAGGACAAGATGTGAGCATATGGGCTGGGAAGTGGGAGG
GGAACCTGAGGCCAGGTCTATAAAGGCCAAGGGCTGATGGTTATGTGAGGAAGA
GCAAAGCTGATATGCCCACAAGAGATCCTCTTCCCTCCCCCTCCCCAGGCTCAT
GAGCAGCGTCAAAGACAATGTGGGCCGTGGCCTGAACATCGCCCTGGTGAATGG
TGAGTCCACCATGTTATAGGGTCAGAATTCAGATTATAGAAGCAGATACCATGGT
ATGGCCTGTCCCCTCTACTTCATTACTCCCTATGCAGATGCAGGTGGCTTCTGGGC
ACTCCCCAGGAGGCTTGAAGAATTCTATACCCGCTGAAAGTAGTGACAATAA
TGGTAGATGCTTAGGACCTCAGATGCCAGTGGCTCTATGGGATGTAGCTCTGTGA

Figure 4 cont'd.
TTGACAGGATGACAGGACATGTTTGAGGCTTCTAGAAAGGGCTGCCACCCACCG
TATTTGAGCCTGGGCTGGAGGCTCAGGTAGTAAAATGGTATGTCCTGGCTTGCTC
AGCAGTTCTTTCTCTTGATACAGGGGTCAGTGGTGAGCTCCTAGAAGCCAGAGCC
TTTGACATGTGGGCTGGAGGTGAGTGGCCCACCACAGCAACCTACTGTATATTTT
CTCCCTGAAATCCTGCCCTCTGTCTTTGCACTTAGCTGTTCAAGTATTGCCTTGGA
TTTACAAAATACAAGGGATGGGGAAATCTGTCTGGATTCTGTTTTGTGACTGGAT
GACCCTAGCTTCTTTACCAGTTAGTCTGTGTTCATACTGATGGTCTTTGGTGTGGA
ACATCCCTGGCCCAGTCCCTACTTTGTTTTCCTCATTAGAAGAATATTGTTTGGTG
GGGAAGGGCTGCTTGGTGGAATCTGAAGCTCCATATTCTGTGGGCCCATCTCCAC
CAGATGTCAATGATCTCTTGAAGTTCATCCGGCCACTGCATGAAGGTACCCTGGT
GTTTGTGGCTTCCTATGATGATCCAGCTACCAAGTAAGTGACTGCCAAGTCCAGC
TTCAATCTTGTTCCAATACAGTAATAATCTCCAGTTCACATTCCTTTCTACTGTGT
GACAGGATGAATGAAGAGACCAGGAAGCTTTTTTCTGAGCTGGGCAGCAGGAAT
GCCAAGGATCTAGCCTTCCGTGACAGCTGGGTGTTTGTGGGAGCCAAAGGTGTGC
AGAACAAGAGCCCCTTTGAGCAGGTACAGCAGAGAACCTGGCACCTCTGCCTCC
TGTCCCTGGCAACCTCTTCTCAAAGCTTCCCTGAATTCTACCCAGCTGGGTTCTGG
TCTCTGTCCCTGACCTATGCCCTAGTGATGCCTGGCCCCTTGTTATCACCATGGGG
AGAGACAGTAACTTTGATCTCTCCTGTCCTGTATATATTTCAACCTAAGGAGTCTT
TAAATGTCAAATTGCACATTGACCAGAGTATACCTAAGAAATCTTTACAAGCACC
TTCAGGATGCTCAGTCCAGGGATATAGCTCACTTATGGTGAGTGTTTGTCTAGCA
TACATGAGGCCCTGTGTTCAATCATTAGCATTACATAAAACTGAGCAGGGGAGA
CACCTGTAATATCAACACTGTGGAAGTAAAGGCAAGAGGATCAACTTATCCTTG
GACACATATCAAATTTGAGGCTAGCCTGGACTACATGAAATACTGTTTCAGATTT
TAAAAAGAAAAAAAGATGCTCACTACCATCCTAACCTTGTCATAACCCAGTTTTC
CAGTTTATGCTACACACTCCTTTCTCACCTACCCTGGGTTCTCTCTTAGGGTACAT
CAGTCAGGGTTTATGCTAGCGGATGCTAGAGAGAGGAGGGCCCCTGGCATCATC
CTTACCTAAGGAGGCTCTCAGCAAAAAGTCTTAGGTAGGCCTCCAAGCACTGCTT
TCAACAAATACAGATTTCTCCATTGCTTTGGCTGACAAAACAACTCAAGCTCAT
GCCTCCCAAGACCCTTCACCCCAAATAGGGTAGCAGTTTCCAGCATTTCCCTGAA
GCCAGGGCCATATAGACTCCCTCCTGTCCACAGTGGCCCATCCCTAGTTCACTTA
TAAAAGAATAGACCACCTCAGCCATCCCCAATTTTCCCTGTGTGAATGAAGGGAA
GGGCAACAGACTGAAGAATATTCTGATGTTTGGCCCCTGAGAGCCAGATCATGA
CTTCCTATTAACCTCTACAGCATATGAAGAACAGTAAGCACACCAACAAGTATGA
GGGCTGGCCAGAGGCCCTGGAGATGGAAGGCTGTATCCCTCGAAGGAGCATAGC
GGGCTAGCACAGCAGAGCTCTGGGACCAGACTGAAGGAGGCAGCATGGCACCA
GTGTCAGGTGGAGACTGTGCCCCATGCCCAGGCATGAGGCTCCCCCTCCCTAACA
CATTAGGGCTTGAAAGTGGCCTCAAGGTGATGGGGGCTGCAGGGCTGGCCCATT
TCATTTTGTCAGGGAGCTTAGGTACCTGTGTCCTTGTTTTCCTAAAGCTGATCCCA
CAGTCAGTTCCCACCCAGCCCCTTCCTCTGCCCTCATGTGTCATCTTCTATTTCT
CTTTTTTTTTCATCTTCTATTTCTTGAGTGCCCCCAGAGGCAAGGGTCTTCAATG
CTTGCCCCTGTCACTGGAGCAGGTATTGGGTAGGTTGGGACATCTTCAAGAAACT
CTCCCTCCCAGAGGCACTGCACTGGTATCCAACCCTGTTTTCAGTGATCCTTTAAG
CCAAATCAGAACTGATTGGATGACTTCTGCAAGCCTGAATGGAGCAATCTGGCCT
TAAGTGCCCAAGTAGCTGGAGTCCAATCAGAGTTCCTCACAAGGTGTCTGTCAGA
GGGCTCACCTTCTAAATGACCTGTTTGTTAATAAACTAATTCTTGCAGTGGAAT
AAAGTGTATTCAGATGTCCTCAGTGGAGAGTCAAGGGTGGTGTTGTCCCGTGTGT
GTGGAGAAGACAGATAAGTCCCAGAAGCTCAAGCAGCACTCTTGGAGCTTAAGC
AGACAGCCTTTTGTCAACAGACCCTGTGGCCAGATGTGGCTCCGATAGGAGGTA

Figure 4 cont'd.
GAATAGCTCCCAGCTGACATTACTCATGGATTTGATTAGAAAGATGGTTCTGTTC
AAAGGAACTCAAGGAAACTCACCACCTGTCACTAATCCAGTGTGAGCCTATAGG
GGAAAAGATAGGAATTAAAACCAGTACAGGCACTGAAATAACTCCAGGAGTGCA
GAAGCAGCCTGGTTCCAAAAGGGAAAGAATACAACTTGGAATTTCTAGATGAGA
GACATCAAGGCATAGTAATTTGAGGATCCCATAAAGCATTTCTGAGGTGGCCATG
CCAGGGGTGATAAACTTAGAAGTCCTACTGTGGCAATCTGCTTTCTAAGCCTTCA
ACCCATTGCTGTTCAGTAGTTAAGTCTCAGAAAAAAAAAATGGTGAGGGCAAA
TCAGGCCTCAAGAAATGAGAGTAGAGCTGGGTATGGTACTTATACATCTATTATT
CCAACACTAGGAAGTTGTCTTAGTCAGGGTTTCTATTCCTGCACAAACATCATGA
CCAAAAAGCAAGTTGGGGAAGAAAGGGTTTATTCAGTTTACACTTCCATGTTGTT
GTTCATCACCAAGGAAGTCAGGACTGGAACTCAAGCAGGTCAGAAAGCAGGAGC
TGATGCAGAGGCCATGGAGGAATGTTCTTTACTGGCTTGCTTCCCCTGGCTTGCT
CAGCCTGCTCTCTTAAAGAACCAAGACTACCAGCCCAGAGATGGTCCCACCCAC
AAGGGGCCCTTCCCCCTTGATCACTAATTGAGAAAATGCCTTACAGCTGGATCTC
ATGGAGGCATTTCCCCAACTGAAGCTCCAGCCTGTGTCAAGTTGACACAAAACTA
GCCAGTACAGAAGTGGAGTGAGGGAGAAGGATCAAAAGTTCAAATCAAACTGTG
ACTACTTAGCAAATTCCAGGACATCCTGGAGTACATGAGGTACTGCATCCATAAG
GGTGGGGTGGCTTATTAGATAAATGTACCTGCTGCCAAACCTGGTGATCCCTAGA
ACCCATGGTAGAAAGAGAGAAGCAACTTTTGCAAGTTGTCCTCTGATCATATGGT
AGACATGTGCATGCACATACACAAGTAAGTAAATGTTAAGAAAGAAAAAGAA
GAAAAAGAATGGAAGTATTTGATGGCGGGAATATGCTGGTTTAGAGGTATGGGG
TGCCCAGGAGAGGCATGCTAGGGAAGAGATAGTTGTATATCCAAGACTAACAGA
GTCAAGCAGGAAAGTCAGCAGGGCTCAGCTCTTTGTCTCAGATATAGTGGTGATA
ATAGCTAACACCCAGCCCTCTAAGTCTATACTGAACTCTGTGTGTGCCTGTTTGTG
CAGGTGTACTCATATGGATTCATGTTTGTGTGCATTCATATGGAGGCCAGAAGTC
AACCTTGAGTGTCCTTCAAATGCTGACTTTATTTGGTTTGGGTTTTTGGTGGAGTT
CGTTGCTGTTTTTTTGGAGAGAGTTTTATTTGTTAAACAGGGTCTCACTGTAGTTC
TGTCTGGCCTGGAACTTGCAAATATCCTCCTACCTCTACTTCCCAACCGTTGAAAT
TAAAGGCAGGTGTCAAGCCTAGCATTAGTTACTTGTTTTGTTGTTTGAGAAGTGT
CTCATTATGTCCTGGCTGTCCTGTAACTCACAAAGATCTACCTGTTTCTGTCCCCC
AAGTCCTTGGATGAAAGGCATGTGCCACCACATTCCACTGAGTTTGTTCATTCAA
ATGGCCTGGAACTCCAAATTAGGCATAAGGCCTTGTATTAGTCTGGGTTCTCTAG
AGTCACAGAACTTATGGATAGTCTCTATATAGTAAAGGAATTTATTGGTGACTTA
CAGTGTGCAGCCCAATTCCCAACAATGCTTCAGTAGTATCTGTGAATGGAAGTCC
AAGGATCTAGCAGTTACTCAGTCTCACACAGCAAGCAGGCAAAGGAGCAAGAGC
TAGACTCCCTTCTTCCAATGTCCTTATATGGTCTCCAGCAGAAGGTGTAGCCCAG
ATTAAAGGTGTGTTCCACCAGATGACCTTGAACTCAGAGATTTAATCTTCTGGAA
TCCATAGCCACTATGCCTCAAGATCTCAAGATCTCCATACCAAGATCCAGATCAG
AATCTTCTATCTCCCAGCCTCCAGATAAGGGTCACCAGTGAGCCTTCCAATTCTG
GATTGTAGTTCATTCCAAATATAGCCAAGTTGACAACCAGGAATGTCCACTTAAG
TTCTAAGTACCCACCTATGCACCTATGTCTGCCCCAGCACTGCTACGATGCCTG
TCTTTTTTTGTTGTGTTTTGTTTGTTTTCGAGACAGGGTTTCTCTGTATAGCCCT
GGCTGTCCTGGAACTCACTTTGTAGACCAGGCTGGCCTCAAACTCAGAAATCTGC
CTGCCTCTGCTTCCCAAGTGCTGGGATTAAAGACGTGGGCCCCACGCCCCACG
CCCGGCTGTCTTTTTATTTGTGTGGGTTCTGGGGTCAAACCCAGGTCCTCATGCT
TGCACAGCCAGTCCTTTAGAAACTAAACACTCTACAGCCTCTCTGTACCAGACTC
TGAAATATATTCTGGGGGCTCAGTGGTCTTATGTTCTTTCCCCAGCACTGCCAAA
AGAAAATTACAATTCTGTTGTCCCCTTTTCAAAAGACTTTCTTTCTTTGAGTCATT

Figure 4 cont'd.
TTAAGTTCCCAGAAAACTGAAAATTACAGAAACTGCCCATCAGACTCCTGTTGGT
CATAATAAGTATTTTTATATTATGTTTTCTATGAGTATTATGTATTCTTTGATGTT
TGTACTTTTTAATCATTTTACATGTGTTTATTTTCTGTGCATATGTGTGAAAATCA
GGGGACAACTTTCAGGAATTGATTCTTTTCTTCCTTCATATGAGCCCTAGAGATC
AAACTCAGGCCTTTACCCACTGAGCCATCTCATAGACCCACATTCTTTGAGTTTTG
ACAAAATCAGATAATAACATATATCCATGATTATCAAAATGTATTTGTCTCTTGA
TTCTATTATGGAAATTTAAAAAAATCTCAAGGTGTAGAGAGAATAAAAATCCAG
TACACCTTTTACCTGCTTCCACAATGTAGCCAGTATTGCCTCTGCTACACTTAGAA
TGTAGCCAGTATTGCCTCTGCTACACTTAGAATGTAGCCAGTATTGCCTCTGCTAC
ACTTAGAATGTAGCCAGTGTTGCCTCTGCTACACTTAGAATGCTCCCAATGGAGT
CAAACAAGTCTCAGCTTATTCTCTCAAGATTTTAGTTTTATACAACTTGCTTACAA
AGTTCACACAACCCTAGAAAGTCACTGTTGCCACTGTACAAAACAGTTACAGGG
CCATGGTGAGTATAGGAGAGCTACAACAGGACCTAGAGGTTAGAACAAGATGAG
TAGGCTCCCTGGGTTAGCAGCTTACTTCCAGATGAAGCGGAATCTCACTAAATAT
GCTTACTATTAGCTAGAAGGGCAGAGACCCTAATGTGCATCCAGATGATTATAA
CTTTTCAATCTTTGTCTTTGTGTGTGTGGGGGGGGGGATATGTGTGCGCACAC
ACACAAGAGGAAGCCAGGGGACAACTTTAGGTGTTGTTCCTCCAGTGCTGTCCAC
CTTGTTAGGGTATATGGGATGGGGTACAAATGCACAGGTATATAGAAGCCAGAG
GTCAGCTTTCGGTGTTTTCTTCGATTACTTGCCACCTTAATTTTTTAAGCAGGAA
TGCTTTTTCATATCTTAATTTTATTTTTATGTGTTTGTGCATTTTGTCTGCACATAT
CTTTGTGTACATTTTTGCTCCCAGTGCTTGTAGAGAAAGCGTCTGATCACCTGGA
ACTGAAGTTACAGAGCAGCCAGTGCTCTGAGCTACTTCTCTAGTCCGTGTGTGTG
TGTGTGTGTGTGTGTGTGTGTGTATACACATATATACAGTTAATTTTTAAAT
ACTTTCTAATATTTAAAATTTTTAAATATTTTAATTACATTTCAATTTACTTTGTAT
GTGTATAAGTGTATGTGTATGTTTGTATCTGTGTATGTTGTAGAGGTACATGTCAG
AAGACAACTTGAGAGAATGGGTTCTCTTCTTCCATCATATAAGTCCCTGCCAGGG
ATCAAACTCAAGTCATCATGCTTGGTGGAAGGCACCTTGATCCACTGAACAATCC
CATTGATTCCCACCTTGTTTTCTTTTTCTTTTTTTATTGTGTTTTTGGTTTTGTTTT
GTTTTGTTTTTCGAGACAGGGTTTCTCTGTATAGCCCTGGCTGTCCTGGAGCTCAC
TTTGTAGACCAGGCTGGCCTCGAACTCAGAAATCCACCTGCCTCTGCCTCCCTAG
TGCTGGGATTAAAGGTGTGCACCACCATGCCCGGCTTCCCACCTTGTTTTCTAAG
AAACAGTCTCTCATTGGCCTGGAATTCACCAAGGAAACTAAGCTGGCTGGCCAGT
GAGCCCCAGGGATCCTCCTGTCTTTATCTTCCCACCACTGAAATTACAAACATGT
ACCACTTTGTTCTGAAGATTGAAATTGGGTATTTGTACTCAATTTAACTATCTTCC
AGGCCCAAATTTTGTCCATTTGCTTTACGGATGTTAACTGAGTGTCTTGTTTTACT
GCTGTGAACAGACACCGTGACTCTTATATAAGGACAACATTTAATTGGGACTGGC
TTACAGGTTCAGAGGTTCAATCCATTATCATCAAGGCAGGAGCATGGCAGCATCC
AGGCAGGCATGGCAATGGAGAAGCTGAGAGTTCTACATCTTCATCTGAAGGCTT
CTAAGAGAAGACTGGTTCCCACATGGTTAGGAGGAGGGTCTCATGGCCCACACC
CACAGTGACACAATTCCTCCAACAAGGTCACACCTCCTAATAGTGCCACTCCCTG
GGCCAAGCATATTCAAAGTTTTGTTTATTTTTACTCTGTGTGTGTGTGTGTGTGAG
TGTGTGAGTGTGTGTGTGTGAGTGTGTGTGTGTGTGTGTGTGTGTGTGTGTGTGA
GTGTGTGTGTGTTGCAGGCCCATGTGTGCCATGTGTCAAAGCCAGAGAGGTATGG
GGAACATGACATCCCTTCATCTATCACTCTGCATTATTTCTTTAAGACATTTTCAT
ATTCAGATTCGTATCTCACTGA (SEQ ID NO: 1)

MICE WITH A MODIFIED GLUCOSE-6-PHOSPHATE DEHYDROGENASE GENE

CROSS-REFERENCE TO RELATED APPLICATIONS

This application claims the benefit under 35 USC 119(e) of prior U.S. Provisional Patent Application No. 62/169,211, filed Jun. 1, 2015, the disclosure of which is hereby incorporated by reference in its entirety.

FIELD

The present invention relates to a transgenic mouse with modified glucose-6-phosphate dehydrogenase which can be used as a model and screening tool for various aspects of glucose-6-phosphate dehydrogenase deficiency.

BACKGROUND

Glutathione (GSH) is a tri-peptide that serves as the primary anti-oxidant pathway by which mammalian cells handle oxidative stress and detoxify reactive oxygen species (ROS). When it serves as a potent anti-oxidant, 2 molecules of GSH are conjugated to form GSSG. In order for the GSH system to remain active, GSH must be regenerated from GSSG, which is accomplished by the enzyme glutathione reductase (GR).

In order for GR to regenerated GSH from GSSG, it requires NADPH as a co-factor. Thus, a lack of NADPH can result in the loss of a cell's ability to handle oxidative stress, since once GSH is converted to GSSG, anti-oxidant capacity it depleted and cannot be regenerated (without NADPH).

NADPH is generated through the pentose-phosphate-shunt (PPS), which is a pathway involved in the basic cellular metabolism of glucose (the main fuel source for cellular metabolism). A central enzyme in the PPS is Glucose 6 phosphate dehydrogenase (G6PD), which generates NADPH. Thus, a deficiency in G6PD prevents the generation of NADPH, which in turn prevents full activity of GR, leading to an inability to regenerate GSH from GSSG, and thus diminished capacity for a cell to handle oxidative stress (see FIG. 1 for pathway depiction).

SUMMARY

Disclosed herein is a transgenic mouse with modified glucose-6-phosphate dehydrogenase which can be used as a model and screening tool for various aspects of glucose-6-phosphate dehydrogenase deficiency.

In a first aspect, disclosed herein is a transgenic mouse whose genome includes an insertion into the glucose-6-phosphate dehydrogenase gene locus, wherein said insertion includes a human variant of the glucose-6-phosphate dehydrogenase gene.

In some embodiments, the human variant of the glucose-6-phosphate dehydrogenase gene encodes a protein with reduced stability or activity.

In other embodiments, the reduced stability or activity is at least 90%, 80%, 70%, 60%, 50%, 40%, 30%, 20%, 10%, 5%, or 0% of the stability or activity of the wild type mouse or human glucose-6-phosphate dehydrogenase protein.

In other embodiments, the human variant of the glucose-6-phosphate dehydrogenase gene is Med-G6PD cDNA.

In other embodiments, the Med-G6PD gene is fused to the N terminal tail of the endogenous mouse G6PD gene.

In other embodiments, the Med-G6PD cDNA is flanked by LoxP sites.

In some embodiments, the insertion site includes the sequence shown in FIG. 4.

In some embodiments, provided herein is the progeny of the cross of the mouse of the above aspects and embodiments with a transgenic mouse expressing a tissue specific CRE.

In some embodiments, provided herein is the progeny of the cross of the mouse of the above aspects and embodiments with a transgenic mouse expressing an inducible CRE.

In some embodiments, the CRE activity is inducible with tamoxifen.

In some embodiments, the Med-G6PD cDNA is expressed in an adult animal.

In a second aspect, disclosed herein is a transgenic mouse whose genome includes a homozygous insertion into the glucose-6-phosphate dehydrogenase gene locus, wherein said insertion includes a human variant of the glucose-6-phosphate dehydrogenase gene.

In some embodiments, the human variant of the glucose-6-phosphate dehydrogenase gene encodes a protein with reduced stability or activity.

In other embodiments, the reducedstability or activity is at least 90%, 80%, 70%, 60%, 50%, 40%, 30%, 20%, 10%, 5%, or 0% of the stability or activity of the wild type mouse or human glucose-6-phosphate dehydrogenase protein.

In other embodiments, the human variant of the glucose-6-phosphate dehydrogenase gene is Med-G6PD cDNA.

In other embodiments, the Med-G6PD gene is fused to the N terminal tail of the endogenous mouse G6PD gene.

In other embodiments, the Med-G6PD cDNA is flanked by LoxP sites.

In some embodiments, the insertion site includes the sequence shown in FIG. 4.

In some embodiments, provided herein is the progeny of the cross of the mouse of the above aspects and embodiments with a transgenic mouse expressing a tissue specific CRE.

In some embodiments, the Med-G6PD cDNA is expressed in all tissues.

In some embodiments, provided herein is the progeny of the cross of the mouse of the above aspects and embodiments with a transgenic mouse expressing an inducible CRE.

In some embodiments, the CRE activity is inducible with tamoxifen.

In some embodiments, the Med-G6PD cDNA is expressed in an adult animal.

In further aspects, disclosed herein is a method for identifying or screening for drug induced hemolysis by infusing the transgenic mouse disclosed above with drugs to be screened, and testing RBC levels and hematopoiesis post drug exposure.

In further aspects, disclosed herein is a method for identifying or screening for drug induced hemolysis by labeling RBCs from the transgenic mouse disclosed above and infusing them into a wild-type recipient, treated with the drug to be tested, followed by calculating RBC circulatory lifespan.

In further aspects, disclosed herein is a method for identifying or screening for drug induced hemolysis by exposing RBCs from the transgenic mouse disclosed above and infusing them into a wild-type recipient, treated with the drug to be tested, followed by calculating RBC circulatory lifespan.

In further aspects, disclosed herein is a method for testing the effects of human drug metabolism by incubating drugs with tissue culture cells expressing human metabolic enzymes (e.g. cytochrome p450s), followed by using the supernatants (containing metabolized compounds) by any of methods disclosed above.

In further aspects, disclosed herein is a method for testing effects of human drug metabolism by exposing humans to drugs, collecting plasma or serum from the humans, and using the plasma or serum as in any of the methods disclosed above.

In further aspects, disclosed herein is a method for testing the effects of human drug metabolism by breeding G6PD deficient mice with strains of mice that are transgenic for human metabolic enzymes (e.g. cytochrome p450s), and testing the resultant strains (expressing both the transgenic enzyme and with G6PD deficiency) by any of the methods disclosed above.

In further aspects, disclosed herein is a method for developing blood storage systems to overcome the problem of G6PD deficiency of stored human RBCs, by using RBCs from the transgenic mouse disclosed above as a platform for manipulating storage conditions.

BRIEF DESCRIPTION OF THE DRAWINGS

FIG. 4 shows the sequence of the G6PD locus after homologous recombination.

DETAILED DESCRIPTION

The present invention generally relates to the generation of transgenic mice with modified glucose-6-phosphate dehydrogenase which can be used as a model and screening tool for various aspects of glucose-6-phosphate dehydrogenase deficiency.

It is to be understood that this invention is not limited to particular methods, reagents, compounds, compositions or biological systems, which can, of course, vary. It is also to be understood that the terminology used herein is for the purpose of describing particular aspects only, and is not intended to be limiting. As used in this specification and the appended claims, the singular forms "a", "an" and "the" include plural references unless the content clearly dictates otherwise.

The term "about" as used herein when referring to a measurable value such as an amount, a temporal duration, and the like, is meant to encompass variations of ±20% or ±10%, such as ±5%, such as ±1%, such as ±0.1% from the specified value, as such variations are appropriate to perform the disclosed methods.

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein.

Figure 1:
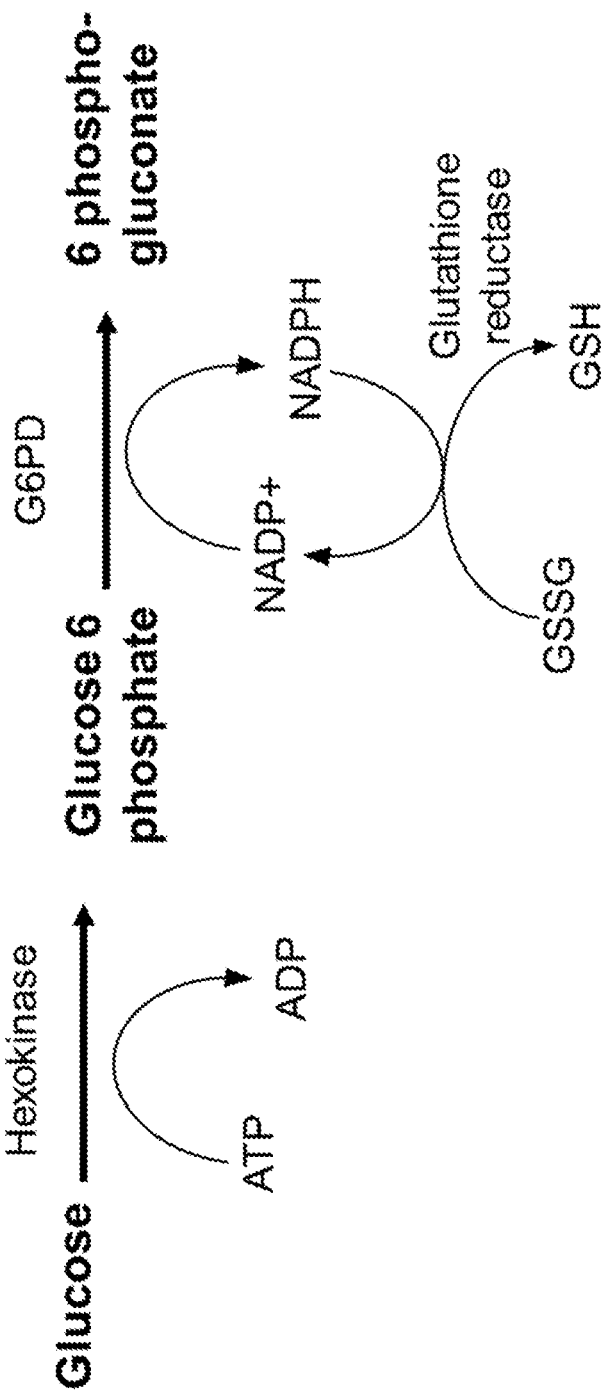
FIG. 1 shows a schematic of the pathway whereby G6PD generates NADPH from NADP+, which then serves as a cofactor to allow glutathione reductase to regenerate GSH from GSSG.
Figure 2:
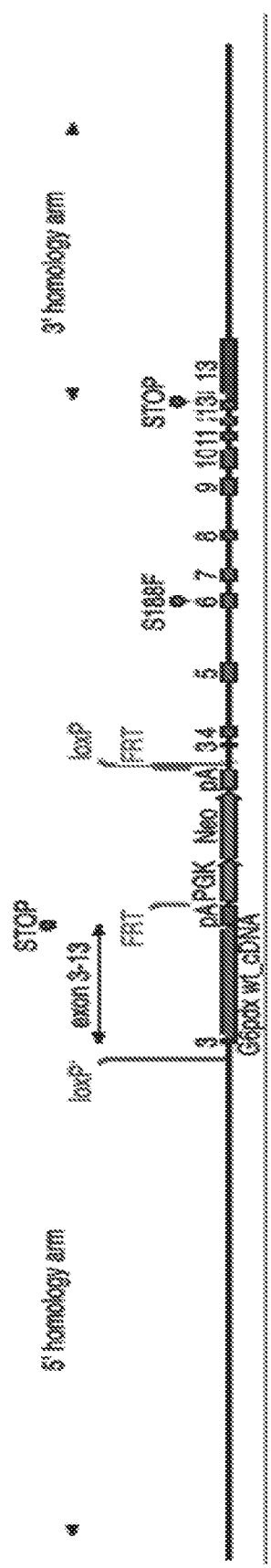
FIG. 2 shows a map of a targeting construct to knock in the human Med-form of G6PD into the murine G6PD locus in a conditional fashion.

To generate a better model of human G6PD deficiency in mice, a human variant of G6PD that leads to a severe deficiency (the Mediterranean form—Med-) was isolated. The Med-G6PD was inserted into the mouse G6PD locus, in a fashion that the mouse G6PD would be replaced by the human form (FIG. 2). This insertion was carried out such that the endogenous murine regulatory elements were kept intact, so as to allow normal gene expression profiles. In addition, to maintain genomic integrity, a N terminal tail of the murine G6PD was kept in place and fused with the remaining human G6PD Med-form. Finally, there was concern that disrupting G6PD in mice may affect embryogenesis or other issues of critical development. Accordingly, the human Med-G6PD was inserted into the mouse genome flanked by LoxP sites such that the mouse gene was not disrupted until CRE recombinase was present. This allows the breeding with CRE expressing mice, in order to allow the recombination to occur. In addition, one can cross the B6.G6PD-Med-mouse with an inducible CRE animal, to allow recombination to occur in a fully developed adult mouse, by injecting tamoxifen, which induces the CRE activity. This allows induction of the human Med-G6PD form in an adult animal, after normal development, thereby circumventing issues of developmental toxicity. This will result in the expression of the Med-G6PD in all tissues, and also eliminate the natural murine variant. As with humans, as the deficiency is one of enzyme stability, cells that have ongoing gene synthesis will not be affected; however, cells that no long express genes (e.g. red blood cells) will have decreased G6PD activity as a function of their age.

Figure 3:
FIG. 3 shows the structure of the G6PD locus after homologous recombination.
Figure 5:
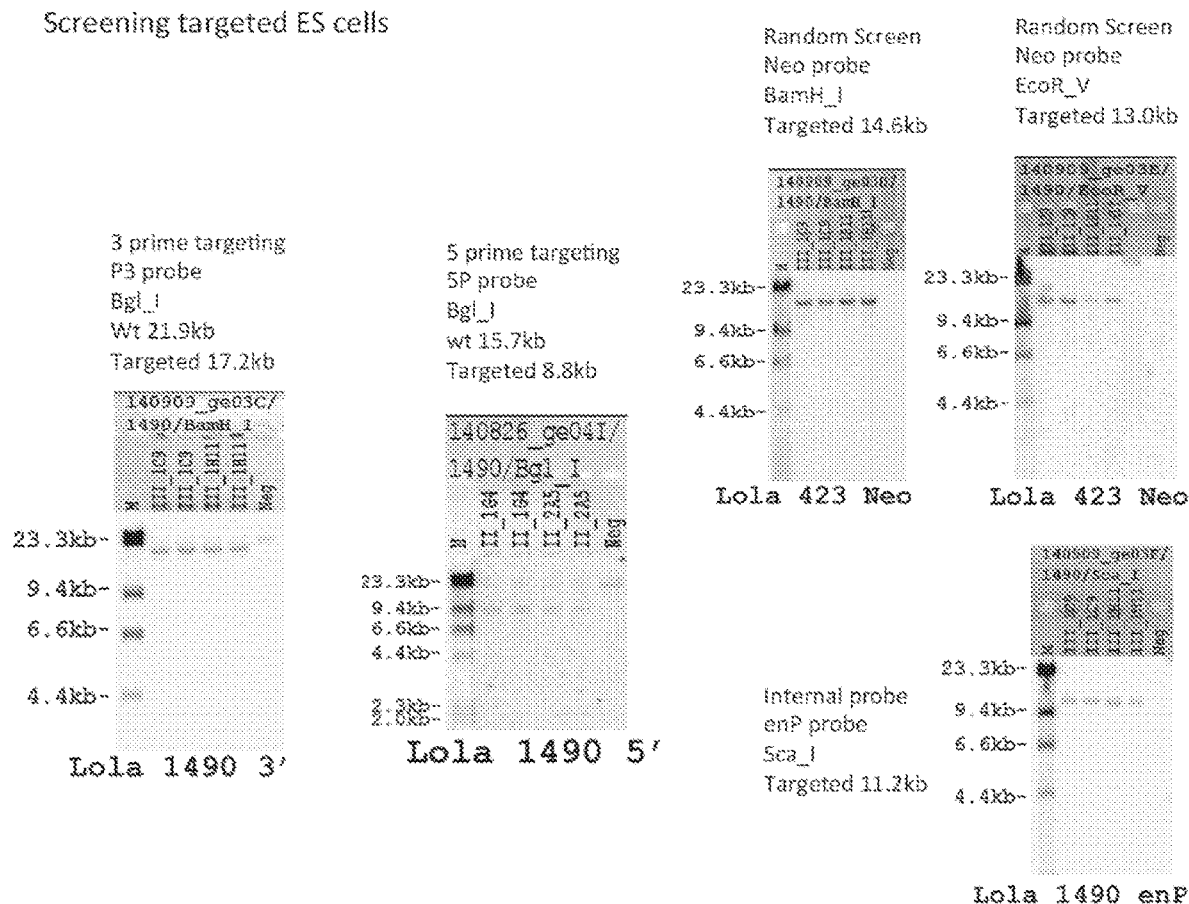
FIG. 5 shows representative Southern blots demonstrating the homologous recombination event.
Figure 5:
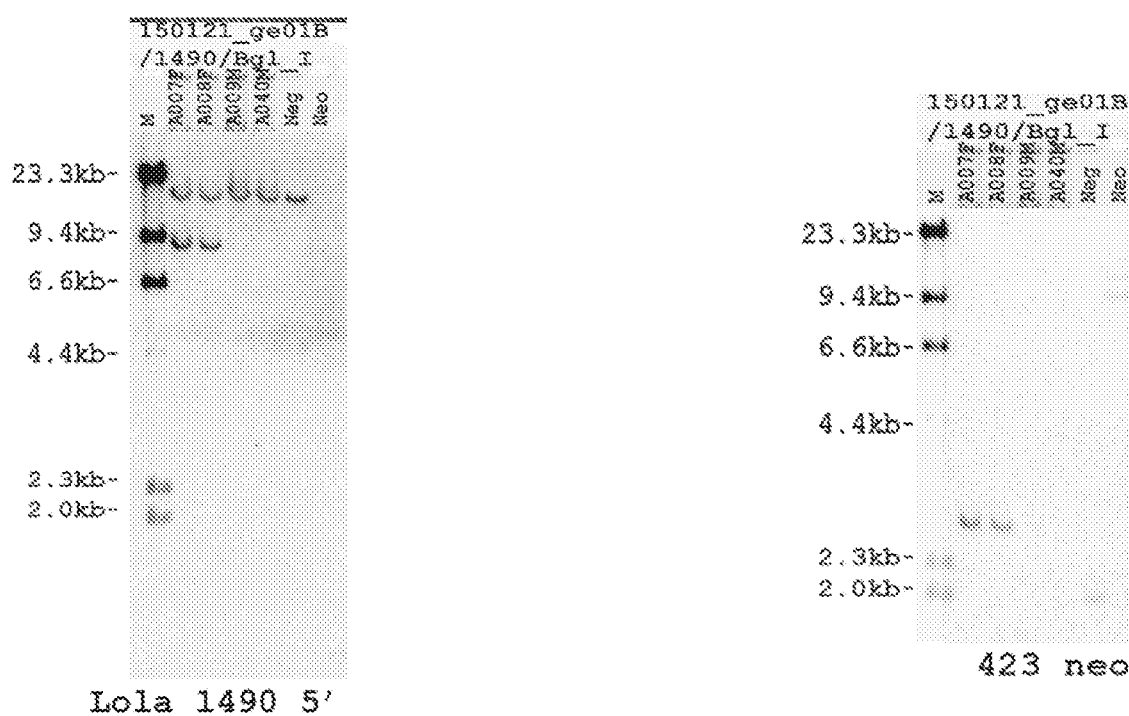
Figure 5:
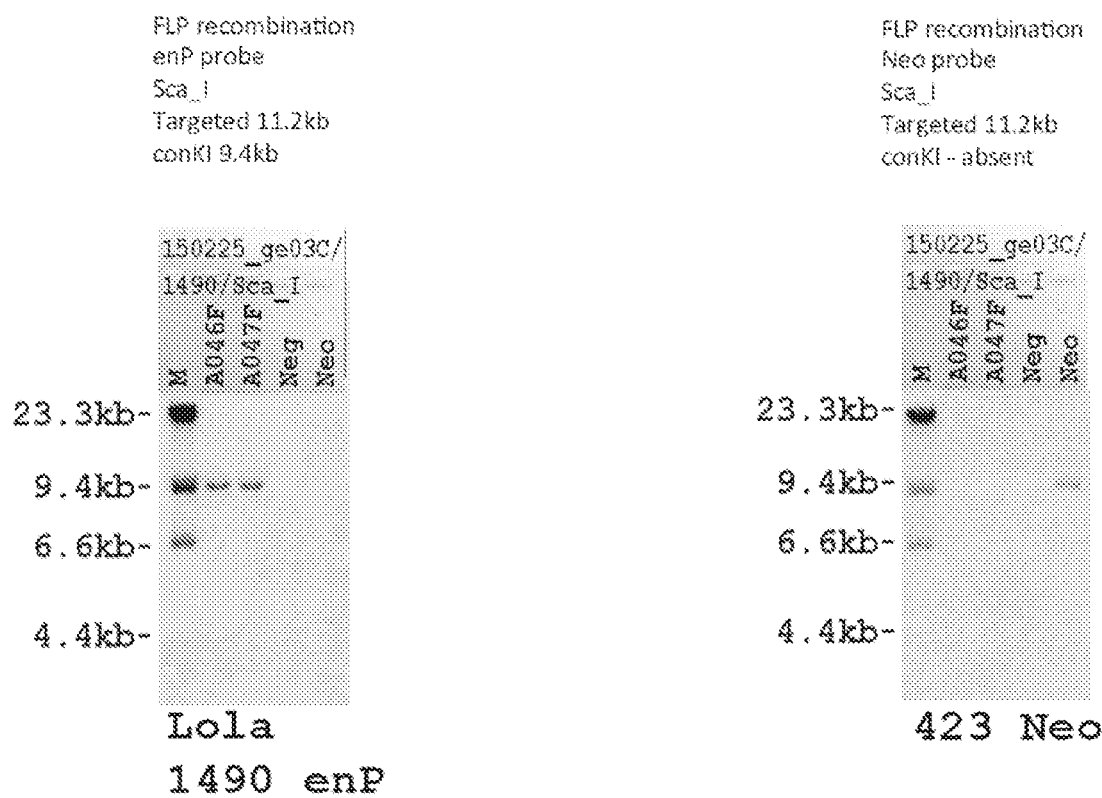

FIG. 2 shows the final genetic changes and the full targeting construct, which was electroporated into C57BL/6 stem cells. FIG. 3 shows the structure of the G6PD locus after homologous recombination. FIG. 4 shows the sequence of the G6PD locus after homologous recombination. Clones resistant to a neomycin analogue (G418) were chosen, followed by screening by Southern blot, so as to isolate clones that had the correct homologous recombination without random integration. FIG. 5 shows representative Southern blots demonstrating the homologous recombination event.

After mice were isolated that had germ-line transmission of the correct homologous recombination, they were bred with mice expressing FLP recombinase, so as to remove the Neomycin resistance cassette. The resulting animals were then bred with wild-type C57B/6 so as to remove the FLP transgene. The resulting animals, which constitute the conditional form of B6.G6PD-Med-mouse, are used as described below. In addition, this mouse was bred with CRE transgenic animals that express CRE in the gametes, and progeny mice were isolated, which have the murine G6PD permanently replaced with the Med-form. This animal was then bred with wild-type C57BL/6 so as to isolate B6.G6PD-Med-mice with the recombined locus but without the CRE transgene. Thus, two different strains of mice are described.

B6.G6PD-Con-Med-mouse: This is the conditional form of the mouse so that the Med-form can be selectively expressed in a given tissue by breeding with a tissue specific CRE transgenic mouse. Alternatively, by breeding with a mouse that expresses an inducible CRE construct, one can cause the recombination to occur in an adult mouse after developmental maturity.

B6.G6PD-Med-mouse: This is the non-conditional form of the mouse that has a permanent germ-line replacement of the murine G6PD with the human Med-form of G6PD.

The mice of the present invention have a number of utilities, including, but not limited to the following.

As a model to study altered biology and disease due to G6PD deficiency.

As a model to study storage of RBC from G6PD deficient donors.

As a platform to assess the hemolytic capacity of any drug that may cause oxidative stress when administered, for whatever purpose. Examples include:

A platform to develop novel anti-malarials in which therapeutic efficacy is maintained but hemolytic activity is decreased (or diminished).

A platform to test new drugs and their analogs to assess potential untoward RBC toxicity as a result of G6PD.

A platform to uncover underlying oxidative stress caused by a drug, which might not be readily observable in a recipient with normal G6PD activity.

Figure 6:
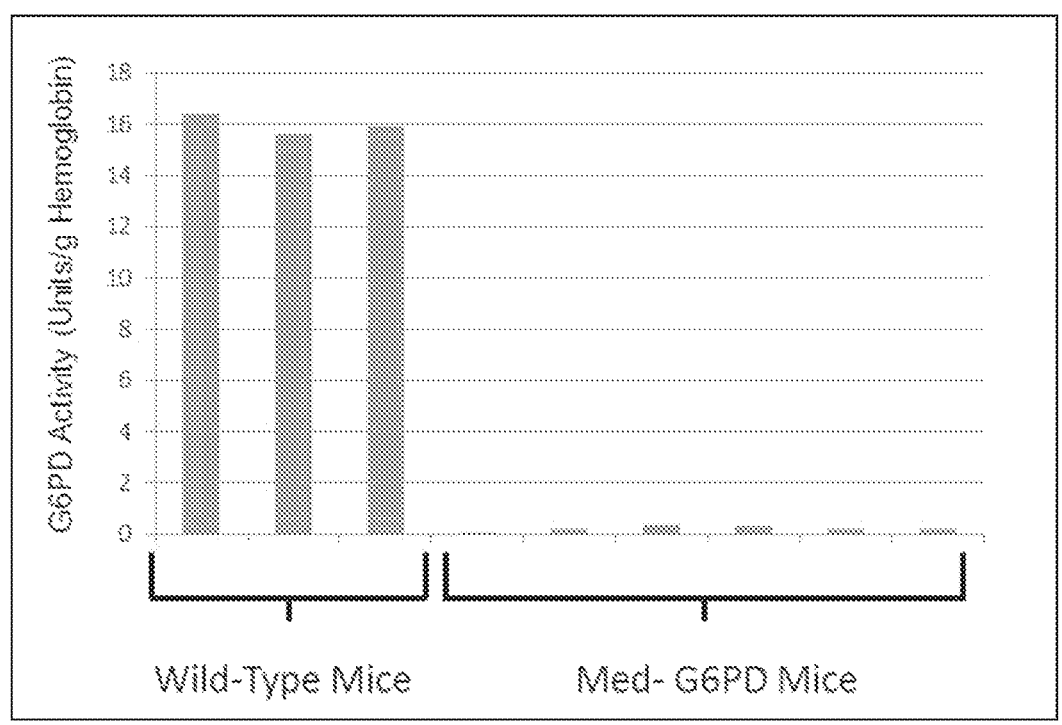
FIG. 6 provides data from characterization of Med-G6PD mice.

The subject disclosure also includes characterization of Med-G6PD mice. Data from such characterization is provided, for example, in FIG. 6. FIG. 6 illustrates that the genetic modification made according to the subject embodiments resulted in the same general phenotype as seen in humans with the genetic deficiency.

More specifically, RBCs from mice with the described genetic modification (Med-G6PD mice) were analyzed with regards to measuring G6PD activity. The data of FIG. 6 was generated by taking blood from the indicated mice and performing an enzymatic assay for G6PD activity, as a human would be screened for the illness. Whereas wild-type mice had normal levels of G6PD, 5 out of 5 (100%) Med-G6PD had profoundly decreased G6PD activity in their RBCs. This enzymatic activity demonstrates that the genetic modification that was accomplished (with a Southern blot) resulted in the predicted enzymatic phenotype, consistent with the known phenotype of humans with the same Med-G6PD mutation as has been introduced into the Med-G6PD mice.

Accordingly, the subject embodiments, not only include making the genetic alteration in a mouse, but also introducing the human gene into the mouse and confirming that it behaves the same in the mouse as in the human. As such, the methods include confirming that the genetic change has the same outcome on mouse biology as it does on human biology. Specifically, the enzymatic data provided in FIG. 6 shows that after introducing the human gene into the mouse, it behaves the same in the mouse as in the human.

Utility

Genetic deficiencies in G6PD are highly common in individuals of Mediterranean and African descent, and maps geographically to areas in which malaria is endemic. It appears that G6PD deficiency confers resistance to malarial infection, and thus has been selected for over long periods of time. Given how central G6PD is to mammalian metabolism, a complete deletion of G6PD is not compatible with life, and is not found in viable humans. Rather, the majority of mutations in the G6PD gene destabilizes the enzyme, such that it decays more rapidly than in non-deficient individuals. This results in a selective G6PD deficiency in red blood cells (RBCs), since RBCs cannot synthesize proteins, and thus their G6PD activity drops as a function of their age. For other cell types, the decreased G6PD stability can be compensated for by increased protein synthesis. Thus, most G6PD deficiencies result in a selective defect in handling oxidative stress in RBCs.

In addition to conferring resistance to malaria pathology, G6PD deficiency also causes several problems for G6PD deficient individuals. In the normal state, they remain healthy: however, if a particular oxidative stress is encountered, then their RBCs become rapidly damaged and can be destroyed. Such oxidative insults can come from diet, drugs, or disease. Most famously, is that consumption of fava beans, a food that generates ROS and oxidative stress, results in hemolytic anemia in G6PD deficient individuals. More importantly, multiple drugs have the same effect, and thus cannot be consumed by G6PD deficient individuals. Ironically, whole classes of anti-malarials have this effect on G6PD patients. Other drugs including aspirin and other nonsteroidal anti-inflammatory drugs (NSAIDS), nitrofurantoin, quinidine, quinine, sulfa-drugs (including Bactrim), and dapsone can have similar effects. Environmental toxins, that are safe for non-G6PD deficient people can also cause hemolysis (e.g. mothballs). Moreover, oxidative stress from disease can also have an adverse effect on G6PD deficient individuals.

An additional issue of G6PD deficient people is the concern regarding blood collection and storage. It is believed that RBCs from G6PD deficient donors store poorly, and upon transfusion, both confer less therapeutic benefit and may also be damaging. One might suggest simply avoiding collecting RBCs from G6PD deficient donors; however, matching of RBC antigens is essential in chronically transfused patients. Because some of the major illnesses that require chronic transfusion are found in people of the same background as G6PD deficiency (e.g. sickle cell anemia in individuals of African or Mediterranean descent), the matching of antigens essentially shuttles G6PD deficient blood selectively to patients with sickle cell disease (SCD) (and other pathologies). Thus, the effect of G6PD on RBC storage is an important clinical problem.

Prior to the content of the subject disclosure, there were no good animal models of G6PD deficiency. As with humans, a straight G6PD knockout in mice is not compatible with life, and mice engineered in this way are not viable. Mice have been described with decreased G6PD; however, such is a general decrease in all cells. Unlike humans, all of the RBCs have decreased G6PD regardless of their age. In contrast, in the human G6PD deficiency, the older a RBC is the less G6PD activity it has, with young RBCs having essentially normal levels and old RBCs having essentially no G6PD activity. Thus, the murine models existing prior to the content of the subject disclosure fail to recapitulate the biology of human G6PD deficiency. The subject matter present disclosure satisfies these and other needs.

While specific aspects of the invention have been described and illustrated, such aspects should be considered illustrative of the invention only and not as limiting the invention as construed in accordance with the accompanying claims.

All publications and patent applications cited in this specification are herein incorporated by reference in their entirety for all purposes as if each individual publication or patent application were specifically and individually indicated to be incorporated by reference for all purposes.

Although the foregoing invention has been described in some detail by way of illustration and example for purposes of clarity of understanding, it will be readily apparent to one of ordinary skill in the art in light of the teachings of this invention that certain changes and modifications can be made thereto without departing from the spirit or scope of the appended claims.

What is claimed:

1. A transgenic mouse whose genome comprises the nucleic acid sequence of SEQ ID NO: 1 operably linked to endogenous glucose-6-phosphate dehydrogenase (G6PD) regulatory elements, wherein:
   i) the nucleic acid sequence of SEQ ID NO: 1 encodes a chimeric Mediterranean variant of G6PD (Med-G6PD),
   ii) the chimeric Med-G6PD is functionally expressed in the mouse, and
   iii) the mouse does not express endogenous or exogenous mouse G6PD.

2. A transgenic mouse whose genome comprises a homozygous insertion into the endogenous glucose-6-phosphate dehydrogenase (G6PD) gene, wherein said insertion comprises:
   a cDNA encoding an exogenous wild-type mouse G6PD flanked by recombination sites and operably linked to endogenous mouse G6PD regulatory elements; and
   a genomic region comprising exons 3 to 1 of the human Mediterranean variant of a G6PD (Med-G6PD) gene operably linked to exons 1 and 2 of the endogenous mouse G6PD gene,
   wherein
   the mouse does not express functional endogenous G6PD,
   the exogenous wild-type mouse G6PD is functionally expressed in the mouse and is capable of being deleted upon recombination,
   exons 3 to 13 of the human Med-G6PD gene operably linked to exons 1 and 2 of the endogenous mouse G6PD gene is not expressed in the mouse, and
   a functional chimeric Med-G6PD comprising amino acids encoded by exons 3 to 13 of the Med-G6PD gene and exons 1 and 2 of the endogenous mouse G6PD gene is capable of being expressed upon recombination.

3. The transgenic mouse of claim 2, wherein the recombination sites are LoxP sites.

4. A transgenic mouse that is the progeny of a cross of the mouse of claim 2 with a transgenic mouse expressing a tissue specific and/or inducible CRE recombinase.

5. The transgenic mouse of claim 4, wherein Med-G6PD is expressed in all tissues of the transgenic mouse.

6. The transgenic mouse of claim 4 wherein the CRE recombinase is an inducible CRE recombinase.

7. The transgenic mouse of claim 6, wherein the inducible CRE recombinase is a tamoxifen-inducible CRE recombinase.

8. The transgenic mouse of claim 4, wherein the transgenic mouse is an adult.

9. The transgenic mouse of claim 4 wherein the functional chimeric Med-G6PD has at least 40%, 50%, 60%, 70%, 80%, or 90% reduced stability or activity as compared to that of the wild type mouse G6PD.

10. A transgenic mouse whose genome comprises an insertion into the endogenous glucose-6-phosphate dehydrogenase (G6PD) gene, wherein said insertion comprises a genomic region comprising exons 3 to 13 of the human Mediterranean variant of G6PD (Med-G6PD) gene operably linked to endogenous mouse G6PD regulatory elements and to exons 1 and 2 of the endogenous mouse G6PD gene, wherein the mouse expresses a functional chimeric Med-G6PD but does not express endogenous or exogenous wild-type mouse G6PD.

* * * * *

SEQUENCE LISTING

<160> NUMBER OF SEQ ID NOS: 1

<210> SEQ ID NO 1
<211> LENGTH: 54980
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 1

```
catccacatg tgtgagtgca agcacagaca cacacactac ccaaaataaa atataacaaa      60
actttctgaa gagaaaaggc catgtgacaa gagagttagg gagcaccaag gcttgccaac     120
actaacaata tacttggaga agtacctgaa agagctctct gaagaacctg cctgcccata     180
cctttatctt agacctctga tctcaactag agacaatcct ctgttatcta agcccctgct     240
gtgtggtacc ttgctgctgt ctccccagat aagaatgaaa tgctttgaca aggcactctc     300
tgcatcatta tgaacttagt cccacaatat aaaacttgat tatggcaggt cttctctacc     360
ctttccccca gactggtcct ctcagatggt acaatccctg ctcaactatt gtcaccaggg     420
tcctgaaacc agccagccca aaaaggccct gtaatacccct ttcattccac actaggcata     480
ccatcctttg gtgcttgtgt aatacagggc caattcacag gcctagggtc tcataattcc     540
tccaaaggct cctaaggatc atctctgagc cccctgggaa atcctacctg atgtgactgc     600
cttgtttttt caggggccta ggactcaacc aggctgtctg ggctgatgcc agggtatgtg     660
agggccttgg actacatggt atagcacctg ctagacctca gggtggctag aacctgagca     720
agctagctca ggtacccaag cactccatgc cttcaaaagt gagcccagga caaagcctga     780
gcccaggaca aagcctggct cccagagctc aggactgctt cctggttgac aatgctctat     840
atacagtgca ccaccgttca cagcaaaagc actgctccct gagacgctca catctggcct     900
ctcctggctc ctaccatata tgccttgtac cttggaagat tctgatgtag agccttttac     960
tgtaataaac taacagttag tgtgatggct tctcttggtt ctaagagtgc tcccagcaat    1020
caagcctgaa aaggtcctga ggaaactcca acaacatact tcctacagga atatgagtgc    1080
tgctatggtc ttcaaacaca ggtggggcag aagggcctgc ccgtccacta gctagctacc    1140
tgttggcatt tcttcagttg ctccaactcc tttaaggcct gttccctctg actccgaaga    1200
tcaagcttct ccaagctcag tctctccacc agcttccggg cttcctggaa tttgcacata    1260
aggaactcct tctcctcccg ctggctgacc tggaaatgca gcagtcctc acagcgttcc    1320
ctcagcatct gattgctctg ccggatagcg tctagggaca gggaagacag caaaggagat    1380
aggagtccta acagccaggc actcctataa tactaagtgg cctttctcta agaagtcaaa    1440
ccaattccta gccagttcca ctgatgatat gcccccaagt gtctagaatg cgttactaaa    1500
cagagattct tcacttaaag gaatacacca aaatcaactt tctttttgcc cagaaggtgc    1560
agacagaaca agctagtagt tctgagtttc attctcttcg gctgcatatt gaagaacagt    1620
aaacatccac cttacaaatg agggtggcat gagaaagaag gcagtgccag tgcagaagac    1680
atactcaaag atctcctctc accagagctg gccatacccct tccaagaata ggacacattt    1740
catcttagaa aaaaccccctc tctctctctg aaggaaaacc atatcccctc ccacctaaaa    1800
gcttgctatg tcccaagaaa gaataaacct attctcattg cttcctatag cccactcttc    1860
ccctacctac catggctttt tagcttatcc tccttcccca tcccttctcc cttccctggt    1920
gctggctttg aaccacatta tcttctgcat gtgactcttc acagagaacc ctacttaaaa    1980
```

```
caaagcaagg tagctaagtt tgaaactctg gatggttctt gggcacatca tgacctcata    2040
tcctgccaat tacaagatgc aggtgacaat aagctttgtc cttatataag tatcccaggc    2100
tcctcctgac ttttaacttc atacctccct cacacatcaa tctttacctc ggagctcttg    2160
attctcttcc aggcagcgct ggagggtctc aggagtaccc tgctctgaag gcagatgtag    2220
cattgcaggc ttccccagag aagattcttc acccagcatg tcctggtcct ctgctgggcc    2280
accactgggc tgcaccatct cactcagctg gttcttccag gggtgcttgt tcatccaaca    2340
ggacagtgtc tagaagaaaa gggtagtagg agtgcatgac aaagaacaga gttcgttcaa    2400
ctagacttcc attcacagca aaaggatgga cattttgtct ggtggaacaa gatacaaaag    2460
tgaagtttgg gctaagacat agcaaatatt accattgcaa agagagagaa ttgtggagga    2520
gaggggaagt aaactgggaa tcctacctcc tccacacacc tttaagttga agcaaagggt    2580
cctggtccct cacccagtat agtggaatga ttgatatatc catgtcctaa tccctcaacc    2640
tataaatgtg attttttttt acttggaaaa aatggtcttt acagatgtag ttaaactaag    2700
gatttcaagc caggcatagt ggtgcatgtc tttaatccca gcacttagaa ggcacaatct    2760
ctgcgaattc aaggccagct tgctctacat agtaagaacc tgtctcacaa aaatcaaggc    2820
tctcaaattg agatcactgc aagttatata ggtgggccat gagcccagta acaagtacct    2880
tattactcaa ctagattgat ataaccacag gccaagaaac aactgagcta cccacaacta    2940
taagacacat gaaggatact cttgtacagc ttgcagatga agcataacct tgttcaccct    3000
ctggttttat tctcctggcc tccagacctg tgagatatca attttctgtt cttttaagcc    3060
acttggcctg tggtcacttc ttacaggagt caagaaaaca caaacacatg ataaaagaga    3120
cttcaggaga ccacattgta cctgaaaagt gttcactggg gatagagacc tcttgtgact    3180
tctttgctct aagaagtgtg aaagtgtgaa ctggggtgtc cgagacacat gaccccctgat   3240 ctgcttatgc tggcttttaa accagagaat atgcaggaca atactaacct ggagaccttg    3300
taaatcctgc ctcatactga caaccaggaa gagaatgatc tcaatgcaag tttccagaag    3360
tgggctttca ataagggaga cctcctgtaa cactggggaa tattggctat ttatactaaa    3420
ggtgttgcta cccataggtc catctgcctg agcccacaca actgaccctc cccacttttt    3480
cacctacttt cttccttcag gttccagaaa agccttctct gctggtgact cactccctca    3540
aaggctgatg ctgctcaggc ccttttcctg agtccccact tcttcacgtt gaggaacttt    3600
gggacttctt tcttaactgc attcacccct gcagtaattc catccggtct catggctttt    3660
aacccaaatc ttaatgttga taatatccca aacagttctc attcctaaat tccagatatt    3720
tataaaacta cttggatgtc tagaagtctt aaaagaagtt ggagagatgt ctcagctatt    3780
aggagcactc agtgctcttc cagagagccc aagttcagtt cccagcaccc atgttgggca    3840
actcacaacc ttttgtaact ccagctccag gggattagaa actcaaaggg aagggatcta    3900
gaagagactt tttaaaaaaa tattgaagta tgggcaaggg agacagctca gtggataaag    3960
gcccttgcta tgcaagcctg gagacatgag aacatataaa ggtggaaaga agatagctga    4020
ctcaatgttg tcctctgagc tctacacatt ctagccatgg cacctgtgct ccctgtacaa    4080
atcatacatc atgcatgcat gtgggggggca cacacacaaa tagtaatttt tgtagcatgc    4140
caattatgtc tcaagaaagc tgttattgaa aatcgcaatg ggtggagcaa gagagataat    4200
ggttcaggga ttaagagcac ttgttgttgc agatgtggct cacaaacatc tgtaactcca    4260
atccaagggg atctgaaacc ttcttctgac tcccttgggc actaggaaag catagcaaag    4320
cacctataca cataaaataa catcttctgt agaaaagaaa ataatcatgg taaaggattg    4380
```

```
taatggggtg tggattaaag ttaactatga gctgatagtc acagctaaga aatgtgtaca    4440
tggaatttac tatattatta tttctacttt tgtacatttt aaattttttc agtaattcaa    4500
ggctgacagc gctatcatct ttcacctgca ttactgcaat aatctcttta cgggtcacca    4560
tgctttgcct tttcaatggc cctttgcagt taattggccc cactgggcc aattacctca     4620 aaaataactc aaactacttc tcttctctac catgaactct ttcagagttt ccatttctcc    4680
tagtgttaaa aagcaaagtc catacaacag cctacaagat cctataccac ctatactccc    4740
ttccttcctc tccaccaact attctccctt gccctctctg gtccttcctt tttcctagga    4800
aatgccaaga caacacattc cttctcaggt cagataaatg ttatgaggac aggcaaacag    4860
attactatga atcatttgca aagtaaactg aggtgcagaa ggtaagacct ttagttgtga    4920
aggtacacgt gaaaactttt taaagacttc aaatgcactc aagtttgata acagcctag     4980 cctgatggcg aacacctgtt gctctagcac tcgaaaggct gaggcagaac tttgagttcg    5040
aggtctacct ggcctacagt gcaaaacgtg tttcagaaac agtttgatca acagaaaatg    5100
tctgctacct aaagagttct agcactaggg gccaagccct taggcgacag ctgcagtgaa    5160
gggaagggca gattcaatcc gactagccta aataatctgg gtagcgaata attagaagct    5220
tgcggcagaa caaactgggc ctaaggtggg gggaagggtg tggacctctg gagtctcgga    5280
agctacgaaa cagccaccga tggagccctg tctttggaga agaggaccac acctgtcagc    5340
agagtcggcc agaagtgaag agggcaggag cagagggatc cgaccgctcc gacagaaccg    5400
gagctcctag aaagtcctag tcaggcggtc acccttccct tctctgcagt ggaaaactcc    5460
acttccggct tccggtgtcg taagtgcggg atccggaagt aaaacacaga ctcaaaggct    5520
tggagattaa ccagtgaatc aaaaccccaa agtgccatac tctgttccaa agaaaagtct    5580
tagatcgcca gcctgcgtcg gccagcagaa caccagagct ctcctcactg ataaacatca    5640
cacacttata cacacacttt ttttttgaga cagggtccca taagaccagg gtctcgaact    5700
cagagatcta cctgcctctt ttttcccgtc tgctaggatt aaagtagtgc gtcaccacgc    5760
ccacactcgc ccctacccca ttttcaaggc accgcatccg cactaaaaca cccaagtttc    5820
agtctggtcc tgctactggg ctctctgccg ctggccccc accaaggaaa aagcctagag     5880
gaagctgcga aagtccagct ccgaagccaa actagcagct agggaaggcg tggctatgct    5940
gctaacggaa gtggggtcat ccgggaaggt gcagggcctc gaaggtccag cggaaagcta    6000
ggccatacat aatggctggg tgacacagga gacggggacc caggagaact gtgtggagct    6060
gcacttatga caagactttg cgatctcgaa attgtagggg cagcggcatc ggggaaggcc    6120
aaagggcggg gctggccagg gatgcgcgcg catctcctcc tgcaatgata gactagcccg    6180
aagctcctcc cctcctgcct ctcctgaggc gggtcagctc agtcaaagca cacgccctct    6240
tgcgttaaat gggccagcga agcttagccc ccggaaactg gctgtgcgct acagatctgt    6300
gaacgtgttt ggcagcggca actaaactca ggtaaagggg tggtctgatg gcatgtcggt    6360
ggagggacat gcttcacgct tgtacgccgc gagtcccttt gatgcgcgct aatctacaag    6420
tttttaaccc atcccttttgt atcccgcact ttccccgcat tgggcccatg aggactagac    6480
ctttagaaga gaagggactt tcggggatca cccaactggg ccagaagaga gccggagctg    6540
aactccatca tctgcacaat caaacgtgct cagttcattg tggagtttct ggcagacacc    6600
cgagtacgat acgatggtcc catatacaga gtgtgatgcc gtaaccagat tttatctagc    6660
tgcccacagt ggatgtccta ggtgaattat attaaagctt tagtactttc gtaatgtaca    6720
```

```
gcccctagcg aaggcaactt tggaggttat ggctggagct cagaggcagc agtttctgaa      6780
tctccgaatg catgtatgct cgcgcgcgcg cgcgcgcgcg cgcgtacaca cacacacaca      6840
cacagagcat tcccggccag tggttttagt aatcgtcacc agcctggtga gaacccaaaa      6900 gaccccttgga taaggttaag ttgtcaatgc tctttcgttc tcctaccata tcaatgagtc      6960
ttttcttcca ccagaaaaca tcatggcaga gcaggtggcc ctgagccgga cccaggtgtg      7020
tgggatcctg agggaagagt tgtaccaggg tgatgccttc caccaagctg atacacacat      7080
atttatcatc atgggtgcat cggtgagtct cccttcaggc cccgagtcta aagatgaaa       7140 tatagccttg tgcaaggcac ttctctctct ctatctcaac tttcccaatt gacggaactg      7200
ctgaggtacc cacaagttct actaggttga actctatggc atatactcca cctgtgtgtc      7260
ctgatcatca cagcagtacc tgatatacat gtacttgtgt cacatctcag aactctgtgc      7320
tgagccattg agtggagacc agacttggac catcacaggt gctaaagcac cacccagtag      7380
cacttcttcc tcctgatga aaaaaaaaaa ctgatgtgca atcagggaaa attctgattt       7440
taatgaatct gtaatttgaa aatattact gttaatttca gtggaagaat ctgaggtcct       7500
gcctctccct ctttttcttc tacggcatga agttccctag gataaacac ctcctctttg       7560 ccatatcttc caaagcctac tgcaaatttc tgttcatccc acctagtccc agctctgtta      7620
ggaaaaactg aagaacagaa gcagtcagag gggtgttgta ttgacagtac acagtgagac      7680
tggagcaggt gggggcttag taaagtcatg cttagacca aatcacccccc ttatgtgcta      7740 tgtggcagca gggcacgttc agtggccagt gttcgatggc aaaggtaaac tcaattgctt      7800
gcttttaatc ctggaatcag ctcaccctcg tgtgaccatc ttcactatta acttattgtg      7860
taatcttgga caagaacttc atcagaacta gtgtgttctt gaagggtag ccactggctc       7920 agcaccttcc accctggacc cctcaatgct ggaggagctc tgtggttttt tgttcacaca      7980
gagcattgcc atgcaccaag ggctacagct gtaggtcagt ggtaaagccc taacctcata      8040
tgcatgaggc cctaggttca atcgcagtac tatccaaaaa atggacatca gaacatgcca      8100
ccccctttgc cagacttgtt tgttgtctgc cttatatttc tgagcaaaaa tgggagtggc      8160
agaacttcga aaaggaatgc agaaacaagc tgaggagaag ggccctgcca ctgaaagggg      8220
aagggacaga caaaccaaag cactgtcccc tggctccttg tagctctaag acctaaggga      8280
ggtacttagt cggaacacac aatacagcag ccctaccctc agccctgtct ctagcctagt      8340
ccccttaaag gagctatgca tgtatctgcc acaaaccta gcatgtggga ctctgctttc       8400
agtctaaagg gccaaatgga agagaaagta actgaagatt attccccctg ccccacccat      8460
gctttcataa gcatgcagca acaataaccc agtcatcgaa gatcattttt aactgtagga      8520
catgaactct tagatacctt gttgatagct tattatgtga cctggaacaa atgtctacat      8580
ttctctgaac cctggtgttt tcatctaac aaacaaaaac caggcagctt ttctggcttt       8640
atcctaggct aattatgtga attctagcct caagttgagc aacttccttt cactgcaatc      8700
agtttggttc cctttgctc tcctctgctc tgggagtaag aacccgggct tccagagtag       8760
aaataggaac tattagttcc agcaaaaggg agtggggaag aaagagattt tctaaaaagc      8820
atcattgttt ctttctgttc ctctcagagg tcctgagaga gagagacaga cagaccctat      8880
gcttagcccc tagagtagct cctgcctgat acttcactaa atgcaggtgc tatctgatct      8940
aggacacctg caagttctcc attcattaaa cgtagcaatc aagtgtctcc cattacataa      9000
tagtctcagt tcctatcctc cttgtgggga cagtgtactt tggggagctg catgtaacag      9060
aagtcacaaa tggattcttg tgtactaagg cccctgcaac acacaggtcc caagaggacc      9120
```

```
taaagagcaa ggcaagttga ggataagggc aactgccctc taagtttgga acaagctcaa    9180
tgtgacctag aaactaaaag gaagctagtg gctggcaggc ctcaagccta ggaaactgga    9240
acaaactagg gcaagttgat cctaagtagc catcctctgc cccttcttcc tccccaggtc    9300
cttacccagt ccttacacat gtacccagct tccttggtgg ggacattctc aatgtgcctc    9360
actgtagcca ttcctcttct cagaactccc accccaacaa gaaagtgaac agaaatcctt    9420
actgtcccac tccttatgga ccagtgcagg gaaggaactg agcctagaag ggcatctccc    9480
ccagccaata ggaccttggt gaaactagag agtgagtgag tctttctcct atgcagaaga    9540
aatggagtag gtctgggagt ccacatgggc agataagctc actatgggcc catctctcta    9600
gacatctgat tccttaccta gcctatgtga cacccataga ttcagtgagc actcaaggtc    9660
catcctgctg acaggactgt gtgaggagtg acctggcagt cccagcccat ccctctactt    9720
gggtcatttc tgagctgact tctcccttga gctggtaaga ttcttgctgt gtcatgatga    9780
ccttggcatt ctcccaaaag cctggtgact cacagagtgc cagggtgtaa gaaggaggcc    9840
ttttgttaga tttttagccg agacctacct cgtatctccc tatatctcat tcagtgcctg    9900
gaaaatagcc gaccctcagt cgcagtcttc acagtctaga actgtgtctt ggaaagctag    9960
gtgggtccct catccccaac aactcttggg aactgagtgc ctcactcctg caaggccttc   10020
actcgaattt ctcccaaaca aaaggctggg tatgatttga cttcaaaaaa caagaaccca   10080
aacctcagct aactatagac caagtggtac tcagggtctc tttgccttta tctggccaga   10140
tatctgtggc tagagatctt aatcatgtct taattctcct aattcaccac atatccttag   10200
gtagatcctt ccccgccat ggtacttggg caatatgagg gggtagcaaa gatgagagac   10260
ttccagccgt ctctctaatt gcccctactc ccacacatgt taagtttaga ttttagttct   10320
tctcatgttc cttacttcag aggagtttag tgagagtcat gaagccaaca ggaaagacag   10380
ggtgatccca tccctgagaa gaatggctac ctcccacccc cactgtcctt agtcctacct   10440 cacctcccctt gggtgacttg aagccaggca gactgtcagt tgcaggctga gccaaaacaa   10500
ggagagcagg ttctatgtct tgttaatccc aaagagaaca agaacaaaca gctctgggtg   10560
tggggcaact gtgactcagc agaccagtcc cctgccacca acacattggc tggagtctgt   10620
actgattcct cccagttagt tggaatttga tcataagcaa acactgtctg cttagaaaag   10680
tctacaagcc agggttctca ttgtttcttt tagtttctag ttcccagcaa gccagtcctt   10740
tccagagtgt gtgaggacag gataaaaccc tctgaacatg agcagtaacc cacatcccac   10800
tgatggaaga tcatagaggc aggcattgag agcattctga ggaactaaga accatcctgg   10860
ggggaaatcc tggcccagaa ttggacttgt ctatgctggg cttttgtggga cctataaggg    10920 caaccatctt gcacaacaga gtaaaagctt tgcccagcag agtgacttgg gggacagtaa   10980
ttaggccact caggtggcca tgcttggtat cacatgagga agtgacagat gaggaggctc   11040
cagagcaata gaagcccagc tggcagcaag tcttagacat tttcctaaag atagtcatag   11100
cattgaagtt acttactggc cattgggctc aggctcccag aagttcatat ggaaggtggt   11160
agttatcata ggaacccact cgccaatgct caggacttta attctgagca gttgacagac   11220
atgggcactg aattgctcgc tcatgccaac acagggtgtt agggtttggc aacagtcctc   11280
tatgaaagtt ttgggaaccc agaacctaga aatgacatgc acacaattga ttccatggac   11340
cggtcactca gcaaacccct gagaacaaac attcaagcca tgggaatccc tgagtgccca   11400
taactatcct tatccagaac tgccatttcc catagaaatg ggctcatcag tgcagctaca   11460
```

```
tggttaactc tcttttgttt gttaatatgc taaccaagtc tactcagcct cagccttccc    11520
tgagcctctg ctccccttt  ttttttttt  tttttttttg agacagggtc tcactacgtt    11580
tcctgggctg accttgaact tgttattctc ctgtctcagc ctcccaagta ctgagattac    11640
aggtatatac tagtcatct  ggctaagtca tttttgaagt ttggatcaaa atggtattac    11700
cactacaatg ttttgatttg atttgattca ttttatgtac ataggtattt tgcctgcgtg    11760
tatgtctgta ccacttgcat gtctggtgct ctcagaggtc agatccctaa aactggaatt    11820
acagaaggtt gtgaaccacc atatggatgc tggaaatcaa actaatgtcc tctgaaagaa    11880
tagcttagtg ctgttaacca ccaagcaacc ttcccagccc cacctcttca ttttaaagag    11940
ttagtcagct taggctatgt aatcagcttg ggctatgctg tatattagtt ctacctgtga    12000
taacagaaag ttgcctatta aatattgtac taaagagaac agcagggctg agagatggc     12060 tcagtggtta agagcactga ctgctcttcc agaggtcctg agttcaattc ccagcaacca    12120
catggtggct cacaaccatc tgtaatgggg tctggtgccc tcttctggtg tactcatatg    12180
cataaaataa ataaataaac ctttaaaaag agagagagaa cagcagttca ctctctgggg    12240
gtccctgatt catggagccc agcatctttc caggtgatgg tgatcccagc caggtaaagg    12300
aggattgttc gagctgtatt ctgcatagct tatttaaatt ttgcaaggtt catgccaccc    12360
agacccactg catctaaaac ctcatcccaa acacctgaga aattagtgcc aaaatgcctt    12420
gttagaaagt ggtgttttga gttttaatta gatatacctg tagtaaaagt ttcagcaaat    12480
tacttttgta taaatattca ggttcttaaa accagagttg ctttttgtgt agagagtgaa    12540
ttagaatata gatgggacca gtgcctgact ccagttgcac ttgctcacct ctccccatga    12600
agtagtacta tcctgtgtgt gtagcatggg ttcacacttc tcccacgttc ctaattatag    12660
ggtttgagat gaaagggcaa atgccctact ctattccaag agattggtag tcatgtctgc    12720
cccttcttct tgtacctggt ttggcagggt acaaaatgaa agcatgttgg gctgttactg    12780
attactggga tactgaactg agtgtgcaca ttagcttgga aatgaggatg gtgaacttat    12840
ggctaggttc tttataatat ttacttttgt aaatggtatt gttttaaatt gctaattttt    12900
ccaactcact ggtaaatgag ttttatttac tgttagtaaa taaaagttgc tagcttgtat    12960
ctactaatat ttacagtggg ttcttggggg tgctgtttgg tttattcatt agctttgcag    13020
tgttacagat caaacccgtt gcctaacact tgaccactga gctatatcct tagccccaaa    13080
tatttataat tcttattgga atatttcatc aaaaataaca cagaccttaa gggcgcagct    13140
gggcaacttt tcacaaactt ggcacaccct tgtaaatttc tctccccatt aagaaagggg    13200
gcttgaaaga tgactcattg gttaagagta tttgctactt ttgctcaaat ccaagtttag    13260
ttcctagtac ccacaacagg cagctaataa ctccttataa ctcccaatcc aggggatcca    13320 gtgcccttttt ctgccttcta taggtacctg tactaatgta catatacacc ccccaacata   13380
cccatacaca taattaaaaa caaaataatt acttaaataa aaagaagaaa cagagtatta    13440
tcacctaaaa tcttagcact gcagaggctg aagcaggaga ttcacttcaa gaaagacatt    13500
caaaactagc ctgcctaagc aacataacaa gaccctgaat taaaacaatg taaaataggg    13560
ctggtgagat ggctcagtgg gtaagagcac ccgactgctc ttccgaaggt ccagagttca    13620
aatcccagca accacatggt ggctcacaac catctgtaac aagatctgac tccctcttct    13680
ggtgtgtctg aagacagcta cagtgtactt acatataata aataaataaa taaataaata    13740
taaaaaaaaa caatgtaaaa tatatggtgg tatacttctc ctgtaattct agaaaggtgaa   13800 aagaaggagg attaggagtt cagagctagc cttagctaca tagtgagctt gatgctagtc    13860
```

```
taggatacag gaaacccagt ctcaaaaaaa aaaatgtttt taagtaacta aagccaggtg    13920
tactggtata cagttgtaat cacagcactt aggaggctga ggcaaaagga ttaccttgag    13980
tgtaaggaca gtctgagcaa catagcaagt tcaaaactag ttaggattac atagcaagac    14040
cctgtctcaa agctacagca aaaaaaaagg tatgtaccca agaaccccc actttgtagc     14100 tattgtttcc ctaggagtaa tgtcaaactt cctctccacc ccctgctcaa ttattttcac    14160 cctctttttct tggtacatat tgtaatgcat aaatggtagc tatattgttg atgacctaat   14220
ctaggacatt tctgtcttcc cacacaattc ttggatacccc ctggccagcc agtctaccgc   14280
ctctctaggc aactactcat ctgagtcctg tcataatagt ctaaagttgc ccattctggg    14340
gcttttaagt gaattcatta gtatatagtc tcttatgtct agcttctata gttcatcata    14400 atatatttt aagatttgcc aacactgaaa tagtagctca ttcctgagta gctgaataca     14460
gatatacaat ttgtccatct gcatgctggt ttatttgacc atttctgggc tattttaaat    14520
taaagctgcc atgaacattc atgcacagat cttgggcag ctggttgcct gcttttattt     14580
ctctggagta acacctagat attatagcta cttcacctga taagaggctg ccatgctgtt    14640
ttagatttaa tcattgcagg tttctacaca cagtctatga gttccatacc aatactaggt    14700
cttccttttg ctttggcttt tgcgggaag ggagttctat aagtatgtac caactatcat     14760
catttgtatt acagtcattc taatgagtct gaagtagtgt cttgttaaag ttgcattttc    14820
tgatacctga tgatcttgaa catttcccat gtattttatg gccattcgtt tccattctgg    14880
tgaaacatct ggccaaacct tttacccatt tcagttagat tgttttttcag tgtgtcatag   14940 gagctactta gatattctga atacaggtaa gtttagtgaa tactatctct aaggttgaaa    15000
cttgtctttt tggtgctagg gattatactc tgggccctgc ccatgcaaag cacataccct    15060
accactaagg tcataatgcc aggcttgcct atttttcttc gtttctttg tttcataata     15120 ctggatattg aaccagtcat atgcatgccc ttcattttt tcatatctct ctttcctctc    15180
ctatattccc taccccagt gcagaccttg agcccttat gtatccaagg ataatcctga     15240
agttcttatc ctcctgcctc tacttctgga atgctatgat tacaggctgc agtacaatgc    15300
tggcttatga ttattacttt atatcctaag aaatctctac ctactcctat cacttttta    15360 atctagcaac ttggaaaacc ctcattaatt ctaataatta gtctgtaggt tgatttgagg    15420 tacttttta aataaacaag ctatcatcta ataatgacag gttttttgtcc tctattccaa    15480 accttatacc acttcttc ttttttcttt ttttttttt ggttttgttt ttttgagaca      15540
gggtttctct gtgtagccct ggctgtcctg gaactcactc tgtagaccag gctggtcttg    15600
aactcagaaa tccacctgcc tctacctccc aagtgctggg attaaaggcg tgtaccacca    15660
ccgcccggcc acttttcatt ttcttgtctg atgacactat caagggcttt tagttttaaga   15720 ctgactaaag aaacaatagc aagcatttag aattttctca tagacaccta gatgcgtgtc    15780
tgtgattgtg tttaaagaga aatttaactg aagaagagag acctaccatg aatttcatag    15840
aacacactat tgattggtgt ccctgagtga acaaaaggaa attggagaga gtaaactaag    15900
tgtccatatt catctctcgg cttccttgtt gacaacacaa acttcacccc ccatcaccac    15960
gccttccctg acatggcaaa ctgtaccctc aaactgtaaa cctgaataaa ccctcatccc    16020
cgaaatttct ttctgccagg tatttttttt tcatagcaac aagaaaggta aacaataccc    16080
cattttgttt gttttgtttt tgttttcga gacagggttt ctctgtgtag tcctggctgt    16140
cctggaactc actttgtaga ccaggctggc ctcgaactca gaaatcctcc tgcctctgcc    16200
```

-continued

```
tccctagtgc tgggattaaa ggcgtgcgcc accacgcccg gctcagaacc ccattttgaa    16260
tggtgttttt agggtgtttg gtagatgtcc taaatcaaat taaagagatt ttattccctc    16320
tttgattaaa aaaaaataaa tagaattttt ttctgaaacc ctttatctgt atttgttgaa    16380
cttaacaaag ttgctatatt ttaaaaatca gtacacagac atgaagattt ctcagaggcc    16440
tattgtaatc acagcttctc aggagtctgg ggcaggcatt caaagctaat gttgactaca    16500
aagtaacttc caggccaacc tgagtaactt tttgagactc tgtctcaaaa gataggcaaa    16560
catggtggta catgcctttt taatcccagg aagtagagac aggtagattt ctgtgaattt    16620
gaggccatcc tgttcttctc agcaagttcc aggtcagcca gggataagat ctgtgactgt    16680
cctagttagg gtttctattg ctatgaccaa aagcaagttg aggaagaaac agtttatttg    16740
gcttacactt ccacatcata gaccatcact gaagaaagga aatgaacctg gatgcaggag    16800
ctgatacata gaggcataga gggatatttc tttttttctt ttttgttttt ttttttttgg    16860
tttttttttt tttggttttt tttttttttt tttttttttt tttttggtt tttcgagaca    16920
gggtttctct ttatagctct ggctgtcctg gagctcactt tgtagaccag gctggcctcg    16980
aactcagaaa tccacctgcc tctgcctccc gagtgctggg attaaaggcg tgcgccacca    17040
cgcccgtcga gggatatttc ttactggctt gttcagcctg ttttcttata gaacccagga    17100
ccatcagtca aggttggtac cacccacaat gggctgggcc ctcccacatc aatcacttaa    17160
aaatgtccca caggcttgcc tacaggctga tcttatgaga gtattttctc aattgaggcc    17220
gcctcctttc tggtgactct agcttgtatc aagttaacat aaaactagcc aggacgggac    17280
tatagtccag tagttgagca cttgcctaac atgcttgatt tcctgagttc agtcaccagc    17340
gccatacaca cacaatggtt ttttcagaat ttttcattta atttcttttg aggggtattg    17400
gtttttgttt ttgttttgtag acttggtttc tttgtatagc cttagctgac ctggaactca    17460
ttctgtggac taggctggct ataaacttag agatccgcct gcatctgcct tccaagtact    17520
gagattaaag gcatgtacca ccactacctg gctaattttt ttttaagatt tatggttttt    17580
tatttatgtg tctgtctgcc agccagtcag ccacatgtgt atggataccc acaaaggcca    17640
gaagatgtca ttaaattccc tggaactgaa gttacaagca gttgtgagct gcctgatatg    17700
gatgctgaaa accaaacttg ggacgctgta caaaaccagc aagtctctta atactgagca    17760
tctcttcagc ccatttttaa atcttttaat gtgattttca gtgattgatt ttgtcattgc    17820
tctcgctacc tttattcttt gagacaggaa ccctcattga acctgcagtt catctgtaca    17880
gccaggccag ctgacaaatg agttacagga ctatatagaa aaactctgac tcaataaaca    17940
atcaatcaat caatcgagtt ttacatcagc ctttgtcatc aagttgtaga actaaagttc    18000
tcaaagtgcc cttagaagta ttcctcttta ttctgtcttc aggggaaatt tacttcagag    18060
tggaattcac tcttccttga ctctggtaga agccattagc aatgcttttc aggccaggag    18120
ttgtctttgt acattgccac cccttaggtc cattcctcca ttatatccta ggttggatct    18180
tttttttttt ttaaagacat ttttccatct tgctgaatat ggtggcacac atttgtaatc    18240
ccactacaaa gaaacaagag ggttgtctgt agtttgaggc cagccaggac tacatactga    18300
atttaagacc aacctgggcc tttattccca gcactgaagg acagaggcag gtagagctct    18360
cttgagtttg aggctagcct ggtctacaga acttccagga taaccagagc tacacaaaga    18420
aaaccagact tggggatgga gggtggacgg taccaacatt ggttacatgg caaggccctg    18480
tcttaaaaaa ataaaattaa aaaaatttt aattctgtgt ctcagctagg ctgtagtggc    18540
acacacattt aatcccagca ctccggaagc agaggcaggt ggatatctgt gagtttaagc    18600
```

```
tcaaccttgt ctacaggatg aatttgaaga cagccaggac tatacagaga aactctatct   18660
tgaaaaaaat aaacaaaatt ctctgtctca ttctaacttg ttagggtttt gttaggctgg   18720
gttgggtttt gttttggatt ttggtggtgg tggtagtgtt tgagataggg aaagggtctt   18780
atggtgtata cctaaggctg actttgaagt ccagatcctc ctgctccaac tacccaagta   18840
ctgggattat agacctgtgc cacgaagccc agcttttctt tcttgttttg gttgtttagt   18900
ttggtttgat gtttggggaa gttggtttta ttttggcttg tttttttttaa tagctcttaa   18960 tttattcttt gagaatttca tacatgtata caatgcattt aaagcatatc taccctccat   19020
tctctctctc tcaaccccctc tggacaacct ccccgatccc ccacccaatt tttatttttg   19080
ttataaccca ttaagtacaa taattgcttc ctacattctc atgagcatgg aaccatcatc   19140
cactccttga gcaattacca aggggccatg aagaaaaatt atattcccta gcagccactg   19200
atgggaagtg gatcttccaa cagatcctta gctagggta gcagcttgtg aactacacac   19260
actcagcatg ctggccaact tgatctcatg caggcaacta cagctactgt ggcttcatgt   19320
gtaccacagc cctgtcatat caagaaaata gcaattcaca gctctcctct agcgctcttt   19380
tgttagtttt ctactctgtt tgtttttgta gggtgggggt ggaaatcaga acccttgcct   19440
actccaaaat cactgagcat cttctccagc ccaattttc cattgaattt tttcactgct   19500
acctattttt ttttttaatt ctgatttaga agaggtgatt ttgaaacagt atctccctca   19560
atattgggag aatatattac caccaaatct ggcctttgtt acagagacaa gacttcattc   19620
tgcatcatca aacttttcct gccattattt ttctaacttt ccaaattgaa tgaccatctc   19680
attgccttct agctccggtg acatctgagg ccttacctca caggttttgt ctttctttta   19740
tgtgctgcct ttatcatcct taagctctaa tgaattcgat gtctagggtt tcatcttgaa   19800
cccagcagtg tcatctactc atctgtttaa ttaagccaag caggcataac ttcgtatagc   19860
atacattata cgaagttatg atctaaaggc ttgaatctcg ggctcttct gtctgtatat   19920 caggcaagac agacatgctt gtggcccagt agtgatcctg agtagtgccc agatcaccaa   19980
gggtggagga tgatgtatgt aggtcgtgtc cccagccact tctaaccaca cacctgttcc   20040
ctctgccaca gggtgacctg gccaagaaga agatctaccc caccatctgg taagtgtgtc   20100
ccaccactgc ccctgtgacc tcccgccagg acaggcctg gtcctgccct gcccgcactg   20160
gttacagctg tgccctgccc tcaggtggct gttccgggat ggccttctgc ccgaaaacac   20220
cttcatcgtg ggctatgccc gttcccgcct cacagtggct gacatccgca aacagagtga   20280
gcccttcttc aaggtgggtg gtgtcagggc ctcccccagc ctggttctgc cctctctacc   20340 agccccagc atggccagct tcggggacct ccccccatcc catcccggga tgctctcctc   20400
ctctcctgcc ccgcccgcc tgctctcgta cttccttgag acccccatta ccagcccccg   20460
tgaccaggac ccacaggtcc cctcctgctg tgctctgctg cgttttctcc gccaatcata   20520
gttgggtgtc atgattttgg agagagagct ttctccagtg tatttctccc aggtcaaaat   20580
atcctgaaat ctggcctctg tcctaaggca caggggtccc agcctggggc agtgtctgtg   20640
ctgcctgctt tggcctccct ccctctggat gtgcagagct gctaagatgg ggctgaaccc   20700
agtgtgggac ggggacactg acttctgagg gcaccctccc tggacctcca gggaagaccc   20760
tccactcccc tggggcagaa cacacacgga ctcaaagaga ggggctgaca tctgtctgtg   20820
tgtctgtctg tccgtgtctc ccaggccacc ccagaggaga agctcaagct ggaggacttc   20880
tttgcccgca actcctatgt ggctggccag tacgatgatg cagcctccta ccagcgcctc   20940
```

```
aacagccaca tgaatgccct ccacctgggg tcacaggcca accgcctctt ctacctggcc    21000
ttgcccccga ccgtctacga ggccgtcacc aagaacattc acgagtcctg catgagccag    21060
atgtaaggct tgccgttgcc ctcccttccc gcctgccagg ctggcccagg cagtgctccc    21120
accactctat gagcgtgtcc ggggccgggg atctgggcag catccatggt gccggggcca    21180
tccccagcgg gaccacaagg tggcagcgtt gctccacgaa acaccgcctt ccgctctgc     21240
ttccccaaag gccggccag gccgcagggt ggcagccttg ctctgcgaat gcagcatggc     21300
ccgcgctggg tggtttccca acccagccag aggctcttgt cctctggctg gttttgaatg    21360
cgggggtagt aaagcaaagg tcctctacgc gttctcattt tcaaaaccaa tgaggaagcc    21420
atggcttgga tgcctcctcc ccctgctccc ctacaggcct tcaggccact cagacccacc    21480
ggggacccag catgaggcag gaggggaacg ggccccccgg c agcatgccag caatgccacc    21540
ctggcaccca gggtgggaag gcttcccgga aggtgttgag ccagagggtc atctgggaac    21600
acaaggcacg ggaggtggcc acgggggcga ggaggttctg gcctctactc ccctgggagg    21660
gcgtctgaat gatgcagctc tgatcctcac tccccgaaga ggggttcaag ggggtaacgc    21720
agctccgggc tcccagcaga ggctggaacc gcatcatcgt ggagaagccc ttcgggaggg    21780
acctgcagag ctctgaccgg ctgtccaacc acatcttctc cctgttccgt gaggaccaga    21840
tctaccgcat cgaccactac ctgggcaagg agatggtgca gaacctcatg gtgctgaggt    21900
ggggccaagc ctgggccggg ggaccagggt ggggtggta ctcaggagcc tcacctggcc     21960
cactgcctcc ccgaggacga attcctccag aactcagaca agggtgaccc ctcacatgtg    22020
gccctgcac cacagaggcc caaggtcagt tcctccacct tgcccctccc tgcagatttg      22080
ccaacaggat cttcggcccc atctggaacc gggacaacat cgcctgcgtt atcctcacct    22140
tcaaggagcc ctttggcact gagggtcgcg ggggctattt cgatgaattt gggatcatcc    22200
ggtgagagct cttcctctct cctgggaggc tggcacaggg tggcagagcc agtcaccctg    22260
cagggctact cttccctatc ttgggggagc tcctcctcac cctgcagttc aaaacctaag    22320
tgtctgagct atcagaccgg ctggaaagg gctggacccc tacacagcca agcaccccac    22380
ggttttatga ttcagtgata gcatcaccat gtccttcctt gatttaaggg gacctggaag    22440
acaaggggga tcaggaagtg agtcttgcag cttgtcacta ggaagccttg tttggggtcc    22500
ccatgccctt gaaccaggtg aacagggcgg ggagctaagg cgagctctgg cctcttccgt    22560
ccccagggac gtgatgcaga accacctact gcagatgctg tgtctggtgg ccatggagaa    22620
gcccgcctcc accaactcag atgacgtccg tgatgagaag gtaggggtg caccccagtc     22680
cccaggagca tgccctgtcg caggcccatc tgtgacgagg cactgagctg gggtgtgcat    22740
gcagagcagg tgtcctcaac cccggagaag tcaccacctc tgagcacagc gtggcctccc    22800
ggaggtgacc tggactggca gtcatgaagc ccaagttgtc atgtcccagg cctgacagtc    22860
actatgtgac cagggaaggc cattgcctct ctgggcctca gcttgttcat cagaatagac    22920
tcgagatgga ccagggtggt cctggagggt cctcaggag gggccctgag ctgggcctct    22980
ggcagggtga gcagagccaa gcaggggcct cctcctgccc tgagggctgc acatctgtgg    23040
ccacagtcat ccctgcaccc caactcaaca cccaaggagc ccattctctc ccttggctt    23100
ctctcaggtc aaggtgttga aatgcatctc agaggtgcag gccaacaatg tggtcctggg    23160
ccagtacgtg gggaaccccg atggagaggg cgaggccacc aaagggtacc tggacgaccc    23220
cacggtgccc cgcgggtcca ccaccgccac ttttgcagcc gtcgtcctct atgtggaaa     23280
tgagaggtgg gatggtaggt gatgccttcg aggcccagca aggcagaact gggcatgccc    23340
```

```
tgtgtgcggg cactggagct cccactgaga cactcacgca ctggtccaca ccctgagaga   23400
gctggtgctg aggctgccct ttccgccacg tagggggtgcc cttcatcctg cgctgcggca   23460
aggccctgaa cgagcgcaag gccgaggtga ggctgcagtt ccatgatgtg gccggcgaca   23520
tcttccacca gcagtgcaag cgcaacgagc tggtgatccg cgtgcagccc aacgaggccg   23580
tgtacaccaa gatgatgacc aagaagccgg gcatgttctt caaccccgag gagtcggagc   23640
tggacctgac ctacggcaac agatacaagg tgccctacag agaaggagca gtgtggaggg   23700
tgggcggcct gggcccgggg gactccacat ggtggcaggc agtggcatca gcaagacact   23760 ctctcccctca cagaacgtga agctccctga cgcctacgag cgcctcatcc tggacgtctt   23820
ctgcgggagc cagatgcact tcgtgcgcag gtgaggccca gctgccggcc cctgcatacc   23880
tgtgggctat ggggtggcct ttgccctccc tccctgtgtg ccaccggcct cccaagccat   23940
actatgtccc ctcagcgacg agctccgtga ggcctggcgt attttcaccc cactgctgca   24000
ccagattgag ctggagaagc ccaagcccat ccctatatt tatggcaggt gaggaaaggg   24060 tggggggctgg ggacagagcc cagcgggcag gggcggggtg agggtggagc tacctcatgc   24120
ctctcctcca cccgtcactc tccagccgag gccccacgga ggcagacgag ctgatgaaga   24180
gagtgggttt ccagtatgag ggcacctaca agtgggtgaa cccccacaag ctctgagccc   24240
tggaaggatc ccatatgggc cggccgttac accatctata ctctgcctct tctgccacc   24300 cttctgcat cttccctttt caccatctaa ccctatatta ggactattga ccccatattg   24360 gaaggactt gggaccatag gccttagata cacattctag ttcctgggct tggaccgcca   24420
ttttgtccta tgctgctgcc actgccacca ccagtaaacc cagctacatt cctcaaatac   24480
caggcattta aaactcattg tagggtttca gggccaccac tggccctatc tgagccaccc   24540
atctttccac aagacctgaa tcacctccct tccagccgct gcagaaagaa tgcctatcag   24600
tctgcccctg gactccttaa ggagttagga caatgggga ggagcttag gcctcaaagg   24660 gacaatgacc aaaccagact tcccagaggc tatgggcaag ctcctcaaaa cttgaaggaa   24720
gtggtcaagg acacctatgt gagaggacct gcccatggcc acactagcct cagtgctact   24780
agacattcct cctcaccaga tggaagagac ctcatgctgc ctagcaatat tttgggggct   24840
ctagatgtcc cctgaccaat tccatactcc atggtcaacc tcatcccacc tatgggcagc   24900
ctccttacca aggaaggca agcacagcag ctagaatttt cctatcccaa ccctgccatt   24960
aaatcctcaa aacagtttta cctgtctcct tgttctttc tccttgcatc caggatcatg   25020
aaggagagac ctattatttc cccacttccc acatttgtta ttcagggttc tataaaagaa   25080
cagaactgat aaaacatata ctagagttgc ttagaagcta cagtccaaat agtccaacaa   25140
tggctacata ttttgaggaa acacctgaag ctgatgctag agcagtctct taatttgaaa   25200
tcttctgagg gctcagtagg actgagaagt tttataactg ttgctttata ccatgcagtc   25260
atctcatgct ggctttgaaa tcacaaagct ccacctgctt ctgactccca agtgccaggc   25320
ttaagggtgt gtatcacaca ctatagaata ttttattct tttcaggcat gacagttaca   25380 cttcttttg gggttttttt ttttgtgttt ttgttttgtt ttgttttttg tttttttgt   25440 tttttgagac agggttctc tgtatagccc tggctgtcct ggaactcact ctgtagacca   25500
ggctagcctt gaattcagaa atccgcctgc ctctgcctcc cgggtggtgg gattaaaggt   25560
gtgcgccacc atgcccagct gacagttaca cttctggtca gtgtcctcca gagcatccat   25620
caaggttcca tagacaagat tggaggccag gctttaacac agggacaggc ccttcattct   25680
```

```
ccatcctcct ggtgtctatg cctcagatgg gtgagctgat ggtgccactt agattgggcc    25740
tgagagctgg cagggcaaat gtgtgcaaca actctggggc taaaagctgt gtgctgagct    25800
atggaggctt tctagcctag cctcaccact tttaccacag cccatgaaaa agcatgtaga    25860
aacaagtaga atagcttctc agggacttgg cacaaagccc atgtgaggcc tcaatgccac    25920
ttccactgtc atctcctact gactctcatg aattttaatc ttcccatcat gtttagataa    25980
aaggccacac ggtttctctt gactcctggt acagcagtca tgtggttaca gtgaatagac    26040
aaggttttac aaaaggatag tgaagatgta aagcctgtca acgcccaaat ggcagaatct    26100
tgtccatctt ttcctaaagc tgcccccaca ccttcctcca cacattacca aggggtacca    26160
gactcatgcc tgttttgggg aaagagcctt ttaaaatcct caacctcttt gaatggttag    26220
agtggatttt caaagcctca gatgttcacc tgagggtggt atttaaagct ttagggcaag    26280
ggaaagcaga caaaggcacc agaaaatggt actgaccatg tggaggctct ttgtgcttag    26340
agtactgttg aaaccctcag gttgcacccc aacttttaca gactttggga gtagagaact    26400
tgctggcata gtgtccctaa agcagaagct actataaagg ggcagcacag ggagcctaaa    26460
gtacagaagg gacatgggag taatttgagt aagaaagaag aaggactgaa gagagcaacc    26520
tgaccctaca ccaaagctct attgagtaca ttctactttc accttacctc tgggtgtgtg    26580
tatgtatatg tatagggtgc ccttactaaa ctcaggtcct ttgcaagacc agcaggcaca    26640
cctaagcact aagccatttc tccagtacat tacgttagtt ctgatgcaaa cattagtgct    26700
gagattcatg gcctaatctg cagagatcaa ctgacataga atctctatat gcctacactg    26760
gatgaaacca gaaacttgta ggtggaacag tcaactgtaa ccgcaggtat ttgtagctac    26820
actagagtag agacatttta agtctgggtt acattagctg cctctggatg agaaaactat    26880
agtagtacat gaaggcccag gtgaagttgc ctttcacctt ggctccaggt ccaagcgata    26940
gcattcaagt gaaatccaag attttggtcc ccacattgga cagaatgaag gagtaagtaa    27000
agtcattcag ctaccacttc aactctagga cacaaaaaca caggtgggga cacaactgtt    27060
gcctaaatct tatttaatac tagggtaagg taggataaca taaagcacaa agagaggtga    27120
ggacattcag ctgatcactc agatttaagt ccctaccaag gaccaaaggc acaataagcc    27180
agcagcattt caggaatgat gacacaatca ttcaacaatg aggctgttga gggaatcttt    27240
ctggaataag ccctctgaca ccaatgagag taaaagagaa atgtccccaa taggatgaag    27300
ccaggacagc tcctgaaagg ctttaatgct gggtctaatt tgtgagcagg tctttacaaa    27360
agtatgcttg gcagtcagca tgttgttaag agcaatgacc cattgtttga gctatttctc    27420
caggtcattc tgttccaggg agcaactgaa gtcatggttg gcaaataggt aatacagcag    27480
tgatataagt aaatcagtaa ataaaccaat aaaccaggac ctaatacttg gtctttcta    27540
ccttattact ttggaggcgt gacaaaaagt tcagcagaca gtaaaagcca cctcagctcc    27600
atgtaatcac acaaatcaga aatgaaggtc caagtgatag cattcaactg aaatccaaga    27660
ttttggtccc tacactgagc agaatgaggg aggaagtgaa gtcattcagc tgccacttca    27720
actctgggac acaaaaacac aggtggggac acctaggatc ttatttaata ctagaataaa    27780
aacaaaagat gaagacagtc cactgtcatc tcagctttga gggtcacacc tatcaccccca    27840
gccctagaga ggtagaggca gaaagataaa aagttcaagg atatccttag ctatatagca    27900
aggtgaaagc cagcctgaga aacataagca tcccatctca gaatttgaaa tgaagactgg    27960
caatctgaat aggaatggcc accatacatt catgtatttg aatgcttggc catatagtgg    28020
ctctattagt aggtgtggcc ttgttggaag aagtatgtca ctgtggggga gggcttccag    28080
```

```
gtttcatata tgttcaggct acacttagtg tagtgcacag tctcttctct ctcccccagc   28140
actgtgtctg ccatgataat ggactgaatc tctgaaccca taagccagcc ccaattaaat   28200
gttgttcttt ataagagttg ccttgattat ggtgtctgtt cactgcagta aacctcaaac   28260
taagacattg atataaaggt aattcactgc attagctctg agaatagatc tggagacttt   28320
gataaacact aaagtgttag gagccatcta ggataggcta aggctagcag gtggccttcc   28380
tggaggtggc ccaccgtttt ttgcatggtc tgctattggt gatcttgatg gcaaggttcc   28440
aaagagactt catctcagga ttgcttcttg cagctgatat gtctttcctg tcattattaa   28500
attaatataa taatcctcag cattagccca ccctgttgat cagatttcct acatattgaa   28560
gtaaagatga actttcatga attaatgcta tttaaattaa ttaatgattc tacagaatat   28620
ctgatttgat tcaaataatc ttagaaagag ttttaaagaa tggtttcagt cattttgcta   28680
aaaagatgca ataaagtaag aatcaagaat agaatgtgcc cactcctcat aatagtaaag   28740
ggtgcataat aagaaataca atgagctttc ataattacac taaaaagaga ataggcttg    28800 ggataaattt gtgttcaagg aaatgcattt aagcccaagg atggagccac aggtgtgcac   28860
tatgataaga caaggccatg tgaaaactgt ggctttgaac ttataatgag catatagaat   28920
gaaacactgc tttgatctta atttcaacat ccttctgtaa ctcccatttt atctaacatt   28980
ttatctctga agtaattttc taagaacatt tttgtctaag aaagtataaa aaggccagag   29040
aaaggaaaga aaattgttgg tttgatggtt tggtttgggg agctctgccc catctatcca   29100
tccacccatc catccaaatg tgtatatctg tttgtctata tgtaagtgtg taggtaacta   29160
tgtatgtgtg taggcatgca taaatacttg tggagatgat tgtgactgat ggtcaggcct   29220
ggccagagtg tggatgatga atatatatgt gtctgtgcat atttgcctgt ataaagcatt   29280
ttgattcttt cctttccttc ctctctggtt cacaaagagt taagcagcct agccatggag   29340
gcttctggct gcctggacag agaaaggagc actagcaata aatcctttta gttaattccc   29400
tgacactaaa cagcatgtgt taatcaccag atattagtgc ttatttaagc acaagtaagt   29460
aagagttaag ttttttagcac aaaactaata gttgttaccc cagagcttaa agaagcacag   29520
aacagtaaag aaaagttaag tttttagcac ttaatgaagc acagaacaaa aacagagtta   29580
taaaataaag atacagcatt taataaagca tagagattta taaagaaaaa ggaagctaca   29640
gagagttaaa gagaaaagaa gccagcagtt ttcaaccaca gaataaacaa gagactgtta   29700
agtctacaaa gccatcaaca aatattcagt aagtatagtt agagagctag gctagagacc   29760
atctgtcttt aaatctatgt ccaatgctct gtcccatttc aagccattcc aggccagtct   29820
ggctcccgac atctaaataa gattggaaat tagaaataac gagtagtaga aggtgttact   29880
taatgattct gtttgtttca tttaactgca ttttttcagt gtactttgtt ttgttgctgt   29940
tgtttttgag atagggtttc ataaagccag gctggcctca aacttgctat gtgatagcgg   30000
acgactctga actcctgacc ctcctacctc gctcttaatc attggttctc aacctgtggg   30060
tcattccccc tttgggggtc acatattaga tatcttgcat atctgatatt tatattatga   30120
ttcataacag tggcaaaatt agttatgaat taccaataca attattttat ggtcagcaca   30180
atatgaggaa acatattaaa gggtggcagc attaggaatg ttgagaacag gttttttgtt   30240
attgtttgtt ttttggaggt gggtttgggt ttgggttttt gtttgttttt tgggaggac    30300 ttgggattca tgagattcta tcttagatat aatgaaataa ataagaatac acgggcttgt   30360
aggtagcttg gttccttcat tctgtgtaaa tgtggatgtg tggtcctgat cccataagag   30420
```

```
ggggccaagg agcctgtatt ggtggggtct gtgattcttg gccctcaatc ctatcaaata    30480
gccccaagaa cctctaaaat aggctaagca acaattcatt catcccaggg tataagtttt    30540
cagaatctca aagtaaaatt gcctggctaa gggatgctga aatgctcagc aggtaaaatc    30600
agttgcatca aatgcaagtc tgacagaaca acacaagcac aatgacccaa agttgtatt    30660 cttccttcac atgtatatca taccatgtac acatacccac atatacacat attatatatg    30720
catacataat aaaaatgtta agtgcccagc tgaagagtca gccctgatga ctcatgcctg    30780
taatctcatc actaagaaga ctggttcctg aagactgcca aagttctagt ccagcctgga    30840
cacatggtga gttttaacct aacctggcat acaataaaga aacaagctat ctgaaaacaa    30900
aatgtctggc tgagtgaagt attttatacc agtatccctg gtactctgga ggcagataca    30960
agaggatcag atcaatagga ccttgtcaca aaaaactgag aactagacca gagagatggt    31020
tcagtggcta taggcacctg ttgcccagct caatgacctc actttgatct ctgaaaccca    31080
catgatggaa ggagaaaaaa aaaaacacct tcaacttgtc ctttgatctc tgcatataca    31140
ctgcacactg tggcatgtac atgcctgcac atgcccctcc acacacacac atatatatat    31200
atataaatgc atacataaaa ttcaaaaaga ataaaaacta aggatatata tatataaata    31260
catacataaa attcaaaaag aataaaaact aaggatagct caaaacttac ctagaattta    31320
cctagcatgc ccttgaccta gatcagatct ctgacactga aaaatggag aggcaggtaa    31380 ccctctggtt aaaaaaatca gagagaagcc gggcagtggt ggcgcacgcc tttaatccca    31440
gcacttggga agcagaggca agcggatttc tgagttcaag gccagcctga tctacaaagt    31500
gagttccagg acagcagggg ctgtacagag aaaccctgtc tcgaaaaacc aacacacaca    31560
cacacatcag agagaaagag agctgggctt tgtagcacat gcctttaatt ccccactct    31620 ggaagcaaag gtacacagat ctctgagttc aaggccagtc tggtctatat agcaagctcc    31680
aggccaataa agacatagtg agaccttgtc accctcaaaa aaatttaaat aagagggaaa    31740
atatcattaa aaatagaaag ataattgttt tggttttgt tgtttgttgt actgtctatt    31800
gattatataa catcctaagc ccttttaca ttttgttt gttttgtgtt tttaagacag    31860
gcactatata gctctgggta tcctggaact cagagatcca cccagccttt gcctctcaag    31920
tgctgaaaat aaaggcaggt accacccagg ctccttctaa actttatttt gatacatggt    31980
ctcactaaat tgtccaggct ggcactgaac ttgtgattct cccacctcag ccacctatgt    32040
agctggagtt ataggcctgc atcaggctta tctagaaaac atagtttcta aaacaaaaag    32100
aataccaggc atgatgatgt taatctctag tcttatcgct ctggaggcca aaagcaatag    32160
aattaatgca agtttggaat taatgcctac tctacataga gagttctagg ccagccaggg    32220
ctataatgaa aacccgttac aaaagcaaaa aaacagagcc aatgagagga gccagctgat    32280
aaagatgcct actgccaagt ctgatggcct gaattcaatt cataggcccc acgtttgaaa    32340
gaaaaaactg actcctacaa aatgcccgca gacctccaca agagtattat tatgccactc    32400
cagtgcatat aagcatacaa aatcacaaga tagacatact tccagataat agataacata    32460
taataaaata attttctta aaaagcaagg gcatgtcttt ttgggatcat tttcctccta    32520
ctgggtggcc tcatcacacc tttctacaag gcaaagtgtc tagtcttact ggaacatgat    32580
atgccatggc tgtttgatat ccatgggagc cctacccttt tctggaggag tggataggaa    32640
gggggtcaga tgagaagtgg tgggcattgg gaggagagga ggaagggaaa cttcggaggt    32700
ggaagcaaga agattgggag ttcataacca tccttcttaa ctacatagcc atccctcttc    32760
acttggaatg gaagttttgt ttatttaatg tcatagatac agaaagcaaa tcaagggggtt    32820
```

```
gccagaactg gattttaata gagtcggaga aaataaatgt tctaaatacc ataaattcta   32880
tactttaaaa tggtaaatgt catgacatat taatgaaaca tctaataaag ctgttattta   32940
caaaggaaaa ggctagattt ctgcccctca aaaatgaaag tttggggctg gagaaatggc   33000
ttagtcaatt aagaacattt gtggatcttc caaagagttg gagttcaatc cccagcatcc   33060
tcaaggtggc tcacaactgt ctataatgcc agtcccagag gacctgatac ccttttctgg   33120
ccactgtagg catggtaccc gtgtggcaca cagacataca ctcaggcaaa acacccatac   33180
acatacaatt tttaaaagga tgccaggcat gatgacatac acctttaatc ctagtatttg   33240
gaagatagag gtatgcctct tttttgtgaa tgaggatagc ctggtctaca tagtgagttc   33300
caggccaacc agggatacct agtaaaaccc tggagagagg gaaagggagg gatggaagag   33360
aaaggaaaga aggaagactg gaaaataaat aaagggaaaa tctcaaatga aagtatgtcc   33420
tctggggttc tatcagtgcc cacatattct tctatagagg taacttgcac atcctagagg   33480
tatagcattc tgaattcatg ggtcactgac acctatcagc ttgcattcag aaggagcccc   33540
tagaacagag gatatgcaga gtcagcaccc ccttgcttac tacattgcta ataatttgtc   33600
ccatccaact ttatatacct aagatcacaa atgcatactc atcagtattt ttttttttt    33660 tttggttttt tgagacaggg tttctctgtg tagccttggc tgtcctggaa ctcactttgt   33720
agaccaggct aacctcgaac acagaaatcc gcctgcctct gcctcccaag gactgggatt   33780
aaaggcgtga gccagcacac agcacaccca gctagtaatt ttaagatgac aagatgtcac   33840
atcaagtatg tagtcctaag cacagggtcc tggatgaccc tgcaggacac taaagtatag   33900
gtataacttt tccttaacct actttagtaa gggttcaacc tcccctctag cccaccatcc   33960
actagaggtg aaaagaaag tttaggagga tatggggtaa gtagaactgt ttagaaatag    34020
ttctttgggg agattccaat cttcattgtc agtagccttg tcctctacca taacaccaac   34080
atgaatcagc agctgcagtc cagttcactt ggcaatcacc actcatgagt cagcaagagc   34140
agttcaattc agaagaaact gcaaggctca ccaatcagct cgagtctgca gaagaaaccg   34200
caggaacctc atgagaagtt ctctatgaag tcaccacaaa taaagctcag caatgcaatg   34260
tatggcaaac caatacatgt gtatcgtcag caaagactac caaggcagag caaggcaaac   34320
caatgttcta gctcccattg tctgtgtggt catatgtata ttctttctaa acatcacgtg   34380 tccttttcaca tgcctactat agcaaaacat cctctcacct gtgtctgctt ccgaaaacat   34440
tttcacatgt ctcccttggc aaaacatcct ttgacctgtg tgccccagca aagcatcatt   34500
tgacataact gactttccaa cgaaaccaga agtttccact tcaaaaaaaa catcaaacct   34560
gacctcactc ttcagactaa acctcaggca cacacagctc tacaacttgc atccacatat   34620
tcacatatgt ctaacaatgt gtcacatctc cagtaaacca tcacagtaca aaagagtaca   34680
gcggatgctt tcctgctccc acccttcctc aacccagatg tgtctcactg ctggaactga   34740
gccaccaagc aattacaggt agaaaaggtc aaaaccccag cttgatctgg cctgcctgct   34800
gaggagccag agggcatagg aggaccagaa agacagagat acagctgggg agagcctttg   34860 agacttttg gactttgaga agcaaccaga acggatcatc cttccttttc tgacagaacc    34920
tccagaatcc tccctctaaa agccatgtat ggcacatgcc tctgagctca gcacttcaca   34980
agtcctggcc gtaggaatca tgagttgaag ggcagcgtca gctatatagc acatttaaga   35040
acagctggga aacatgaaag accatctctc aaaacaaaca ataccaaaaa taattcacca   35100
tgatgttact gtaagaatgt aatgttagaa ctcagaccaa actactgctc atgcccacaa   35160
```

```
agcctgaagc agcccttcca ttcccacaga tactgacagg cccccctactg aaggcattt    35220
ctattagtgc cttacagact tccaggtgca ccacacatcc tggtccccac ctccttctat    35280
cttgagttct atcttaaaac caaagaacct tgctgcaagc tggtactata aaccatccct    35340
cttcctcaga gagctataag acaggacttt gacactgcct ggagagctct tactcctctt    35400
tggaagccct gtttctggtg ctgaggcctg gactctcctc agatcccctg ccatgctgct    35460
gtctctttgt ccagaatatt aataattctt ctaataagtt tcttaccccc accaaaaaat    35520
atctatccca gtgtctctct tcaacatgca tccaagacct ctcagttacc agtttctgag    35580
tgaaactggg tcattttctt tccagaatca tagccccagt gacaaaactg tgaactgatt    35640
atgcagtgat ggaaaggttc ccctttggcc agagaataag aaatcaggag aaagtgttca    35700
cagaccagct tcctgtctga gcagaaggcc aaactggaaa tgctattaag taacaagtaa    35760
gatgactatc caagacttct tcaggaaaag aataaacagg tctaaataga gtcctctatg    35820
gctgaaacca gttttatcct attccaccct tctctgtttt cacaactaaa gtcaaaatat    35880
ggagtgtctg tatgaatggc tagcactttg tctactagca gaaaagactg ccttcctgag    35940
atgaaaggct atttccctga tggcacttgt tctctggggtt aaacagagtt tacctatgtc    36000
acataacagg ttacctatgt cacataaaac tgtgatcaaa taaattaagg attttctctt    36060
ctcaatcttc ttttttactt tactcagcat cagttactat attaagaatc tgagccgggc    36120
gtggtggcac acgcctttaa tcccagcact tgggaggcag aggcaggcgg atctctgagt    36180
tcgaagccag cctggtctac aaagtgagtt ccaggacagc cagggctata cagagaaacc    36240
ctgtctcgaa aaaccaaaaa aaaaaaatct gttttattat tgttctgaga ccggggtcag    36300
taaatgtagc tcaagctgcc ctggagggta gctctcctgc ctaggcttcc caagtgctgg    36360
gatcataagc atgcacacat ggctttaaca taaaggtatt gtcgttactg ttgttttgtt    36420
gggtttcttt ttttattttg tgtgtatatg tgagcaccta catagatgta tgcgtaccat    36480
gtgtatgtct agtgcctgag gacatcagaa gaggaaggat atcagtttcc tggaattaga    36540
attataagtg gatatgagct accatgtgaa tactaggaac caaaccaaac aggtctgtga    36600
ccttttttttt aatcttattt ttaatgatgg ttcttaaact cttttaacctc cctttttagcc    36660
caatactcac cagagggaaa gaaaggatat ggggaaagta gacctgttta gaaagattct    36720
ttggagcaac tcccgtctgt gttgtctaga aatcagcagt tcagttcacg tgttagcaga    36780
cagctcaatc cactcgcaaa cacttcatgg atacaccaac agtccagagt agggatagca    36840
aacatgaatc agcagcggtg acacaaccta gcagagacag ccaggcctca gcctctgcac    36900
aagtcagcaa gagggacgga ccccagaaga acaccaaaag aagttctcgg atgtgcctct    36960
ctcagcaaag caaagatcag tgagaccaac aagcattaca tagccagctc tataagcaca    37020
cctagctcag cctctgtcac tgtctattgg gtcctattta taccctccaa acatcatgtg    37080
tcctccaggg cttgcctcag cacatgcatc tgtctcagct gacatcactc tgccaatcag    37140
cctgaatctg aagaagcggc aagaaactgt agcacaccac cagaaatttc tctctatgga    37200
gtcctgacaa atacagctca actacacaac ataaggcaga ccaatacatg tatcatttgc    37260
aaagaatccc tcatcatgtg tccttttcatg tgcctgcttt agtgaacatc ctctctcctg    37320
tgtctgcttc agctaaacat tccttcacga gtctccctta gcctttcacg tatgtccact    37380
tcagctaaat gttccttcac atatttgccc cagaaaaaca ccatccaacc ttaagttttc    37440
acttcaccag tcctctgaaa gagcagtaag tgatttttatc ctctgggcca tctctccagc    37500
cctctggttt ggtttggttt ggtttggttt ggtttggttt ggtttggttt gagacaggac    37560
```

```
tttactatgg atctcagaat gctggcattg gacttatgtt attgtatacc caaggagggc    37620
ctcaaatttg tagtcatcct cctgccttag cctcccaagt actgggatta caggcatata    37680
aacaacacct agtttttct atcagcttaa aaacctccca aactaggatg cattacagtc     37740
ttttaggaca ctacatagaa catattgact aggttccaaa tacaatactt ttaggggtag    37800
ggatgtagtt cagttgatag agtgtagttc atgaagccct ataggtccca tttctagcga    37860
tacataaaac taaatgtagt ggcacactac tgcgatctca acatgtatga ggtggaggca    37920
ggagaatcag aagttcaaag gggaggggag ggagagaggt aggaatgaag aagaaagaaa    37980
gttagctaca ggttttcaat attccttgaa gaatgcacgt gcgcgcacac acacaatgtt    38040
attcaagttg tcttttaatg atacaaacat gaaatcttta aaaacaaaga tggggtttta    38100
aaaacaccaa tacttaatac gacagcattt agctaacttc cctgccctgt tcaatctgga    38160
cagagcacag tggctttcta aagctacatg tagaatctca catatatttt tgtttgccca    38220
accaaaatat caacaaaagt gaaatattta gaggtttggt ctgaagagat ttctcattga    38280
taagagtatg tattgccttt tcagaggacc caggctcagt tcccagcacc cacataacag    38340
ctcagaaaca tctgtaactc cagctcgagg gaatgcaaca ccttcttctg gcctccaaaa    38400
gcaccaagta tagacgtggt gcacagacat acacgcaggc aaaacagcca tgcacataaa    38460
ataaaacaaa taaataaat ttaaaattta aaaattaata aaatttatct gtcaaatgtt     38520
gaaaatgtgg actagagcca gatatgctgt catatcctat aatcccagca tttaagaaac    38580
agagacaggg gggctggaga gatggctcag cggttaagag cgccgactgc tcttccaaag    38640
gttctgagtt caaatcccag caaccacatg gtggctcaca accatccgta atgagatctg    38700
gtgccctgtt ctggagtgtc tgaagacagc tacagtgtat acaataaata aataaataaa    38760
taaataaata aataaaaaga aacagagaca ggagaacatg gagttcaagg ttatctttgc    38820
atgcacagta agtgtgagcc tttttgtgtt cacttcactc tgatttcatt acatgtattt    38880
aaagttagtg tgcatgtgtg cagatacagg tgtcatagtg aagagacaca aggtaaccca    38940
cccttgtctc tgtgcgctga gtctctcact ccctagtccc catgccaagt taaacagcca    39000
gcactcccac cttggtgcag atgtcccta cctttgaagg aggcagaaaa ttaatgccct      39060
tgaagtgata aggctcccat tcttgagcta tcagaaagag gcaaccgagt gttcccagac    39120
agctatggcc agcttgtaaa aatacactag cctctgatta cagaatgagt tatttctccc    39180
caggtcaaaa agatcctttt ccagatgtat caaacaaaca tcagttttga aggatagcat    39240
tcctttactg cctatcatgt aatgccaaga cttgaatgcc ccagcttatg catctcattc    39300
atatatatat atgtgaatat aatttaacca tttaattgta ttttttccaa gacagggttt    39360
ttctatgtag ccctggttgt cctagaactc actctgtaga ccaggctagc ctcaaactca    39420
cagagattca cctgcccctg tctccagaat actgggatta aaggcatgtg ccaccatccc    39480 tagcttaat tgtccatttt aaatgataaa gggctgaggt tttgtgtcag ccataaggca     39540
tatgtatgtc aaaagccata aatttaattt tcagaacaca cacacacaaa gtcctggaga    39600
aaatagactg aaagtttgtc ccatgagtca taaaagacct ggatctccac ctataatccc    39660
agaactaagt aggtataagc aagaggtcca aggacatcct tggaaacata gtgagttaaa    39720
gaatatacga aattcccatc tcaaaaaata tgtagcagga ctgggtgtgt tagcatacgc    39780
ctttaattcc atcattcaga aggcatttaa ttccatcatt ctgtacattt gaggccagcc    39840
tggtctacag atgcccttga ccacaagcat tggagagtgc ctatgaggaa gtactcagtc    39900
```

```
aatatggaaa ctactgtatt cttttttttt taatattcat tttgttgttg ttgctgttac    39960
tattttatct ttacttaatg ttttatttta aaaattaatt attatttgtg tgtgtgtgtg    40020
gaggaggagg aggaggaaga ggaggaagag atcagagagg tgccagatcc cctgaagcgg    40080
ttgtgagctg ccttatgtga gtgtaaggaa tccagcccgg gtatcctgca agaacagtat    40140
gtgcccttaa ccactgagtc atctctccag cttcctacaa ttttttgaaat tttattttt    40200 ttatataagt ggtttcccta catgtaccac atgtggtacg tgtaccacat gcatgcctgg    40260
cgcctgagat ggtcagaata agacatcaga ttccctgaga caggtttcat gcagctaagg    40320
ctgacctcaa agttgctaag tggccgagga tgctttaaac cctttatcct cctctcccgt    40380
ctccactttc caagtgctga gattacaagt gtaaccaaat tgaaaacgct atcatctaac    40440
caaaacagtg cttctgtaaa cttttctgta ttttggagca ttatggaagt ggggtggagt    40500
tcctgtaagt aagaccattg ggtcaaagga caggaatgca gctgcctgag acacagatag    40560
atccagctta aaaggactgg cccagctgcc ctggcactgt aggcggtcag gggaaaaggc    40620
tcaaacatga gggtcaggag caatgttcca aacatcccctt cactgattga tacataaaac    40680
agaacgctct cacgaaagaa cactaagcag aaagaaagca accaaaggct caggtttacc    40740
tccgcatgtg cttctgaacc gtccatgctc ttaaagaaca catatcaacc ttaagtcatt    40800
atctgtgtcc ccgcatccat cctcttatga gccatgaaag ctctgatatc aagtcacaat    40860
cggagcttca gctcatcaaa tatagaaata gatcgctcac ctaagaggac gtgtggagga    40920
agtgggaatg ggggctctgg tgttttatgc ccgtaattcc aacatttgag agcctgaagc    40980
aggtgaatcg ctccaagttt gagaacagcc tgggttacat agagttaagc aaacatgaac    41040
tgtaaagtgt atagtacctc aaagtctaga aggagatttc atcttgaagc agtgacactg    41100
taggaagcta ggcggctcag ctttagcaca agaggagtgc acagccacac tcggcacctc    41160
ccacccagcc tctggaggag agggaggagg ccggtctgga ggtggagcct ccgtgaggac    41220
ctgcggacct acagcacagc ctatgggcct atggcggagc gacgcctgtg ggctgtggcc    41280
ttctgcgggc ggccattgtc gtgcctgata agcttttcta cgtgactcac ttgcttcacc    41340
tagccggcag agcgagacaa ctgggtaact ccctgatccg gtctgcttct ccctacaccc    41400
agacaacatc cttggcccgc ccaatctctg ccaccagcct cgagcggatc gacctgagcc    41460
ccgggcctag caccggaggg atccgggtgg agaagaatca ttgctacgct ccagtcctgg    41520
agtctgttag ccagactgtg aggcgcaacg gattcctaag gctctcctgg ccaggcagga    41580
cttctcccag cactcacgag gaactgagcc tggactggtg tttggaggaa caagtcataa    41640
caccgatcgc tcccagcaca gacttgccac tgcccccacc cccaaaccta ctctctcctg    41700
tttcattccc cccagaaccc acagttccca aacagtgcac ctgcgggaga tctcaaccca    41760
gctggagaag tggacatgag gttggcaggt gggtggcttc cacagcgaac tgaagagagg    41820
ccaggtgtcc tagtgcctgt gttaggagag gcctgggtgg tcactggttt gtttatttat    41880
taatggatga ctgtgcacaa gcactcattt tatgagcaaa ttcacctctg aggacttcag    41940
cttcccaaac tataaggatt gattttatat agagagatag atatagatag atgttgataa    42000
tatatataat caatatatat aagttaagga tatatatata tatatatata tataaaatct    42060
ccagagattg aatggatgga gaggagtgga tagtagagat agagagatgt agccagaaga    42120
gaactgactt aggtgccttt gaggttgggt atgatctaag tggtagctct gctgtcagct    42180
ggactacaaa catgaatgtg ccttggaggg actgtttggg gtgagagtag aatttgaaaa    42240
ctggtaaagt agcagctttg tggataagtc caaattggac attaaggaac tggctgggag    42300
```

-continued

```
gatatgagtt caagacagat ctgggctgga ggtgtaaggt gtcattgctg catggtgaaa    42360
tctcccatac agtatgaaga tgggagaagg cagcctggaa aagaacacct tttgaggaga    42420
gagtaatgga acacaatcta accaacaaag ggagtcccag agaatggggt caggagacag    42480
tactgtcctg gaatctagta gtgaagtgtc aagaaagagc agtcagacaa tcagaaatgt    42540
gacatcataa aagtcatagg tggtcttgtt tggaaggtta tttagttggt gttatgggag    42600
cacgactaga ttggaagaat tttgggagag agttggggag tgaggtaata gaaatcacaa    42660
tgtagatgac ttttatgtgt atgctggggg atggaaacca gggtcttatg catgctgagc    42720
aaatgctcta ccacagagct atatcccaag ccagaatata aatttttaaa gagtttggtg    42780
gagaagagga agatgaagaa tcaaagaatg agatttttct ttcaggagct ctgtttcatc    42840
tttatcttac taagttagga cctgttgata atatgagaga aagtgagata gaagaagtc     42900 ttagcacaat gtatctgaga caggagatat cttgatggat cctgaagcag gtagaaggac    42960
tggtctttac aaggagtata gagcttccaa cagaacaaga ggaaaggcaa agcagatggg    43020
tgaactgtaa atattctgat aatttcagag gcaagatgct gaggttggtg ctatgaaacc    43080
ttcccagagc atgagttcta aaaggcacct ccaaacctgc tggggagacc caaacagagc    43140
agcctcaagg tttgaactca cgttcttccg tctactagga ggaagttcaa gcctctcttt    43200
tgggtctggt agatatcgat tggtccccca cctcccaatc gtaccatcac ttgttcccaa    43260
gtagaagggg agatctggtc atgtgaggta gtgggttatt gcagattttg ttcactgatg    43320
tctaagatag tcctgctctg tgtctatcct gcctgcaggc cccctgcgca tcgtggccct    43380
aatcatcatt atgggtctca cctggatcct agtcaccatc ctcctaggtg gtcctggtgt    43440
tggccttcct cgaattcagc agttcttcac cagtgagtgt gggaatcctc ttgattcact    43500
atagaggcgc ccaatatggg ttatggtggt tgggtttccc attaccttca tggcaggctt    43560 cctttttgccc taggtctatc ttctaacaca aatgcatcct tgtttccacg aaccatccta    43620
gagaacaaca ctcctaattg taaccaatag agtggaagtt gatagagtaa gagtaaggag    43680
tggaaaggcc tccattgatt attaatcatc ttcgactttc cgttgagctc tgagacacac    43740
aagggatctt gcactttgtc actggtgcca agtcacctaa gcactattta caattccaat    43800
tcatcctttt cctgaagcag gcagttttat atcagggcat cattgaaact tgagcgggga    43860
acatgccaag tatagcctga cttggccctg agtccctgag cctggttgtt ctgctggagg    43920
ctcctggagg cctccctgct aacagaaaaa actctctact tacaggccca gagaactcag    43980
tgactgcagg taagcctcct gtcccttccc tattccccc gtacctgtac ttcagactgc     44040
cttttgtgac accectgcat gctgtcagcc agccccacta ggatctccat tctctgtctg    44100
gcctctccca actaactatc ataggcttct gggctgtaaa cctaataaat gagttagcca    44160
ccatcagaag atgaaagggg caggcatagg aaaaaaacat tcccattcca aacaagagac    44220
attgggatga agcaggggct catggtccta agcaagtccc aatcatagca gggcaagttc    44280
tagatgtcaa ggcctaagaa gaaatctcta tatcattctc taggcccact gaagtgactg    44340
catcctctgt tccctctttg gcctcttcat tcctagctct gtattcaaaa tcaacctacc    44400
tacctcccac ccttccttcc tttctccctc ctttctctct tccctcactt ccttctttct    44460
ttccttcctt ttgtctttca ttcctttgtt tcttccatcc ttgtattctc atctcagttc    44520
ttctcatagg ctgacaatat ttctgttggt ataaatctct agcaaatttt gctggcctct    44580
catgcagttc ctgaaggcct aggttataag acaagacaat cctccacaga tccattctgt    44640
```

-continued

| | | | | | |
|---|---|---|---|---|---|
| ataatcctat | ctcaagtcca | ggcttctgag | aggtaggagc | acacacacaa | tcatgtgctt | 44700 |
| catttcctta | gcaagttctt | agcgagccat | catctctgtg | ttctctctaa | aggatgcttt | 44760 |
| tttaaacgtt | ttatagtgct | gggaattaaa | cccaggacct | tacacatacc | gagcaaatac | 44820 |
| tctatacaga | gctattttc | tagcccataa | aatgtttccg | gtttttgac | agagttttac | 44880 |
| tctataatac | aaactgacct | tgaacttact | atgtagctct | caagctctat | attcctcctg | 44940 |
| tgttacccta | tcaaattctg | gaattacggg | tttgacatgc | attctcaatt | tttcaatata | 45000 |
| attagactaa | cattttcttt | ctttcccttc | cctttgtgac | agggcttaat | aaatgcaagg | 45060 |
| ctatcattaa | aatcacttta | aaaccaaggg | taaccttaaa | ttcctgatct | tcctgcctcc | 45120 |
| atctcccaag | tgctaggatt | acaagcatat | gtctggctag | gctgagattt | ttctatatat | 45180 |
| ttatgtccta | tttccttcat | gattaatatt | tttccccaac | tgttctcatt | ctcattttac | 45240 |
| cataagcagc | agcaaggaaa | aaccagaccg | tacctttaac | actgtgcttg | acaatttcct | 45300 |
| ttgctaaata | ttttacaagc | tttctctcct | acaaaacacc | agaacaattg | acactttata | 45360 |
| acaaggctga | gctttcctcc | cacacccaat | aatggcctct | tcgacttcct | tctaaggtct | 45420 |
| caccgaaaga | tctataatat | tcatcttcct | aacaacacct | tgtttaggga | tgtaagtgaa | 45480 |
| agattcaaca | gaagaatttt | cattgctgtt | tctttctgag | cttgcaccag | aaatatgttt | 45540 |
| actatccata | ttgctagatt | tgttttaata | tagaggctta | ctatacaggc | cagaatagac | 45600 |
| ttgaaatcat | gatccttctg | catcatcctt | caaagttctg | gaattacaga | tatgcagtac | 45660 |
| tgtacctggc | ttcactctgt | attcctacca | acagggtttc | gggttttctt | tgttttgtt | 45720 |
| tttgttttg | tttttgtttt | aagcagtgca | gactcttct | actgtacacc | tcaaaactct | 45780 |
| gtagcttttg | tccactctac | ccagttctaa | atccattttc | acatccttag | gtatttgtgg | 45840 |
| tatttgttta | tataaacccc | caattcctgg | caccaaaacc | tatattagct | tcctgaagct | 45900 |
| acactaagaa | aagcagaata | aagcaggtgc | cttaaacaac | caaaatttac | tttctcacac | 45960 |
| tgtttggaac | tgagagtgtg | aatggaagtg | tcagcagggc | tgtgttcact | ctgaaagctc | 46020 |
| caggtcaggg | tctttctgtg | cctctgcaga | ttctagaagc | cttctatgtg | ccttatctta | 46080 |
| taactgcacc | ttttgcctgt | actgtctttt | gcctgtactg | tctcacaaca | tctcctgtat | 46140 |
| gcttttgtct | cataaggaca | ccagtcacac | taagttaagg | gctcaacatg | ctccattatg | 46200 |
| acttcatcat | aacttatcta | tctgtaaaga | ccctgtttcc | cagccacatt | ctgaggaact | 46260 |
| gagagttcca | actccagtat | agtttatagg | gtcataattc | aagccattac | agaggtcatc | 46320 |
| tccaccctta | ctctgaagaa | atacagaggc | tagtagagcc | ctgtgctctg | cccatccact | 46380 |
| ttggtctgtg | ttcctcattc | atgtagctcc | catcctgact | ttctggaccc | tctgctttgt | 46440 |
| tctagttgta | caagggttct | aatccagctg | tcaacctcct | ttccctttc | ctaccaatag | 46500 |
| cagaaaaatc | taattcttgg | agtccctagg | tccttgccaa | cacaccactt | ggaagcatcc | 46560 |
| tcatctttgg | tgtgagcccc | acccacctcc | tcccccattt | caatgctctg | tagctattcc | 46620 |
| ttcagccctg | tggctggtcc | tgaccttac | cctcagatct | caggtgacac | cagggccagg | 46680 |
| catatgggtc | acatctgcta | tcattactca | gaaccaaggg | ccaggaagta | caaatgcggc | 46740 |
| ctgccccagc | cttgtcctga | agagcacctg | agctttcgaa | tagtcagcgg | ggctgccaat | 46800 |
| gtcatcgggc | ccaagatctg | cctcgaggac | aagatgtgag | catatgggct | gggaagtggg | 46860 |
| aggggaacct | gaggccaggt | ctataaaggc | caagggctga | tggttatgtg | aggaagagca | 46920 |
| aagctgatat | gcccacaaga | gatcctcttc | cctccccct | ccccaggctc | atgagcagcg | 46980 |
| tcaaagacaa | tgtgggccgt | ggcctgaaca | tcgccctggt | gaatggtgag | tccaccatgt | 47040 |

```
tatagggtca gaattcagat tatagaagca gataccatgg tatggcctgt cccctctact   47100
tcattactcc ctatgcagat gcaggtggct tctgggcact ccccaggagg cttgagaaga   47160
attctatacc cgctgaaagt agtgacaata atggtagatg cttaggacct cagatgccag   47220
tggctctatg ggatgtagct ctgtgattga caggatgaca ggacatgttt gaggcttcta   47280
gaaagggctg ccacccaccg tatttgagcc tgggctggag gctcaggtag taaaatggta   47340
tgtcctggct tgctcagcag ttctttctct tgatacaggg gtcagtggtg agctcctaga   47400
agccagagcc tttgacatgt gggctggagg tgagtggccc accacagcaa cctactgtat   47460
attttctccc tgaaatcctg ccctctgtct ttgcacttag ctgttcaagt attgccttgg   47520
atttacaaaa tacaagggat ggggaaatct gtctggattc tgttttgtga ctggatgacc   47580
ctagcttctt taccagttag tctgtgttca tactgatggt ctttggtgtg aacatccct    47640 ggcccagtcc ctactttgtt ttcctcatta aagaatatt gtttggtggg aagggctgc     47700 ttggtggaat ctgaagctcc atattctgtg ggcccatctc caccagatgt caatgatctc   47760
ttgaagttca tccggccact gcatgaaggt accctggtgt tgtggcttc ctatgatgat    47820 ccagctacca agtaagtgac tgccaagtcc agcttcaatc ttgttccaat acagtaataa   47880
tctccagttc acattccttt ctactgtgtg acaggatgaa tgaagagacc aggaagcttt   47940
tttctgagct gggcagcagg aatgccaagg atctagcctt ccgtgacagc tgggtgtttg   48000
tgggagccaa aggtgtgcag aacaagagcc cctttgagca ggtacagcag agaacctggc   48060
acctctgcct cctgtccctg gcaacctctt ctcaaagctt ccctgaattc tacccagctg   48120
ggttctggtc tctgtccctg acctatgccc tagtgatgcc tggcccctg ttatcaccat    48180 ggggagagac agtaactttg atctctcctg tcctgtatat atttcaacct aaggagtctt   48240
taaatgtcaa attgcacatt gaccagagta tacctaagaa atctttacaa gcaccttcag   48300
gatgctcagt ccagggatat agctcactta tggtgagtgt ttgtctagca tacatgaggc   48360
cctgtgttca atcattagca ttacataaaa ctgagcaggg gagacacctg taatatcaac   48420
actgtggaag taaaggcaag aggatcaact tatccttgga cacatatcaa atttgaggct   48480
agcctggact acatgaaata ctgtttcaga ttttaaaaag aaaaaaagat gctcactacc   48540
atcctaacct tgtcataacc cagttttcca gtttatgcta cacactcctt tctcacctac   48600
cctgggttct ctcttagggt acatcagtca gggtttatgc tagcggatgc tagagagagg   48660
agggcccctg gcatcatcct tacctaagga ggctctcagc aaaaagtctt aggtaggcct   48720
ccaagcactg ctttcaacaa atacagattt ctccattgct ttggctgaca aaacaactc    48780 aagctcatgc ctcccaagac ccttcacccc aaatagggta gcagtttcca gcatttccct   48840
gaagccaggg ccatatagac tccctcctgt ccacagtggc ccatccctag ttcacttata   48900
aaagaataga ccacctcagc catccccaat tttccctgtg tgaatgaagg gaagggcaac   48960
agactgaaga atattctgat gtttggcccc tgagagccag atcatgactt cctattaacc   49020
tctacagcat atgaagaaca gtaagcacac caacaagtat gagggctggc cagaggccct   49080
ggagatggaa ggctgtatcc ctcgaaggag catgcgggc tagcacagca gagctctggg    49140
accagactga aggaggcagc atggcaccag tgtcaggtgg agactgtgcc ccatgcccag   49200
gcatgaggct ccccctccct aacacattag ggcttgaaag tggcctcaag gtgatggggg   49260
ctgcagggct ggcccatttc attttgtcag ggagcttagg tacctgtgtc cttgttttcc   49320
taaagctgat cccacagtca gttcccaccc agccccttcc tctgcccctc atgtgtcatc   49380
```

```
ttctatttct ctttttttttt catcttctat ttcttgagtg ccccccagag gcaagggtct    49440
tcaatgcttg cccctgtcac tggagcaggt attgggtagg ttgggacatc ttcaagaaac    49500
tctccctccc agaggcactg cactggtatc caaccctgtt ttcagtgatc ctttaagcca    49560
aatcagaact gattggatga cttctgcaag cctgaatgga gcaatctggc cttaagtgcc    49620
caagtagctg gagtccaatc agagttcctc acaaggtgtc tgtcagaggg ctcaccttct    49680
aaatgacctg tttgttaata aactaatttc ttgcagtgga ataaagtgta ttcagatgtc    49740
ctcagtggag agtcaagggt ggtgttgtcc cgtgtgtgtg gagaagacag ataagtccca    49800
gaagctcaag cagcactctt ggagcttaag cagacagcct tttgtcaaca gaccctgtgg    49860
ccagatgtgg ctccgatagg aggtagaata gctcccagct gacattactc atggatttga    49920
ttagaaagat ggttctgttc aaaggaactc aaggaaactc accacctgtc actaatccag    49980
tgtgagccta taggggaaaa dataggaatt aaaaccagta caggcactga ataactcca    50040
ggagtgcaga agcagcctgg ttccaaaagg gaaagaatac aacttggaat ttctagatga    50100
gagacatcaa ggcatagtaa tttgaggatc ccataaagca tttctgaggt ggccatgcca    50160
ggggtgataa acttagaagt cctactgtgg caatctgctt tctaagcctt caacccattg    50220
ctgttcagta gttaagtctc agaaaaaaaa aaatggtgag gcaaatcag gcctcaagaa    50280
atgagagtag agctgggtat ggtacttata catctattat tccaacacta ggaagttgtc    50340
ttagtcaggg tttctattcc tgcacaaaca tcatgaccaa aaagcaagtt ggggaagaaa    50400
gggtttattc agtttacact tccatgttgt tgttcatcac caaggaagtc aggactggaa    50460
ctcaagcagg tcagaaagca ggagctgatg cagaggccat ggaggaatgt tctttactgg    50520
cttgcttccc ctggcttgct cagcctgctc tcttaaagaa ccaagactac cagcccagag    50580
atggtcccac ccacaagggg cccttccccc ttgatcacta attgagaaaa tgccttacag    50640
ctggatctca tggaggcatt tccccaactg aagctccagc ctgtgtcaag ttgacacaaa    50700
actagccagt acagaagtgg agtgagggag aaggatcaaa agttcaaatc aaactgtgac    50760
tacttagcaa attccaggac atcctggagt acatgaggta ctgcatccat aagggtgggg    50820
tggcttatta gataaatgta cctgctgcca aacctggtga tccctagaac ccatggtaga    50880
aagagagaag caacttttgc aagttgtcct ctgatcatat ggtagacatg tgcatgcaca    50940
tacacaagta agtaaatgtt aagaaagaaa aagaagaaa aagaatggaa gtatttgatg    51000
gcgggaatat gctggtttag aggtatgggg tgcccaggag aggcatgcta gggaagagat    51060
agttgtatat ccaagactaa cagagtcaag caggaaagtc agcagggctc agctctttgt    51120
ctcagatata gtggtgataa tagctaacac ccagccctct aagtctatac tgaactctgt    51180
gtgtgcctgt ttgtgcaggt gtactcatat ggattcatgt ttgtgtgcat tcatatggag    51240
gccagaagtc aaccttgagt gtccttcaaa tgctgacttt atttggtttg gttttttggt    51300
ggagttcgtt gctgtttttt tggagagagt tttatttgtt aaacagggtc tcactgtagt    51360
tctgtctggc ctggaacttg caaatatcct cctacctcta cttcccaacc gttgaaatta    51420
aaggcaggtg tcaagcctag cattagttac ttgttttgtt gtttgagaag tgtctcatta    51480
tgtcctggct gtcctgtaac tcacaaagat ctacctgttt ctgtccccca agtccttgga    51540
tgaaaggcat gtgccaccac attccactga gtttgttcat tcaaatggcc tggaactcca    51600
aattaggcat aaggccttgt attagtctgg gttctctaga gtcacagaac ttatggatag    51660
tctctatata gtaaaggaat ttattggtga cttacagtgt gcagcccaat tcccaacaat    51720
gcttcagtag tatctgtgaa tggaagtcca aggatctagc agttactcag tctcacacag    51780
```

```
caagcaggca aaggagcaag agctagactc ccttcttcca atgtccttat atggtctcca   51840
gcagaaggtg tagcccagat taaaggtgtg ttccaccaga tgaccttgaa ctcagagatt   51900
taatcttctg gaatccatag ccactatgcc tcaagatctc aagatctcca taccaagatc   51960
cagatcagaa tcttctatct cccagcctcc agataagggt caccagtgag ccttccaatt   52020
ctggattgta gttcattcca aatatagcca agttgacaac caggaatgtc cacttaagtt   52080
ctaagtaccc acctatgcac ctatgtctgc cccagcact  gctacgatgc ctgtcttttt   52140
ttgttgtgtt ttgttttgtt tttcgagaca gggtttctct gtatagccct ggctgtcctg   52200
gaactcactt tgtagaccag gctggcctca aactcagaaa tctgcctgcc tctgcttccc   52260
aagtgctggg attaaagacg tgggccccca cgcccccacg cccggctgtc ttttttattt   52320
gtgtgggttc tggggtcaaa cccaggtcct catgcttgca cagccagtcc tttagaaact   52380
aaacactcta cagcctctct gtaccagact ctgaaatata ttctgggggc tcagtggtct   52440
tatgttcttt ccccagcact gccaaaagaa aattacaatt ctgttgtccc cttttcaaaa   52500
gactttcttt ctttgagtca ttttaagttc ccagaaaact gaaaattaca gaaactgccc   52560
atcagactcc tgttggtcat aataagtatt ttttatatta tgttttctat gagtattatg   52620
tattctttga tgtttgtact ttttaatcat tttacatgtg tttattttct gtgcatatgt   52680
gtgaaaatca ggggacaact ttcaggaatt gattcttttc ttccttcata tgagccctag   52740
agatcaaact caggcccttta cccactgagc catctcatag acccacattc tttgagtttt   52800
gacaaaatca gataataaca tatatccatg attatcaaaa tgtatttgtc tcttgattct   52860
attatggaaa tttaaaaaaa tctcaaggtg tagagagaat aaaaatccag tacacctttt   52920
acctgcttcc acaatgtagc cagtattgcc tctgctacac ttagaatgta gccagtattg   52980
cctctgctac acttagaatg tagccagtat tgcctctgct acacttagaa tgtagccagt   53040
gttgcctctg ctacacttag aatgctccca atggagtcaa acaagtctca gcttattctc   53100
tcaagatttt agttttatac aacttgctta caaagttcac acaaccctag aaagtcactg   53160
ttgccactgt acaaaacagt tacagggcca tggtgagtat aggagagcta acaggacc    53220 tagaggttag aacaagatga gtaggctccc tgggttagca gcttacttcc agatgaagcg   53280
gaatctcact aaatatgctt actattagct agaagggcag agaccctaat gtgcatccca   53340
gatgattata acttttcaat cttttgtcttt gtgtgtgtgt ggggggggggg atatgtgtgc   53400 gcacacacac aagaggaagc caggggacaa ctttaggtgt tgttcctcca gtgctgtcca   53460
ccttgttagg gtatatggga tggggtacaa atgcacaggt atatagaagc cagaggtcag   53520
ctttcggtgt tttcttcgat tacttgccac cttaattttt ttaagcagga atgctttttc   53580
atatcttaat tttatttttta tgtgtttgtg cattttgtct gcacatatct ttgtgtacat   53640
ttttgctccc agtgcttgta gagaaagcgt ctgatcacct ggaactgaag ttacagagca   53700
gccagtgctc tgagctactt ctctagtccg tgtgtgtgtg tgtgtgtgtg tgtgtgtgtg   53760
tgtgtataca catatataca gttaattttt aaatactttc taatatttaa aattttttaaa  53820 tattttaatt acatttcaat ttactttgta tgtgtataag tgtatgtgta tgtttgtatc   53880
tgtgtatgtt gtagaggtac atgtcagaag acaacttgag agaatgggtt ctcttcttcc   53940
atcatataag tccctgccag ggatcaaact caagtcatca tgcttggtgg aaggcacctt   54000
gatccactga acaatcccat tgattcccac cttgttttct tttctttttt ttattgtgt   54060 ttttggtttt gttttgtttt gttttttcgag acagggtttc tctgtatagc cctggctgtc   54120
```

```
ctggagctca ctttgtagac caggctggcc tcgaactcag aaatccacct gcctctgcct    54180
ccctagtgct gggattaaag gtgtgcacca ccatgcccgg cttcccacct tgttttctaa    54240
gaaacagtct ctcattggcc tggaattcac caaggaaact aagctggctg gccagtgagc    54300
cccagggatc ctcctgtctt tatcttccca ccactgaaat tacaaacatg taccactttg    54360
ttctgaagat tgaaattggg tatttgtact caatttaact atcttccagg cccaaatttt    54420
gtccatttgc tttacggatg ttaactgagt gtcttgtttt actgctgtga acagacaccg    54480
tgactcttat ataaggacaa catttaattg ggactggctt acaggttcag aggttcaatc    54540
cattatcatc aaggcaggag catggcagca tccaggcagg catggcaatg gagaagctga    54600
gagttctaca tcttcatctg aaggcttcta agagaagact ggttcccaca tggttaggag    54660
gagggtctca tggcccacac ccacagtgac acaattcctc caacaaggtc acacctccta    54720
atagtgccac tccctgggcc aagcatattc aaagttttgt ttatttttac tctgtgtgtg    54780
tgtgtgtgtg agtgtgtgag tgtgtgtgtg tgagtgtgtg tgtgtgtgtg tgtgtgtgtg    54840
tgtgtgagtg tgtgtgtgtt gcaggcccat gtgtgccatg tgtcaaagcc agagaggtat    54900
ggggaacatg acatcccttc atctatcact ctgcattatt tctttaagac attttcatat    54960
tcagattcgt atctcactga                                                54980
```